(12) United States Patent
Sabuco

(10) Patent No.: US 8,445,478 B2
(45) Date of Patent: May 21, 2013

(54) AZETIDINE DERIVATIVES, THEIR PREPARATION AND THEIR APPLICATION IN THERAPY

(75) Inventor: Jean-Francois Sabuco, Paris (FR)

(73) Assignee: Sanofi, Paris (FR)

( * ) Notice: Subject to any disclaimer, the term of this patent is extended or adjusted under 35 U.S.C. 154(b) by 336 days.

(21) Appl. No.: 12/818,274

(22) Filed: Jun. 18, 2010

(65) Prior Publication Data

US 2011/0009377 A1 Jan. 13, 2011

Related U.S. Application Data

(63) Continuation of application No. PCT/FR2008/001748, filed on Dec. 16, 2008.

(30) Foreign Application Priority Data

Dec. 18, 2007 (FR) ..................................... 07 08830
May 6, 2008 (FR) ..................................... 08 02492

(51) Int. Cl.
*A01N 43/00* (2006.01)
*A61K 31/397* (2006.01)
*C07D 413/00* (2006.01)

(52) U.S. Cl.
USPC ................. 514/210.2; 514/210.01; 544/111

(58) Field of Classification Search
USPC ...................................... 514/210.02; 544/111
See application file for complete search history.

(56) References Cited

FOREIGN PATENT DOCUMENTS

WO    WO 2004/096763 A1    11/2004
WO    WO 2007/067617 A2    6/2007

OTHER PUBLICATIONS

International Search Report dated Nov. 13, 2009 received from the European Patent Office.

*Primary Examiner* — Shengjun Wang
*Assistant Examiner* — Uma Ramachandran
(74) *Attorney, Agent, or Firm* — Scully, Scott, Murphy & Presser, P.C.

(57) ABSTRACT

The invention relates to azetidine derivatives having the formula (I):

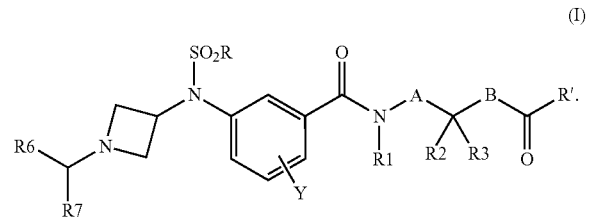

(I)

Wherein R', R1, R2, R3, R6, R7, R, Y, A and B are as defined herein. The invention also relates to a method for preparing the same and therapeutic use thereof.

13 Claims, No Drawings

AZETIDINE DERIVATIVES, THEIR PREPARATION AND THEIR APPLICATION IN THERAPY

The present invention relates to azetidine derivatives, to the preparation thereof and to the therapeutic use thereof in the treatment or prevention of diseases involving cannabinoid CB1 receptors.

The subject of the present invention is compounds corresponding to formula (I)

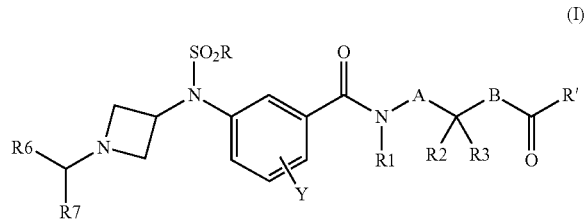

in which:
R is a $(C_1-C_6)$alkyl or halo$(C_1-C_6)$alkyl group;
R' is an NR4R5 or OR8 group;
A and B, if they are present, are, independently of one another, one or two carbon atoms, these carbon atoms being substituted with one or more hydrogens or $(C_1-C_6)$alkyl groups; the $(C_1-C_6)$alkyl group(s) being optionally substituted with one or more hydroxyl, $(C_1-C_6)$alkoxy, halo$(C_1-C_6)$alkyl, $(C_1-C_6)$alkylS(O)$_p$, NR4R5 or CONR4R5 groups;
A+B is at most two carbons;
R1 is a hydrogen atom or a $(C_1-C_6)$alkyl group;
R2 and R3 are, independently of one another, a hydrogen atom or a $(C_1-C_6)$alkyl group; the $(C_1-C_6)$alkyl group being optionally substituted with one or more hydroxyl, $(C_1-C_6)$alkoxy, halo$(C_1-C_6)$alkyl, $(C_1-C_6)$alkylS(O)$_p$, NR4R5 or CONR4R5 groups;
R4 and R5 are, independently of one another, a hydrogen atom or a $(C_1-C_6)$alkyl group, or form, together with the nitrogen atom which bears them, a heterocycle of the azetidine, pyrrolidine, piperidine, azepane, piperazine, homopiperazine, morpholine, thiomorpholine, thiomorpholine S-oxide or thiomorpholine S-dioxide type, this heterocycle being optionally substituted with a $(C_1-C_6)$alkyl group;
R6 and R7 are each a phenyl group, optionally substituted with one or more atoms or groups chosen from a hydrogen atom, a halogen, and a $(C_1-C_6)$alkyl, halo$(C_1-C_6)$alkyl, $(C_1-C_6)$alkoxy, halo$(C_1-C_6)$alkoxy or cyano group;
Y is a hydrogen atom, a halogen, or a $(C_1-C_6)$alkyl, halo$(C_1-C_6)$alkyl, $(C_1-C_6)$alkoxy, halo$(C_1-C_6)$alkoxy, $(C_1-C_6)$alkylS(O)$_p$ or cyano group;
R8 is a hydrogen atom, a $(C_1-C_6)$alkyl group, a halo$(C_1-C_6)$alkyl group, an allyl group or a phenyl$(C_1-C_6)$alkyl group, the phenyl group being optionally substituted with 1 or 2 O-methyl groups;
p is an integer chosen from 0, 1 or 2;
in the form of a base or of an addition salt with an acid or with a base.

The compounds of formula (I) may contain one or more asymmetrical carbon atoms. They may therefore exist in the form of enantiomers or of diastereoisomers. These enantiomers and diastereoisomers, and also mixtures thereof, including racemic mixtures, also form part of the invention.

Among the compounds of formula (I) which are the subject of the invention, a first group of compounds comprises the compounds for which:
R' is an NR4R5 or OR8;
R is a methyl;
A and B, if they are present, are, independently of one another, a —CH$_2$—;
R1 is a hydrogen atom;
R2 and R3 are, independently of one another, a hydrogen atom or a $(C_1-C_6)$alkyl group; the $(C_1-C_6)$alkyl group being optionally substituted with a hydroxyl group;
R4 and R5 are, independently of one another, a hydrogen atom or a methyl, or form, together with the nitrogen atom which bears them, a morpholine;
R6 and R7 are each a phenyl group, optionally substituted with one or more atoms or groups chosen from a halogen, and a $(C_1-C_6)$alkyl, halo$(C_1-C_6)$alkyl, $(C_1-C_6)$alkoxy, halo$(C_1-C_6)$alkoxy or cyano group, in the para-position;
R8 is a hydrogen atom or a $(C_1-C_6)$alkyl group;
Y is a hydrogen, a halogen, a $(C_1-C_6)$alkoxy group; a $(C_1-C_6)$alkyl group; a cyano; or a halo$(C_1-C_6)$alkyl group;
in the form of enantiomers or diastereoisomers or of mixtures of these forms;
in the form of a base or of an addition salt with an acid or with a base.

Among the compounds of formula (I) which are subjects of the invention, a second group of compounds comprises the compounds for which:
R' is an NR4R5 or OR8;
R is a methyl;
A and B, if they are present, are, independently of one another, a —CH$_2$—;
R1 is a hydrogen atom;
R2 and R3 are, independently of one another, a hydrogen atom or a $(C_1-C_6)$alkyl group; the $(C_1-C_6)$alkyl group being optionally substituted with a hydroxyl group;
R4 and R5 are, independently of one another, a hydrogen atom or a methyl, or form, together with the nitrogen atom which bears them, a morpholine;
R6 and R7 are each a phenyl group substituted with a chlorine, fluorine or bromine atom or a Me, OMe, CN, CF$_3$ or OCF$_3$ group, in the para-position;
R8 is a hydrogen atom or a $(C_1-C_6)$alkyl group;
Y is a hydrogen, a halogen, a $(C_1-C_6)$alkoxy group; a $(C_1-C_6)$alkyl group; a cyano; or a halo$(C_1-C_6)$alkyl group;
in the form of enantiomers or diastereoisomers or of mixtures of these forms;
in the form of a base or of an addition salt with an acid or with a base.

Among the compounds of formula (I) which are subjects of the invention, a third group of compounds comprises the compounds for which:
R' is an NR4R5 or OR8;
R is a methyl;
A and B, if they are present, are, independently of one another, a —CH$_2$—;
R1 is a hydrogen atom;
R2 and R3 are, independently of one another, a hydrogen atom or a $(C_1-C_6)$alkyl group; the $(C_1-C_6)$alkyl group being optionally substituted with a hydroxyl group;
R4 and R5 are, independently of one another, a hydrogen atom or a methyl, or form, together with the nitrogen atom which bears them, a morpholine,
R6 and R7 are each a phenyl group, optionally substituted with one or more atoms or groups chosen from a halogen, and a $(C_1-C_6)$alkyl, halo$(C_1-C_6)$alkyl, $(C_1-C_6)$alkoxy, halo$(C_1-C_6)$alkoxy or cyano group, in the para-position;

R8 is a hydrogen atom or a ($C_1$-$C_6$)alkyl group;
Y is a hydrogen, chlorine, fluorine or bromine atom or a Me, OMe, CN or $CF_3$ group;
in the form of enantiomers or diastereoisomers or of mixtures of these forms;
in the form of a base or of an addition salt with an acid or with a base.

Among the compounds of formula (I) which are subjects of the invention, a fourth group of compounds comprises the compounds for which:
R' is an NR4R5 or OR8;
R is a methyl;
A and B, if they are present, are, independently of one another, a —$CH_2$—;
R1 is a hydrogen atom;
R2 and R3 are, independently of one another, a hydrogen atom or a ($C_1$-$C_6$)alkyl group; the ($C_1$-$C_6$)alkyl group being optionally substituted with a hydroxyl group;
R4 and R5 are, independently of one another, a hydrogen atom or a methyl or form, together with the nitrogen atom which bears them, a morpholine;
R6 and R7 are each a phenyl group substituted with a chlorine, fluorine or bromine atom or a Me, OMe, CN, $CF_3$ or $OCF_3$ group, in the para-position;
R8 is a hydrogen atom or a ($C_1$-$C_6$)alkyl group;
Y is a hydrogen, chlorine, fluorine or bromine atom or a Me, OMe, CN or $CF_3$ group,
in the form of enantiomers or diastereoisomers or of mixtures of these forms;
in the form of a base or of an addition salt with an acid or with a base.

In the context of the present invention:
the term "a halogen" is intended to mean: a fluorine, a chlorine, a bromine or an iodine;
the term "a ($C_1$-$C_6$)alkyl group" is intended to mean: a cyclic, branched or linear, saturated aliphatic group which may optionally be substituted with a cyclic alkyl group. By way of examples, mention may be made of methyl, ethyl, propyl, isopropyl, butyl, isobutyl, tert-butyl, pentyl, hexyl, cyclopropyl, cyclobutyl, cyclopentyl, cyclohexyl, cycloheptyl, cyclopropylmethyl, etc., groups;
the term "a halo($C_1$-$C_6$)alkyl group" is intended to mean: a ($C_1$-$C_6$)alkyl group as defined above, one or more of the hydrogen atoms of which have been substituted with a halogen atom. By way of examples, mention may be made of $CF_3$, $CH_2CF_3$, $CHF_2$ or $CCl_3$ groups;
the term "a ($C_1$-$C_6$)alkoxy group" is intended to mean: an —O—($C_1$-$C_6$)alkyl group where the ($C_1$-$C_6$)alkyl group is as defined above;
the term "a halo($C_1$-$C_6$)alkoxy group" is intended to mean: a halo($C_1$-$C_6$)alkyl-O— group where the halo($C_1$-$C_6$) alkyl group is as defined above;
the term "an allyl group" is intended to mean a $CH_2$—CH=$CH_2$.

The compounds of formula (I) may exist in the form of bases or of acids or of salts. Such addition salts form part of the invention.

These salts may be prepared with pharmaceutically acceptable acids, but the salts of other acids that are of use, for example, for purifying or isolating the compounds of formula (I) also form part of the invention.

The compounds of formula (I) may also exist in the form of hydrates or of solvates, i.e. in the form of associations or combinations with one or more water molecules or with a solvent. Such hydrates and solvates also form part of the invention.

Among the compounds of formula (I) which are subjects of the invention, mention may in particular be made of the following compounds. The nomenclature used generally corresponds to the IUPAC nomenclature.

3-({1-[bis(4-chlorophenyl)methyl]azetidin-3-yl}methanesulphonylamino)-N—((S)-1-carbamoylethyl)benzamide 3-({1-[bis(4-chlorophenyl)methyl]azetidin-3-yl}methanesulphonylamino)-N-carbamoylmethyl-5-fluorobenzamide 3-({1-[bis(4-chlorophenyl)methyl]azetidin-3-yl}methanesulphonylamino)-N—((S)-1-carbamoylethyl)-5-fluorobenzamide 3-({1-[bis(4-chlorophenyl)methyl]azetidin-3-yl}methanesulphonylamino)-N—((R)-1-carbamoylethyl)-5-fluorobenzamide 3-({1-[bis(4-chlorophenyl)methyl]azetidin-3-yl}methanesulphonylamino)-N—((R)-1-carbamoylethyl)benzamide 3-({1-[bis(4-chlorophenyl)methyl]azetidin-3-yl}methanesulphonylamino)-N—((S)-1-carbamoyl-2-hydroxyethyl)benzamide 3-({1-[bis(4-chlorophenyl)methyl]azetidin-3-yl}methanesulphonylamino)-N-(2-carbamoylethyl)benzamide 3-({1-[bis(4-chlorophenyl)methyl]azetidin-3-yl}methanesulphonylamino)-N-(2-morpholin-4-yl-2-oxoethyl)benzamide 3-({1-[bis(4-chlorophenyl)methyl]azetidin-3-yl}methanesulphonylamino)-N—((S)-1-methylcarbamoylethyl)benzamide 3-({1-[bis(4-chlorophenyl)methyl]azetidin-3-yl}methanesulphonylamino)-N—((S)-1-carbamoylpropyl)benzamide 3-({1-[bis(4-chlorophenyl)methyl]azetidin-3-yl}methanesulphonylamino)-N—((S)-1-carbamoyl-3-methylbutyl)benzamide 3-({1-[bis(4-chlorophenyl)methyl]azetidin-3-yl}methanesulphonylamino)-N—((S)-1-carbamoyl-2-methylpropyl)-5-fluorobenzamide 3-({1-[bis(4-chlorophenyl)methyl]azetidin-3-yl}methanesulphonylamino)-N—((S)-1-carbamoyl-2-hydroxyethyl)-5-fluorobenzamide 3-({1-[bis(4-chlorophenyl)methyl]azetidin-3-yl}methanesulphonylamino)-N—((S)-1-carbamoylpropyl)-5-fluorobenzamide 3-({1-[bis(4-chlorophenyl)methyl]azetidin-3-yl}methanesulphonylamino)-N-(methylcarbamoylmethyl)benzamide 3-({1-[bis(4-chlorophenyl)methyl]azetidin-3-yl}methanesulphonylamino)-N-(carbamoylmethyl)benzamide (S)-2-[3-({1-[bis(4-chlorophenyl)methyl]azetidin-3-yl}methanesulphonylamino)benzoylamino]propionic acid tert-butyl ester (S)-2-[3-({1-[bis(4-chlorophenyl)methyl]azetidin-3-yl}methanesulphonylamino)benzoylamino]propionic acid 3-({1-[bis(4-chlorophenyl)methyl]azetidin-3-yl}methanesulphonylamino)benzoylaminoacetic acid tert-butyl ester 4-[3-({1-[bis(4-chlorophenyl)methyl]azetidin-3-yl}methanesulphonylamino)-5-fluorobenzoylamino]butyric acid tert-butyl ester (S)-2-[3-({1-[bis(4-chlorophenyl)methyl]azetidin-3-yl}methanesulphonylamino)-5-fluorobenzoylamino]propionic acid tert-butyl ester

- 3-({1-[bis(4-chlorophenyl)methyl]azetidin-3-yl}methanesulphonylamino)-N—((S)-1-carbamoyl-ethyl)-5-methoxybenzamide
- 3-({1-[bis(4-chlorophenyl)methyl]azetidin-3-yl}methanesulphonylamino)-N—((S)-1-dimethylcarbamoylethyl)benzamide
- 4-[3-({1-[bis(4-chlorophenyl)methyl]azetidin-3-yl}methanesulphonylamino)benzoylamino]butyric acid tert-butyl ester
- (S)-2-[3-({1-[bis(4-chlorophenyl)methyl]azetidin-3-yl}methanesulphonylamino)-5-fluorobenzoylamino]propionic acid and the sodium salt thereof
- 3-({1-[bis(4-chlorophenyl)methyl]azetidin-3-yl}methanesulphonylamino)-5-fluoro-N—((S)-1-methylcarbamoylethyl)benzamide
- 3-({1-[bis(4-chlorophenyl)methyl]azetidin-3-yl}methanesulphonylamino)-N-((1S,2R)-1-carbamoyl-2-hydroxypropyl)benzamide
- 3-({1-[bis(4-chlorophenyl)methyl]azetidin-3-yl}methanesulphonylamino)-N-(3-carbamoylpropyl)-5-fluorobenzamide
- [3-({1-[bis(4-chlorophenyl)methyl]azetidin-3-yl}methanesulphonylamino)benzoylamino]acetic acid
- 3-({1-[bis(4-chlorophenyl)methyl]azetidin-3-yl}methanesulphonylamino)-N—((S)-1-carbamoyl-ethyl)-2-fluorobenzamide
- 3-({1-[bis(4-chlorophenyl)methyl]azetidin-3-yl}methanesulphonylamino)-N—((S)-1-methylcarbamoylethyl)-2-fluorobenzamide
- 3-({1-[bis(4-chlorophenyl)methyl]azetidin-3-yl}methanesulphonylamino)-N—((S)-1-carbamoyl-ethyl)-6-fluorobenzamide
- 3-({1-[bis(4-chlorophenyl)methyl]azetidin-3-yl}methanesulphonylamino)-N—((S)-1-carbamoylpropyl)-6-fluorobenzamide
- 3-({1-[bis(4-chlorophenyl)methyl]azetidin-3-yl}methanesulphonylamino)-N—((S)-1-carbamoyl-2-methylpropyl)-6-fluorobenzamide
- 3-({1-[bis(4-chlorophenyl)methyl]azetidin-3-yl}methanesulphonylamino)-N—((S)-1-methylcarbamoylethyl)-6-fluorobenzamide
- 3-({1-[bis(4-chlorophenyl)methyl]azetidin-3-yl}methanesulphonylamino)-N—((S)-1-carbamoylpropyl)-4-fluorobenzamide
- 3-({1-[bis(4-chlorophenyl)methyl]azetidin-3-yl}methanesulphonylamino)-N-carbamoylmethyl-5-methylbenzamide
- 3-({1-[bis(4-chlorophenyl)methyl]azetidin-3-yl}methanesulphonylamino)-N—((S)-1-carbamoyl-ethyl)-5-methylbenzamide
- 3-({1-[bis(4-chlorophenyl)methyl]azetidin-3-yl}methanesulphonylamino)-N—((S)-1-carbamoylpropyl)-5-methylbenzamide
- 3-({1-[bis(4-chlorophenyl)methyl]azetidin-3-yl}methanesulphonylamino)-N—((S)-1-carbamoyl-2-methylpropyl)-5-methylbenzamide
- 3-({1-[bis(4-chlorophenyl)methyl]azetidin-3-yl}methanesulphonylamino)-N—((S)-1-methylcarbamoylethyl)-5-methylbenzamide
- 3-({1-[bis(4-chlorophenyl)methyl]azetidin-3-yl}methanesulphonylamino)-N—((S)-1-carbamoyl-2-hydroxyethyl)-5-methylbenzamide
- 3-({1-[bis(4-chlorophenyl)methyl]azetidin-3-yl}methanesulphonylamino)-N—((S)-1-carbamoyl-ethyl)-5-chlorobenzamide
- 3-({1-[bis(4-chlorophenyl)methyl]azetidin-3-yl}methanesulphonylamino)-N—((S)-1-carbamoylpropyl)-5-chlorobenzamide
- 3-({1-[bis(4-chlorophenyl)methyl]azetidin-3-yl}methanesulphonylamino)-N—((S)-1-carbamoyl-2-methylpropyl)-5-chlorobenzamide
- 3-({1-[bis(4-chlorophenyl)methyl]azetidin-3-yl}methanesulphonylamino)-N—((S)-1-methylcarbamoylethyl)-5-chlorobenzamide
- 3-({1-[bis(4-chlorophenyl)methyl]azetidin-3-yl}methanesulphonylamino)-N—((S)-1-carbamoyl-2-hydroxyethyl)-5-chlorobenzamide
- 3-({1-[bis(4-chlorophenyl)methyl]azetidin-3-yl}methanesulphonylamino)-N—((S)-1-carbamoyl-ethyl)-5-bromobenzamide
- 3-({1-[bis(4-chlorophenyl)methyl]azetidin-3-yl}methanesulphonylamino)-N—((S)-1-carbamoylpropyl)-5-bromobenzamide
- 3-({1-[bis(4-chlorophenyl)methyl]azetidin-3-yl}methanesulphonylamino)-N—((S)-1-carbamoyl-2-methylpropyl)-5-bromobenzamide
- 3-({1-[bis(4-chlorophenyl)methyl]azetidin-3-yl}methanesulphonylamino)-N—((S)-1-methylcarbamoylethyl)-5-bromobenzamide
- 3-({1-[bis(4-chlorophenyl)methyl]azetidin-3-yl}methanesulphonylamino)-N—((S)-1-carbamoyl-2-hydroxyethyl)-5-bromobenzamide
- 3-({1-[bis(4-chlorophenyl)methyl]azetidin-3-yl}methanesulphonylamino)-N-carbamoylmethyl-5-trifluoromethylbenzamide
- 3-({1-[bis(4-chlorophenyl)methyl]azetidin-3-yl}methanesulphonylamino)-N—((S)-1-carbamoyl-ethyl)-5-trifluoromethylbenzamide
- 3-({1-[bis(4-chlorophenyl)methyl]azetidin-3-yl}methanesulphonylamino)-N—((S)-1-carbamoylpropyl)-5-trifluoromethylbenzamide
- 3-({1-[bis(4-chlorophenyl)methyl]azetidin-3-yl}methanesulphonylamino)-N—((S)-1-carbamoyl-2-methylpropyl)-5-trifluoromethylbenzamide
- 3-({1-[bis(4-chlorophenyl)methyl]azetidin-3-yl}methanesulphonylamino)-N—((S)-1-methylcarbamoylethyl)-5-trifluoromethylbenzamide
- 3-({1-[bis(4-chlorophenyl)methyl]azetidin-3-yl}methanesulphonylamino)-N—((S)-1-carbamoyl-2-hydroxyethyl)-5-trifluoromethylbenzamide
- 3-({1-[bis(4-chlorophenyl)methyl]azetidin-3-yl}methanesulphonylamino)-N—((S)-1-carbamoyl-ethyl)-5-cyanobenzamide
- 3-({1-[bis(4-chlorophenyl)methyl]azetidin-3-yl}methanesulphonylamino)-N—((S)-1-carbamoylpropyl)-5-cyanobenzamide
- 3-({1-[bis(4-chlorophenyl)methyl]azetidin-3-yl}methanesulphonylamino)-N—((S)-1-carbamoyl-2-methylpropyl)-5-cyanobenzamide
- 3-({1-[bis(4-chlorophenyl)methyl]azetidin-3-yl}methanesulphonylamino)-N—((S)-1-methylcarbamoylethyl)-5-cyanobenzamide
- 3-({1-[bis(4-chlorophenyl)methyl]azetidin-3-yl}methanesulphonylamino)-N—((S)-1-carbamoyl-2-hydroxyethyl)-5-cyanobenzamide
- (S)-2-[3-({1-[bis(4-chlorophenyl)methyl]azetidin-3-yl}methanesulphonylamino)-6-fluorobenzoylamino]propionic acid and the trifluoroacetic acid salt thereof.
- (S)-2-[3-({1-[bis(4-chlorophenyl)methyl]azetidin-3-yl}methanesulphonylamino)-5-methylbenzoylamino]propionic acid and the trifluoroacetic acid salt thereof.

(S)-2-[3-({1-[bis(4-chlorophenyl)methyl]azetidin-3-yl}methanesulphonylamino)-5-chlorobenzoylamino]propionic acid and the trifluoroacetic acid salt thereof.

(S)-2-[3-({1-[bis(4-chlorophenyl)methyl]azetidin-3-yl}methanesulphonylamino)-5-bromobenzoylamino]propionic acid and the trifluoroacetic acid salt thereof.

(S)-2-[3-({1-[bis(4-chlorophenyl)methyl]azetidin-3-yl}methanesulphonylamino)-3-trifluoromethylbenzoylamino]propionic acid and the trifluoroacetic acid salt thereof.

(S)-2-[3-({1-[bis(4-chlorophenyl)methyl]azetidin-3-yl}methanesulphonylamino)-5-cyanobenzoylamino]propionic acid and the trifluoroacetic acid salt thereof 3-({1-[bis(4-bromophenyl)methyl]azetidin-3-yl}methanesulphonylamino)-N—((S)-1-carbamoylethyl)-5-fluorobenzamide 3-({1-[bis(4-trifluoromethylphenyl)methyl]azetidin-3-yl}methanesulphonylamino)-N—((S)-1-carbamoylethyl)-5-fluorobenzamide 3-({1-[bis(4-cyanophenyl)methyl]azetidin-3-yl}methanesulphonylamino)-N—((S)-1-carbamoylethyl)-5-fluorobenzamide 3-({1-[bis(4-methoxyphenyl)methyl]azetidin-3-yl}methanesulphonylamino)-N—((S)-1-carbamoylethyl)-5-fluorobenzamide 3-({1-[bis(4-fluorophenyl)methyl]azetidin-3-yl}methanesulphonylamino)-N—((S)-1-carbamoylethyl)-5-fluorobenzamide (S)-2-[3-({1-[bis(4-chlorophenyl)methyl]azetidin-3-yl}methanesulphonylamino)-5-fluorobenzoylamino]propionic acid methyl ester 3-({1-[bis(4-methylphenyl)methyl]azetidin-3-yl}methanesulphonylamino)-N—((S)-1-carbamoylpropyl)-5-fluorobenzamide 3-({1-[bis(4-bromophenyl)methyl]azetidin-3-yl}methanesulphonylamino)-N—((S)-1-methylcarbamoylethyl)-5-fluorobenzamide (S)-2-[3-({1-[bis(4-bromophenyl)methyl]azetidin-3-yl}methanesulphonylamino)-5-fluorobenzoylamino]propionic acid (S)-2-[3-({1-[bis(4-chlorophenyl)methyl]azetidin-3-yl}methanesulphonylamino)-5-fluorobenzoylamino]propionic acid ethyl ester and 3-({1-[bis(4-trifluoromethoxyphenyl)methyl]azetidin-3-yl}methanesulphonylamino)-N—((S)-1-carbamoylpropyl)-5-fluorobenzamide the optical isomers thereof and the pharmaceutically acceptable salts thereof.

A subject of the present invention is also the use of the compounds of the invention of formula (I), for the preparation of a medicament for the treatment or prevention of diseases in which the CB1 receptor is involved.

A subject of the present invention is also the use of the compounds of the invention of formula (I), for the preparation of a medicament for the treatment or prevention of psychiatric disorders, substance dependence and withdrawal, tobacco withdrawal, cognitive and attention disorders and acute and chronic neurodegenerative diseases; the metabolism, appetence disorders, appetite disorders, obesity, diabetes, (type I and/or II), metabolic syndrome, dyslipidemia, sleep apnoea; pain, neuropathic pain, neuropathic pain induced by anticancer drugs; gastrointestinal disorders, vomiting, ulcers, diarrhoea disorders, bladder and urinary disorders, disorders of endocrine origin, cardiovascular disorders, hypotension, haemorrhagic shock, septic shock, liver diseases, chronic liver cirrhosis, fibrosis, non-alcoholic steatohepatitis (NASH), steatohepatitis and hepatic steatosis, irrespective of the etiology of these conditions (alcohol, medicament, chemical product, autoimmune disease, obesity, diabetes, congenital metabolic disease); immune system diseases, rheumatoid arthritis, demyelination, multiple sclerosis, inflammatory diseases; Alzheimer's disease, Parkinson's disease, schizophrenia, cognitive disorders associated with schizophrenia, with diabetes, with obesity or with metabolic syndrome; asthma, chronic obstructive pulmonary diseases, Raynaud's syndrome, glaucoma, fertility disorders; infectious and viral diseases such as encephalitis, cerebral strokes, Guillain-Barré syndrome, osteoporosis and sleep apnoea, and for anticancer chemotherapy; disorders related to antipsychotic treatments (weight gain, metabolic disorders).

In accordance with the invention, the compounds of general formula (I) can be prepared according to the process described in scheme 1:

Scheme 1
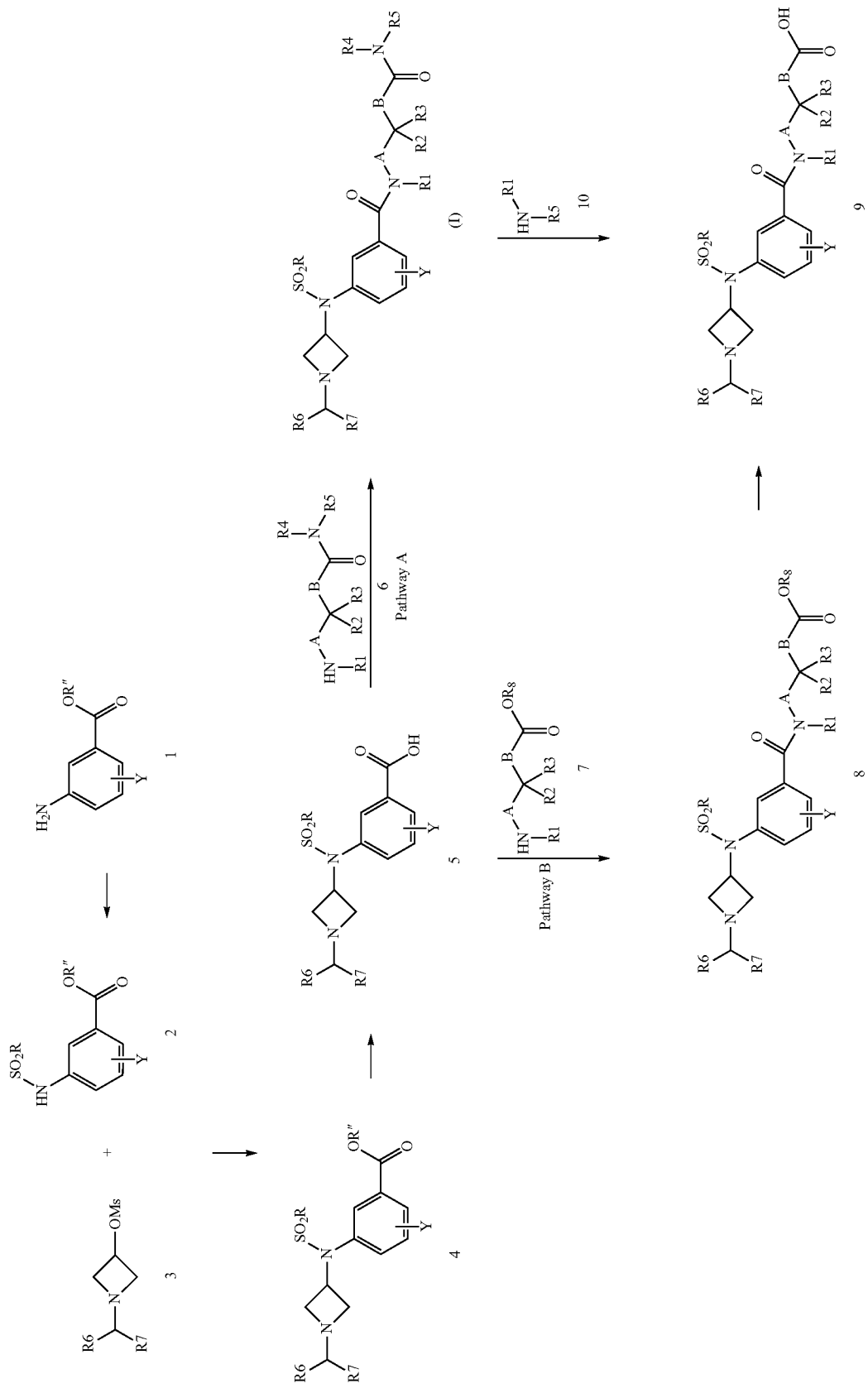

The mesylation of compound 1 to derivative 2 can be carried out according to the methods known to those skilled in the art or as described in T. W. GREENE, Protective Group in Organic Synthesis, third edition. This reaction can be carried out in a chlorinated solvent such as dichloromethane, in the presence of a base such as pyridine and of a mesylate derivative such as mesyl chloride, at a temperature of between −10° C. and 40° C.

The derivatives 1 are commercially available or synthesized, according to the methods known to those skilled in the art, from the appropriate commercially available precursors; R″ is an R8 group with the exception of the hydrogen atom.

Derivative 4 can be obtained by reacting the mesylate 2 with the azetidine 3. This step is preferably carried out under an inert atmosphere, in an inert solvent such as 4-methyl-2-pentanone, in the presence of an inorganic base such as potassium carbonate, at the reflux of the reaction mixture.

The synthesis of the azetidine 3 is described in patent application WO 01064634.

The hydrolysis of the ester 4 to acid 5 is carried out according to the methods known to those skilled in the art, and more specifically in a mixture of polar solvents such as tetrahydrofuran and water in the presence of a base such as lithium hydroxide hydrate at a temperature in the region of 20° C.

The formation of the compounds of formula (I) can be carried out, according to pathway A, by reaction between the acid 5 and an amino derivative 6. This reaction can be carried out in an inert solvent such as tetrahydrofuran or a chlorinated solvent (dichloromethane, for example), in the presence or absence of a base such as a trialkylamine (triethylamine, for example), and of a coupling agent such as 1-(3-dimethylaminopropyl)-3-ethylcarbodiimide hydrochloride, in the presence or absence of an additive for preventing any racemization, such as 1-hydroxybenzo-triazole, and in the presence or absence of an agent for promoting peptide synthesis via the formation of a mixed anhydride such as isobutyl chloroformate, at a temperature of between −20° C. and the boiling point of the solvent. This reaction may also be carried out in an inert solvent, in the presence of a coupling agent and optionally of an additive for preventing racemization, the isolated product being optionally converted to an addition salt with an acid.

The derivatives 6 are commercially available or synthesized, according to the methods known to those skilled in the art, from the appropriate commercially available precursors.

The formation of the compounds of formula 8 can be carried out, according to pathway B, by reaction between the acid 5 and an amino derivative 7. This reaction can be carried out according to the conditions described above for obtaining the compounds of formula (I) from the acid 5 and the amino derivative 6.

The derivatives 7 are commercially available or synthesized, according to the methods known to those skilled in the art, from the appropriate commercially available precursors.

The hydrolysis of the ester 8 to acid 9 is carried out according to the methods known to those skilled in the art.

The formation of the compounds of formula (I) can be carried out by reaction between the acid 9 and an amine 10. This reaction can be carried out according to the conditions described above for obtaining the compounds of formula (I) from the acid 5 and the amino derivative 6.

The derivatives 10 are commercially available or synthesized, according to the methods known to those skilled in the art, from the appropriate commercially available precursors.

The compounds of formula (I) may be converted to other compounds of formula (I) by changing the CHR6R7 group by debenzhydrylation using methods known to those skilled in the art, followed by alkylation with a CHXR6R7 group in the presence of a base, X being a leaving group (for example a halogen).

The compounds of formula (I) may be purified by the customary known methods, for example by crystallization, chromatography or extraction.

The enantiomers of the compounds of formula (I) may be obtained by resolving the racemic mixtures, for example by chromatography on a chiral column according to W. H. PIRKLE et al., Asymmetric Synthesis, Vol. 1, Academic Press (1983) or by formation of salts or by synthesis from the chiral precursors. The diastereoisomers may be prepared according to the customary known methods (crystallization, chromatography, or from the chiral precursors).

The present invention also relates to the process for preparing the intermediates.

According to another of its aspects, a subject of the invention is also the compounds of formulae 4 and 5. These compounds are useful as intermediates for synthesizing the compounds of formula (I).

The intermediates useful for the synthesis of the compounds of formula (I) are illustrated in a nonlimiting manner below:

3-({1-[bis(4-chlorophenyl)methyl]azetidin-3-yl}methanesulphonylamino)-5-fluorobenzoic acid methyl ester 3-({1-[bis(4-fluorophenyl)methyl]azetidin-3-yl}methanesulphonylamino)-5-fluorobenzoic acid methyl ester 3-({1-[bis(4-fluorophenyl)methyl]azetidin-3-yl}methanesulphonylamino)-5-fluorobenzoic acid 3-({1-[bis(4-bromophenyl)methyl]azetidin-3-yl}methanesulphonylamino)-5-fluorobenzoic acid ethyl ester 3-({1-[bis(4-bromophenyl)methyl]azetidin-3-yl}methanesulphonylamino)-5-fluorobenzoic acid 3-({1-[bis(4-trifluoromethylphenyl)methyl]azetidin-3-yl}methanesulphonylamino)-5-fluorobenzoic acid ethyl ester 3-({1-[bis(4-trifluoromethylphenyl)methyl]azetidin-3-yl}methanesulphonylamino)-5-fluorobenzoic acid 3-({1-[bis(4-methoxyphenyl)methyl]azetidin-3-yl}methanesulphonylamino)-5-fluorobenzoic acid ethyl ester 3-({1-[bis(4-methoxyphenyl)methyl]azetidin-3-yl}methanesulphonylamino)-5-fluorobenzoic acid 3-({1-[bis(4-methylphenyl)methyl]azetidin-3-yl}methanesulphonylamino)-5-fluorobenzoic acid methyl ester 3-({1-[bis(4-methylphenyl)methyl]azetidin-3-yl}methanesulphonylamino)-5-fluorobenzoic acid 3-({1-[bis(4-cyanophenyl)methyl]azetidin-3-yl}methanesulphonylamino)-5-fluorobenzoic acid ethyl ester 3-({1-[bis(4-cyanophenyl)methyl]azetidin-3-yl}methanesulphonylamino)-5-fluorobenzoic acid 3-({1-[bis(4-trifluoromethoxyphenyl)methyl]azetidin-3-yl}methanesulphonylamino)-5-fluorobenzoic acid methyl ester 3-({1-[bis(4-trifluoromethoxyphenyl)methyl]azetidin-3-yl}methanesulphonylamino)-5-fluorobenzoic acid 3-({1-[bis(4-chlorophenyl)methyl]azetidin-3-yl}methanesulphonylamino)-2-fluorobenzoic acid methyl ester 3-({1-[bis(4-chlorophenyl)methyl]azetidin-3-yl}methanesulphonylamino)-2-fluorobenzoic acid 3-({1-[bis(4-chlorophenyl)methyl]azetidin-3-yl}methanesulphonylamino)-4-fluorobenzoic acid ethyl ester 3-({1-[bis(4-chlorophenyl)methyl]azetidin-3-yl}methanesulphonylamino)-4-fluorobenzoic acid 3-({1-[bis(4-chlorophenyl)methyl]azetidin-3-yl}methanesulphonylamino)-6-fluorobenzoic acid methyl ester 3-({1-[bis(4-chlorophenyl)methyl]azetidin-3-yl}methanesulphonylamino)-6-fluorobenzoic acid 3-({1-[bis(4-chlorophenyl)methyl]azetidin-3-yl}methanesulphonylamino)-5-methoxybenzoic acid methyl ester 3-({1-[bis(4-chlorophenyl)methyl]azetidin-3-yl}methanesulphonylamino)-5-methoxybenzoic acid 3-({1-[bis(4-chlorophenyl)methyl]azetidin-3-yl}methanesulphonylamino)-5-methylbenzoic acid allyl ester 3-({1-[bis(4-chlorophenyl)methyl]azetidin-3-yl}methanesulphonylamino)-5-methylbenzoic acid 3-({1-[bis(4-chlorophenyl)methyl]azetidin-3-yl}methanesulphonylamino)-5-chlorobenzoic acid methyl ester 3-({1-[bis(4-chlorophenyl)methyl]azetidin-3-yl}methanesulphonylamino)-5-chlorobenzoic acid 3-({1-[bis(4-chlorophenyl)methyl]azetidin-3-yl}methanesulphonylamino)-5-bromobenzoic acid methyl ester 3-({1-[bis(4-chlorophenyl)methyl]azetidin-3-yl}methanesulphonylamino)-5-bromobenzoic acid 3-({1-[bis(4-chlorophenyl)methyl]azetidin-3-yl}methanesulphonylamino)-5-trifluoromethylbenzoic acid methyl ester 3-({1-[bis(4-chlorophenyl)methyl]azetidin-3-yl}methanesulphonylamino)-5-trifluoromethylbenzoic acid 3-({1-[bis(4-chlorophenyl)methyl]azetidin-3-yl}methanesulphonylamino)-5-cyanobenzoic acid methyl ester and 3-({1-[bis(4-chlorophenyl)methyl]azetidin-3-yl}methanesulphonylamino)-5-cyanobenzoic acid The compounds of formulae 4 and 5 were prepared in the form of a powder or an oil, in the form of a base. Table 1A gives some physicochemical data for these intermediates.

TABLE 1A

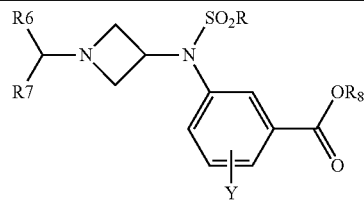

| R6 | R7 | Y | R" | NMR |
|---|---|---|---|---|
| 4-Cl—Ph | 4-Cl—Ph | 5-F | Me | 1H NMR (400 MHz, DMSO-d6) δ (ppm) 2.75 (m, 2 H) 3.01 (s, 3 H) 3.38 (m, 2 H) 3.89 (s, 3 H) 4.44 (s, 1H) 4.80 (m, 1 H) 7.32 (d, J = 8.7 Hz, 4 H) 7.38 (d, J = 8.7 Hz, 4 H) 7.59 (dt, J = 9.5, 2.1 Hz, 1 H) 7.69 (ddd, J = 8.5, 2.1, 1.6 Hz, 1 H) 7.74 (broad s, 1 H) |
| 4-F—Ph | 4-F—Ph | 5-F | Me | 1H NMR (400 MHz, DMSO-d6) δ (ppm) 2.71 (m, 2 H) 2.98 (s, 3 H) 3.33 (m, 2 H) 3.87 (s, 3 H) 4.41 (s, 1H) 4.76 (m, 1 H) 7.07 (t, J = 8.9 Hz, 4 H) 7.37 (dd, J = 8.9, 5.6 Hz, 4 H) 7.56 (dt, J = 9.5, 2.0 Hz, 1 H) 7.67 (ddd, J = 7.8, 2.0, 1.4 Hz, 1 H) 7.70 (broad s, 1 H) |
| 4-F—Ph | 4-F—Ph | 5-F | H | 1H NMR (400 MHz, DMSO-d6) δ (ppm): 3.02 (m, 3 H) 3.39-3.57 (m partially masked, 2 H) 3.72-4.36 (m, 2 H) 5.00-5.40 (m, 1 H) 5.80-6.10 (m, 1 H) 6.90-7.80 (m, 11 H) 12.00-12.67 (m, 1 H) 13.56 (m, 1 H) |
| 4-Br—Ph | 4-Br—Ph | 5-F | Et | 1H NMR (400 MHz, DMSO-d6) δ (ppm) 1.32 (t, J = 7.1 Hz, 3 H) 2.73 (m, 2 H) 2.98 (s, 3 H) 3.35 (m, 2 H) 4.34 (q, J = 7.1 Hz, 2 H) 4.40 (s, 1 H) 4.76 (m, 1 H) 7.30 (d, J = 8.7 Hz, 4 H) 7.45 (d, J = 8.7 Hz, 4 H) 7.56 (dt, J = 9.5, 2.3 Hz, 1 H) 7.66 (ddd, J = 8.8, 2.3, 1.1 Hz, 1 H) 7.70 (broad s, 1 H) |
| 4-Br—Ph | 4-Br—Ph | 5-F | H | 1H NMR (400 MHz, DMSO-d6) δ (ppm) 2.73 (m, 2 H) 2.97 (s, 3 H) 3.34 (m partially masked, 2 H) 4 40 (s, 1 H) 4.75 (m, 1 H) 7.30 (d, J = 8.5 Hz, 4 H) 7.44 (d, J = 8.5 Hz, 4 H) 7.47 (m partially masked, 1H) 7.62 (broad d, J = 9.0 Hz, 1 H) 7.68 (broad s, 1 H) 12.95 (broad m, 1 H) |
| 4-CF3—Ph | 4-CF3—Ph | 5-F | Et | 1H NMR (400 MHz, DMSO-d6) δ (ppm) 1.32 (t, J = 7.1 Hz, 3 H) 2.81 (m, 2 H) 2.99 (s, 3 H) 3.41 (m, 2 H) 4.34 (q, J = 7.1 Hz, 2 H) 4.69 (s, 1 H) 4.81 1 H) 7.57 (dt, J = 9.5, 2.2 Hz, 1 H) 7.60-7.68 (m, 9 H) 7.71 (broad s, 1 H) |
| 4-CF3—Ph | 4-CF3—Ph | 5-F | H | 1H NMR (400 MHz, DMSO-d6) δ (ppm) 2.81 (m, 2 H) 2.99 (s, 3 H) 3.40 (m, 2 H) 4.68 (s, 1 H) 4.81 (m, 1H) 7.51 (dt, J = 9.5, 2.3 Hz, 1 H) 7.58-7.66 (m, 9 H) 7.71 (broad s, 1 H) 13.39 (broad m, 1 H) |

TABLE 1A-continued

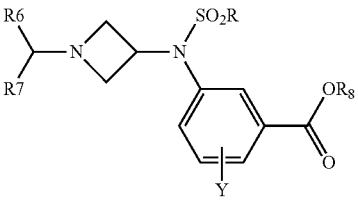

| R6 | R7 | Y | R" | NMR |
|---|---|---|---|---|
| 4-OCH₃—Ph | 4-OCH₃—Ph | 5-F | Et | 1H NMR (400 MHz, DMSO-d6) δ (ppm) 1.33 (t, J = 7.1 Hz, 3 H) 2.67 (m, 2 H) 2.98 (s, 3 H) 3.31 (m partially masked, 2 H) 3.67 (s, 6 H) 4.22 (s, 1 H) 4.34 (q, J = 7.1 Hz, 2 H) 4.73 (m, 1 H) 6.79 (d, J = 8.8 Hz, 4 H) 7.23 (d, J = 8.8 Hz, 4 H) 7.56 (dt, J = 9.5, 2.3 Hz, 1 H) 7.66 (ddd, J = 8.6, 2.3, 1.6 Hz, 1 H) 7.70 (broad s, 1 H) |
| 4-OCH₃—Ph | 4-OCH₃—Ph | 5-F | H | 1H NMR (400 MHz, DMSO-d6) δ (ppm) 2.66 (m, 2 H) 2.96 (s, 3 H) 3.18-3.34 (m partially masked, 2 H) 3.67 (s, 6 H) 4.20 (s, 1 H) 4.71 (m, 1 H) 6.79 (d, J = 8.8 Hz, 4 H) 7.22 (d, J = 8.8 Hz, 4 H) 7.43 (broad d, J = 9.5 Hz, 1 H) 7.60 (broad d, J = 9.0 Hz, 1 H) 7.66 (broad s, 1 H) 13.52 (broad m, 1 H) |
| 4-CH₃—Ph | 4-CH₃—Ph | 5-F | Me | 1H NMR (400 MHz, DMSO-d6) δ (ppm) 2.20 (s, 6 H) 2.67 (m, 2 H) 2.97 (s, 3 H) 3.32 (m, 2 H) 3.87 (s, 3H) 4.24 (s, 1 H) 4.74 (m, 1 H) 7.03 (d, J = 8.1 Hz, 4 H) 7.20 (d, J = 8.1 Hz, 4 H) 7.55 (dt, J = 9.6, 2.2 Hz, 1 H) 7.67 (ddd, J = 8.0, 2.2, 1.7 Hz, 1 H) 7.70 (broad s, 1 H) |
| 4-CH₃—Ph | 4-CH₃—Ph | 5-F | H | 1H NMR (400 MHz, DMSO-d6) δ (ppm) 2.20 (s, 6 H) 2.68 (m, 2 H) 2.97 (s, 3 H) 3.32 (m, 2 H) 4.24 (s, 1H) 4.73 (m, 1 H) 7.03 (d, J = 8.1 Hz, 4 H) 7.20 (d, J = 8.1 Hz, 4 H) 7.50 (dt, J = 9.5, 2.3 Hz, 1 H) 7.62 (ddd, J = 8.8, 2.3, 1.5 Hz, 1 H) 7.68 (broad s, 1 H) 13.52 (broad m, 1 H) |
| 4-CN—Ph | 4-CN—Ph | 5-F | Et | 1H NMR (400 MHz, DMSO-d6) δ (ppm) 1.32 (t, J = 7.1 Hz, 3 H) 2.78 (m, 2 H) 2.99 (s, 3 H) 3.38 (m, 2 H) 4.34 (q, J = 7.1 Hz, 2 H) 4.68 (s, 1 H) 4.80 (m, 1 H) 7.56 (m partially masked, 1 H) 7.58 (d, J = 8.5 Hz, 4H) 7.66 (broad d, J = 8.8 Hz, 1 H) 7.70 (broad s, 1 H) 7.74 (d, J = 8.5 Hz, 4 H) |
| 4-CN—Ph | 4-CN—Ph | 5-F | H | 1H NMR (400 MHz, DMSO-d6) δ (ppm) after addition of a drop of deuterated trifluoroacetic acid CF3CO2D-d) 3.03 (s, 3 H) 4.07 (m, 2 H) 4.24 (m, 2 H) 5.15 (m, 1 H) 6.07 (s, 1 H) 7.53 (dt, J = 9.3, 2.3 Hz, 1 H) 7.63 (d, J = 8.7 Hz, 4 H) 7.68 (ddd, J = 8.7, 2.3, 1.5 Hz, 1 H) 7.78 (broad s, 1 H) 7.88 (d, J = 8.7 Hz, 4 H) |
| 4-OCF₃—Ph | 4-OCF₃—Ph | 5-F | Me | 1H NMR (400 MHz, DMSO-d6) δ (ppm) 2.76 (m, 2 H) 2.99 (s, 3 H) 3.36 (m, 2 H) 3.87 (s, 3 H) 4.53 (s, 1H) 4.78 (m, 1 H) 7.26 (broad d, J = 8.8 Hz, 4 H) 7.49 (d, J = 8.8 Hz, 4 H) 7.56 (dt, J = 9.5, 2.3 Hz, 1 H) 7.67 (ddd, J = 8.6, 2.5, 1.3 Hz, 1 H) 7.71 (broad s, 1 H) |
| 4-OCF₃—Ph | 4-OCF₃—Ph | 5-F | H | 1H NMR (400 MHz, DMSO-d6) δ (ppm) 2.76 (m, 2 H) 2.98 (s, 3 H) 3.36 (m, 2 H) 4.53 (s, 1 H) 4.77 (m, 1H) 7.26 (broad d, J = 8.8 Hz, 4H) 7.49 (d, J = 8.8 Hz, 4 H) 7.51 (m partially masked, 1 H) 7.63 (ddd, J = 8.7, 2.6, 1.3 Hz, 1 H) 7.70 (broad s, 1 H) 13.53 (broad m, 1 H) |
| 4-Cl—Ph | 4-Cl—Ph | 2-F | Me | 1H-NMR (300 MHz, DMSO-d6): δ (ppm) =7.96-7.90 (m, 1H), 7.78-7.72 (m, 1H), 7.42-7.37 (m, 1H), 7.33-7.27 (m, 8H), 4.74-4.70 (m, 1H), 4.31 (s, 1H), 3.86 (s, 3H), 3.37-3.32 (m, 2H), 3.09 (s, 3H), 2.67-2.63(m, 2H) |
| 4-Cl—Ph | 4-Cl—Ph | 2-F | H | 1H NMR (500 MHz, DMSO-d6) δ (ppm) for this batch, all the signals are broad with: 3.06-4.27 (m, 4H) 3.13 (s, 3 H) 4.80-6.18 (m, 2 H) 7.26-7.86 (m, 10 H) 7.94 (m, 1 H) 12.37-13.89 (m, 1H) |
| 4-Cl—Ph | 4-Cl—Ph | 4-F | Et | 1H-NMR (300 MHz, DMSO-d6): δ (ppm) = 8.07-8.02 (m, 1H), 8.01-7.97 (m, 1H), 7.51 (t, J = 9.7, 1H), 7.34-7.27 (m, 8H), 4.76-4.72 (m, 1H), 4.37-4.30 (m, 3H), 3.35-3.32 (m, 2H), 3.10 (s, 3H), 2.74-2.66 (m, 2H), 1.33 (t, J = 7.1, 3H) |
| 4-Cl—Ph | 4-Cl—Ph | 4-F | H | 1H NMR (500 MHz, DMSO-d6) δ (ppm) with: 2.62-4.36 (m, 4H) 3.12 (s, 3 H) 4.65-6.28 (m, 2 H) 7.12-7.77 (m, 9 H) 8.06 (m, 2 H) 12.23-14.18 (m, 1H) |

TABLE 1A-continued

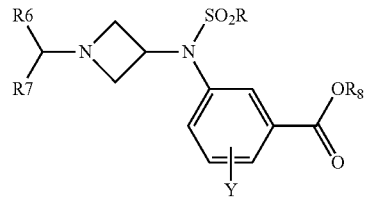

| R6 | R7 | Y | R" | NMR |
|---|---|---|---|---|
| 4-Cl—Ph | 4-Cl—Ph | 6-F | Me | 1H-NMR (300 MHz, DMSO-d6): δ (ppm) = 7.79-7.76 (m, 1H), 7.64-7.60 (m, 1H), 7.43-7.29 (m, 9H), 4.76-4.72 (m, 1H), 4.41 (s, 1H), 3.86 (s, 3H), 3.33-3.29 (m, 2H), 2.96 (s, 3H), 2.72 (t, J = 7.4, 2H). |
| 4-Cl—Ph | 4-Cl—Ph | 6-F | H | 1H NMR (500 MHz, DMSO-d6) δ (ppm): 2.74-4.29 (m, 4H) 3.01 (s, 3 H) 4.75-6.30 (m, 2 H) 7.23-8.11 (m, 11 H) 11.79-14.10 (m, 1 H) |
| 4-Cl—Ph | 4-Cl—Ph | 5-OCH$_3$ | Me | 1H NMR (400 MHz, DMSO-d6) δ (ppm) 2.70 (m, 2 H) 2.95 (s, 3 H) 3.33 (m, 2 H) 3.82 (s, 3 H) 3.86 (s, 3H) 4.42 (s, 1 H) 4.76 (m, 1 H) 7.16 (t, J = 2.3 Hz, 1 H) 7.31 (d, J = 8.5 Hz, 4 H) 7.37 (d, J = 8.5 Hz, 4 H) 7.40 (t, J = 2.3 Hz, 1 H) 7.44 (t, J = 2.3 Hz, 1 H) |
| 4-Cl—Ph | 4-Cl—Ph | 5-OCH$_3$ | H | 1H NMR (400 MHz, DMSO-d6) δ (ppm) 2.71 (m, 2 H) 2.94 (s, 3 H) 3.32 (m partially masked, 2 H) 3.80 (s, 3 H) 4.41 (s, 1 H) 4.75 (m, 1 H) 7.09 (broad s, 1 H) 7.31 (d, J = 8.6 Hz, 4 H) 7.36 (d, J = 8.6 Hz, 4 H) 7.39 (dd, J = 2.4, 1.5 Hz, 1 H) 7.42 (broad s, 1 H) 13.20 (broad m, 1 H) |
| 4-Cl—Ph | 4-Cl—Ph | 5-CH$_3$ | Allyl | 1H-NMR (300 MHz, DMSO-d6): δ (ppm) = 7.75 (s, 1H), 7.66 (s, 1H), 7.44 (s, 1H), 7.37-7.29 (m, 8H), 6.09-5.97 (m, 1H), 5.38 (d, J = 17.2, 1H), 5.28 (d, J = 10.5, 1H), 4.80 (d, J = 5.4, 2H), 4.79-4.73 (m, 1H), 4.41 (s, 1H), 3.33-3.29 (m, 2H, overlapped with the H2O signal), 2.95 (s, 3H), 2.69 (t, J = 7.5, 2H), 2.37 (s, 3H). |
| 4-Cl—Ph | 4-Cl—Ph | 5-CH$_3$ | H | 1H NMR (500 MHz, DMSO-d6) δ (ppm) with: 2.38 (s, 3 H) 2.85-4.15 (m, 4 H) 2.99 (s, 3 H) 4.76-6.30 (m, 2 H) 7.20-7.83 (m, 11 H) 12.30-13.50 (m, 1 H) |
| 4-Cl—Ph | 4-Cl—Ph | 5-Cl | Me | 1H-NMR (300 MHz, DMSO-d6): δ (ppm) = 7.88 (s, 1H), 7.80 (s, 1H), 7.74 (s, 1H), 7.37-7.30 (m, 8H), 4.81-4.77 (m, 1H), 4.43 (s, 1H), 3.87 (s, 3H), 3.35-3.30 (m, 2H), 2.99 (s, 3H), 2.72 (t, J = 7.3, 2H). |
| 4-Cl—Ph | 4-Cl—Ph | 5-Cl | H | 1H NMR (400 MHz, DMSO-d6) δ (ppm) for this batch, all the signals are broad with: 2.70-4.20 (m, 4H) 3.03 (s, 3 H) 4.70-6.13 (m, 2 H) 7.30-7.70 (m, 8 H) 7.75 (s, 1 H) 7.98 (s, 2 H) 12.24-14.00 (m, 1 H) |
| 4-Cl—Ph | 4-Cl—Ph | 5-Br | Me | 1H-NMR (300 MHz, DMSO-d6): δ (ppm) = 8.00 (s, 1H), 7.86 (s, 1H), 7.83 (s, 1H), 7.37-7.29 (m, 8H), 4.81-4.77 (m, 1H), 4.43 (s, 1H), 3.87 (s, 3H), 3.34-3.29 (m, 2H overlapped with the H2O signal), 2.99 (s, 3H), 2.72 (t, J = 7.4, 2H). |
| 4-Cl—Ph | 4-Cl—Ph | 5-Br | H | 1H NMR (400 MHz, DMSO-d6) δ (ppm) 2.72-4.30 (m, 4H) 3.03 (s, 3 H) 4.78-6.25 (m, 2 H) 7.29-7.71 (m, 8 H) 7.87 (s, 1 H) 7.90 (s, 1 H) 8.01 (s, 1 H) 11.94-14.11 (m, 1 H) |
| 4-Cl—Ph | 4-Cl—Ph | 5-CF$_3$ | Me | 1H-NMR (300 MHz, DMSO-d6): δ (ppm) = 8.13-8.11 (m, 2H), 7.99 (s, 1H), 7.36-7.29 (m, 8H), 4.90-4.86 (m, 1H), 4.44 (s, 1H), 3.90 (s, 3H), 3.35-3.31 (m, 2H overlapped with the H2O signal), 3.01 (s, 3H), 2.75 (t, J = 7.2, 2H). |
| 4-Cl—Ph | 4-Cl—Ph | 5-CF$_3$ | H | 1H NMR (400 MHz, DMSO-d6) δ (ppm) 2.77 (m, 2 H) 3.01 (s, 3 H) 3.30 (m masked, 2 H) 4.44 (m, 1 H) 4.87 (m, 1 H) 7.26-7.39 (m, 8 H) 7.96 (s, 1 H) 8.12 (broad s, 2 H) 13.70 (broad m, 1 H) |
| 4-Cl—Ph | 4-Cl—Ph | 5-CN | Me | 1H-NMR (300 MHz, DMSO-d6): δ (ppm) = 8.28 (s, 1H), 8.13 (s, 1H), 8.10 (s, 1H), 7.37-7.29 (m, 8H), 4.81-4.77 (m, 1H), 4.42 (s, 1H), 3.89 (s, 3H), 3.38-3.32 (m, 2H overlapped with the H2O signal), 3.01 (s, 3H), 2.72 (t, J = 7.4, 2H). |
| 4-Cl—Ph | 4-Cl—Ph | 5-CN | H | 1H NMR (400 MHz, DMSO-d6) δ (ppm) 2.70-4 35 (m, 4H) 3.05 (s, 3 H) 4.83-6.34 (m, 2 H) 7.28-7.72 (m, 8 H) 8.11 (s, 1 H) 8.18 (s, 1 H) 8.27 (s, 1 H) 11.45-13.35 (m, 1 H) |

The following examples describe the preparation of certain compounds in accordance with the invention. These examples are not limiting and merely illustrate the present invention. The numbers of the compounds exemplified refer back to those given in the table hereinafter, which illustrates the chemical structures and the physical properties of some compounds according to the invention.

EXAMPLE 1

3-({1-[bis(4-chlorophenyl)methyl]azetidin-3-yl}methanesulphonylamino)-N—((S)-1-carbamoylethyl)benzamide (Compound No. 1)

67 mg of 1-hydroxybenzotriazole, 0.4 cm$^3$ of triethylamine and 228 mg of 1-(3-dimethylaminopropyl)-3-ethylcarbodiimide hydrochloride are added successively to a solution of 500 mg of 3-[{1-[bis(4-chlorophenyl)methyl]azetidin-3-yl}(methanesulphonyl)amino]benzoic acid and 150 mg of L-alaninamide hydrochloride in 20 cm$^3$ of tetrahydrofuran. The reaction mixture is left stirring overnight at a temperature in the region of 20° C. After concentration of the reaction medium to dryness under reduced pressure, the yellowish-white powder obtained is dissolved in dichloromethane. The organic phase is washed with water. After separation by settling out, the aqueous phase is again extracted with dichloromethane. The reaction crude obtained after concentration of the organic phases to dryness under reduced pressure is purified by flash chromatography on a Merck 30 g silica cartridge (elution gradient: 100/0 to 95/5 dichloromethane/methanol). After concentration of the fractions under reduced pressure, a white powder is obtained, which is washed with ethyl ether and oven-dried under vacuum. 430 mg of 3-({1-[bis(4-chlorophenyl)methyl]azetidin-3-yl}methanesulphonylamino)-N—((S)-1-carbamoylethyl)benzamide are thus obtained in the form of a white solid.

Mp.: 229° C.

1H NMR spectrum (300 MHz; (δ in ppm); (DMSO-d6); referenced at 2.50 ppm): 1.34 (d, J=7.1 Hz, 3H); 2.71 (t, J=6.8 Hz, 2H); 2.97 (s, 3H); 3.26-3.38 (m partially masked, 2H); 4.38 (s, 1H); 4.42 (m, 1H); 4.73 (quin, J=6.8 Hz, 1H); 6.98 (broad s, 1H); 7.31 (d, J=8.5 Hz, 4H); 7.36 (d, J=8.5 Hz, 4H); 7.39 (broad s, 1H); 7.44-7.54 (m, 2H); 7.80 (broad s, 1H); 7.89 (m, 1H); 8.50 (d, J=7.4 Hz, 1H)

Mass spectrum: ES m/z=575 (MH$^+$, base peak), m/z=235 ($C_{13}H_9Cl_2^+$), m/z=573 (MH$^-$)

Elemental Analysis:
Calculated: C, 56.35%; H, 4.90%; N, 9.73%; S, 5.57%.
Measured: C, 56.72%; H, 4.99%; N, 9.50%; S, 5.65%.
Optical rotation: $\alpha_D$=+10.3+/−0.6 (c=0.428, MeOH)

EXAMPLE 2

3-({1-[bis(4-chlorophenyl)methyl]azetidin-3-yl}methanesulphonylamino)-N-carbamoylmethyl-5-fluorobenzamide (Compound No. 2)

2a: 3-Fluoro-5-methanesulphonylaminobenzoic acid ethyl ester 2.65 cm$^3$ of pyridine are added to a solution of 4 g of 5-amino-3-fluorobenzoic acid ethyl ester in 100 cm$^3$ of dichloromethane stirred under an argon atmosphere. The reaction medium is cooled to a temperature in the region of 0° C. by means of an ice bath, and then a solution of 1.78 cm$^3$ of methanesulphonyl chloride in 2 cm$^3$ of dichloromethane is added dropwise. The orange solution obtained is allowed to return to a temperature in the region of 20° C. and is stirred at this temperature for 20 h. After the addition of 40 cm$^3$ of distilled water and of 50 cm$^3$ of dichloromethane, followed by separation by settling out, the organic phase is successively washed with 35 cm$^3$ of distilled water and then 40 cm$^3$ of a saturated aqueous solution of sodium chloride. The organic phase is dried over sodium sulphate, filtered through sintered glass and then concentrated to dryness under reduced pressure, to give 5.8 g of an orange solid. The reaction crude is purified by flash chromatography on a Merck 400 g silica cartridge (particle size: 15-40 μm; eluent: 98/2 dichloromethane/methanol). After concentration of the fractions under reduced pressure, 5.09 g of 3-fluoro-5-methanesulphonylaminobenzoic acid ethyl ester are obtained in the form of a white solid.

Mass spectrum: EI m/z=261 (M$^+$, base peak), m/z=233 [(M-C$_2$H$_4$)$^+$], m/z=216 [(M-OC$_2$H$_5$)$^+$], m/z=182 [(M-SO$_2$CH$_3$)$^+$], m/z=138 [(m/z=182-OC$_2$H$_4$)$^+$]

2b: 3-({1-[Bis(4-chlorophenyl)methyl]azetidin-3-yl}methanesulphonylamino)-5-fluorobenzoic acid ethyl ester 3.97 g of potassium carbonate are added to a suspension of 3.7 g of 1-[bis(4-chlorophenyl)methyl]azetidin-3-yl methanesulphonate and 3.5 g of 3-fluoro-5-methanesulphonylaminobenzoic acid ethyl ester in 130 cm$^3$ of 4-methyl-2-pentanone. The reaction medium is stirred at reflux for 7 hours and then allowed to return to a temperature in the region of 20° C. for 16 hours. 50 cm$^3$ of distilled water and 100 cm$^3$ of ethyl acetate are added to the cream suspension obtained. After stirring for 30 minutes followed by separation by settling out, the aqueous phase is extracted twice with 100 cm$^3$ of ethyl acetate. The combined organic phases are washed with 80 cm$^3$ of a saturated aqueous solution of sodium chloride, dried over sodium sulphate, filtered through sintered glass and then concentrated to dryness under reduced pressure, to give 7.2 g of an orange residue. The reaction crude is purified by flash chromatography on a Merck 400 g silica cartridge (particle size: 15-40 μm; elution gradient: 98/2 to 95/5 dichloromethane/methanol). After concentration of the fractions under reduced pressure, 4.03 g of 3-({1-[bis(4-chlorophenyl)methyl]azetidin-3-yl}methanesulphonylamino)-5-fluorobenzoic acid ethyl ester are obtained in the form of a white foam.

1H NMR spectrum (400 MHz; (δ in ppm); (DMSO-d6); referenced at 2.50 ppm): 1.32 (t, J=7.2 Hz, 3H); 2.73 (t, J=7.3 Hz, 2H); 2.98 (s, 3H); 3.35 (m, 2H); 4.34 (q, J=7.2 Hz, 2H); 4.43 (s, 1H); 4.77 (m, 1H); 7.31 (d, J=8.8 Hz, 4H); 7.37 (d, J=8.8 Hz, 4H); 7.56 (dt, J=9.8; 2.4 Hz, 1H); 7.66 (broad d, J=9.1 Hz, 1H); 7.70 (broad s, 1H)

Mass spectrum: ES m/z=551 (MH$^+$), m/z=235 ($C_{13}H_9Cl_2^+$; base peak)

2c: 3-({1-[Bis(4-chlorophenyl)methyl]azetidin-3-yl}methanesulphonylamino)-5-fluorobenzoic acid 0.222 g of lithium hydroxide is added, in two parts, to a solution of 2.5 g of 3-({1-[bis(4-chlorophenyl)methyl]azetidin-3-yl}methanesulphonylamino)-5-fluorobenzoic acid ethyl ester in a mixture comprising 34 cm$^3$ of tetrahydrofuran and 9 cm$^3$ of water, stirred under an argon atmosphere. The reaction medium is stirred at a temperature in the region of 20° C. for 24 hours. 100 cm$^3$ of a saturated aqueous solution of sodium hydrogen phosphate are then added so as to bring the pH to 5. The aqueous phase is extracted four times with 200 cm$^3$ of ethyl acetate. The combined organic phases are dried over sodium sulphate, filtered through sintered glass and then concentrated to dryness under reduced pressure, to give a foam which is taken up twice with 150 cm³ of ethyl ether. After concentration under reduced pressure, 2.3 g of 3-({1-[bis(4-chlorophenyl)methyl]azetidin-3-yl}methanesulphonylamino)-5-fluorobenzoic acid are obtained in the form of a white solid.

1H NMR spectrum (400 MHz; (δ in ppm); (DMSO-d6); referenced at 2.50 ppm): 2.74 (t, J=6.9 Hz, 2H); 2.98 (s, 3H); 3.33 (m masked, 2H); 4.43 (s, 1H); 4.76 (quin, J=6.9 Hz, 1H); 7.31 (d, J=8.8 Hz, 4H); 7.36 (d, J=8.8 Hz, 4H); 7.51 (dt, J=9.4; 2.0 Hz, 1H); 7.64 (dt, J=8.9; 2.0 Hz, 1H); 7.70 (t, J=2.0 Hz, 1H); 13.25 (very broad m, 1H)

Mass spectrum: ES m/z=523 (MH⁺), m/z=235 ($C_{13}H_9Cl_2^+$, base peak)

2d: 3-({1-[Bis(4-chlorophenyl)methyl]azetidin-3-yl}methanesulphonylamino)-N-carbamoylmethyl-5-fluorobenzamide (Compound No. 2)

0.115 cm³ of isobutyl chloroformate is added to a solution of 0.4 g of 3-({1-[bis(4-chlorophenyl)methyl]azetidin-3-yl}methanesulphonylamino)-5-fluorobenzoic acid and 0.245 cm³ of triethylamine in 5 cm³ of tetrahydrofuran. A precipitate appears and the reaction medium is stirred at a temperature in the region of 20° C. for 30 minutes, before adding, in a single step, 0.101 g of glycinamide with 1 cm³ of tetrahydrofuran. The white suspension obtained is stirred at a temperature in the region of 20° C. for 20 hours. The reaction medium is filtered through sintered glass, rinsing with 50 cm³ of tetrahydrofuran. The filtrate is concentrated to dryness under vacuum, to give 0.55 g of a yellow foam which is purified by flash chromatography on a Merck 70 g silica cartridge (particle size: 15-40 μm; eluent: 98/2 dichloromethane/methanol). After concentration of the fractions under reduced pressure, a foam is obtained which is taken up with diethyl ether, filtered, and then dried under vacuum at a temperature in the region of 50° C. The solid thus obtained is taken up with 20 cm³ of pentane and left in the pentane overnight. After filtration, the product is dried under vacuum. 0.222 g of 3-({1-[bis(4-chlorophenyl)methyl]azetidin-3-yl}methanesulphonylamino)-N-carbamoylmethyl-5-fluorobenzamide is then obtained in the form of a yellowish solid.

Mp.: 154-156° C.

1H NMR spectrum (400 MHz; (δ in ppm); (DMSO-d6); referenced at 2.50 ppm): 2.73 (t, J=7.0 Hz, 2H); 3.00 (s, 3H); 3.36 (m, 2H); 3.81 (d, J=5.9 Hz, 2H); 4.40 (s, 1H); 4.72 (m, 1H); 7.04 (broad s, 1H); 7.31 (d, J=8.8 Hz, 4H); 7.35 (d, J=8.8 Hz, 4H); 7.37-7.47 (m, 2H); 7.60-7.73 (m, 2H); 8.84 (t, J=5.9 Hz, 1H)

Mass spectrum: ES m/z=579 (MH⁺, base peak), m/z=235 ($C_{13}H_9Cl_2^+$)

Elemental Analysis:
Calculated: C, 53.89%; H, 4.35%; N, 9.67%; S, 5.53%.
Measured: C, 53.88%; H, 4.71%; N, 9.16%; S, 5.66%.

EXAMPLE 3

3-({1-[Bis(4-chlorophenyl)methyl]azetidin-3-yl}methanesulphonylamino)-N—((S)-1-carbamoylethyl)-5-fluorobenzamide (Compound No. 3)

0.1 cm³ of isobutyl chloroformate is added to a solution of 0.35 g of 3-({1-[bis(4-chlorophenyl)methyl]azetidin-3-yl}methanesulphonylamino)-5-fluorobenzoic acid and 0.214 cm³ of triethylamine in 5 cm³ of tetrahydrofuran. The reaction medium is stirred at a temperature in the region of 20° C. for 1 hour 10 minutes before adding, in a single step, 0.113 g of L-alaninamide hydrochloride with 2 cm³ of tetrahydrofuran. The white suspension obtained is stirred at a temperature in the region of 20° C. for 48 hours. The reaction medium is filtered through sintered glass, rinsing with tetrahydrofuran. The filtrate is concentrated to dryness under vacuum, to give 0.5 g of a white foam which is purified by flash chromatography on a Merck 70 g silica cartridge (particle size: 15-40 μm; eluent: 97/3 dichloromethane/methanol). After concentration of the fractions under reduced pressure, a foam is obtained which is taken up with diethyl ether, filtered, and then dried under vacuum at a temperature in the region of 50° C., to give 0.307 g of a white solid. This solid is recrystallized under hot conditions from an ethanol/water mixture and dried under vacuum at a temperature in the region of 45° C. 0.213 g of 3-({1-[bis(4-chlorophenyl)methyl]azetidin-3-yl}methanesulphonylamino)-N—((S)-1-carbamoylethyl)-5-fluorobenzamide is thus obtained in the form of a white solid.

Mp.: 228-230° C.

1H NMR spectrum (400 MHz; (δ in ppm); (DMSO-d6); referenced at 2.50 ppm): 1.33 (d, J=7.3 Hz, 3H); 2.73 (t, J=6.8 Hz, 2H); 3.00 (s, 3H); 3.24-3.43 (m partially masked, 2H); 4.34-4.48 (m, 2H); 4.72 (quin, J=6.8 Hz, 1H); 6.99 (broad s, 1H); 7.31 (d, J=8.5 Hz, 4H); 7.37 (d, J=8.5 Hz, 4H); 7.39-7.45 (m, 2H); 7.67 (broad s, 1H); 7.74 (broad d, J=8.8 Hz, 1H); 8.61 (d, J=7.3 Hz, 1H)

Mass spectrum: ES m/z=593 (MH⁺, base peak), m/z=637 (MH⁻+HCO₂H), m/z=591 (MH⁻, base peak)

Elemental Analysis:
Calculated: C, 54.64%; H, 4.59%; N, 9.44%; S, 5.40%.
Measured: C, 54.09%; H, 4.66%; N, 9.34%; S, 5.43%; H₂O: 1.71%.

Optical rotation: $\alpha_D$=+11.3+/−0.7 (c=0.365, MeOH)

EXAMPLE 4

3-({1-[bis(4-chlorophenyl)methyl]azetidin-3-yl}methanesulphonylamino)-N—((R)-1-carbamoylethyl)-5-fluorobenzamide (Compound No. 4)

0.1 cm³ of isobutyl chloroformate is added to a solution of 0.35 g of 3-({1-[bis(4-chlorophenyl)methyl]azetidin-3-yl}methanesulphonylamino)-5-fluorobenzoic acid and 0.216 cm³ of triethylamine in 7 cm³ of tetrahydrofuran. A precipitate appears. The reaction medium is stirred at a temperature in the region of 20° C. for 1 hour 25 minutes, before adding, in a single step, 0.108 g of D-alaninamide hydrochloride with 2 cm³ of tetrahydrofuran. The white suspension obtained is stirred at a temperature in the region of 20° C. for 24 hours. The reaction medium is filtered through sintered glass, rinsing with tetrahydrofuran. The filtrate is concentrated to dryness under vacuum, to give 0.5 g of a white foam which is purified by flash chromatography on a Merck 70 g silica cartridge (particle size: 15-40 μm; eluent: 97/3 dichloromethane/methanol). After concentration of the fractions under reduced pressure, a foam is obtained which is taken up with diethyl ether, filtered, and then dried under vacuum at a temperature in the region of 50° C., to give a solid. This solid is recrystallized under hot conditions from an ethanol/water mixture and dried under vacuum at a temperature in the region of 45° C. 0.095 g of 3-({1-[bis(4-chlorophenyl)methyl]azetidin-3-yl}methanesulphonylamino)-N—((R)-1-carbamoylethyl)-5-fluorobenzamide is thus obtained in the form of a white solid.

Mp.: 219-221° C.

1H NMR spectrum (400 MHz; (δ in ppm); (DMSO-d6); referenced at 2.50 ppm): 1.33 (d, J=6.8 Hz, 3H); 2.73 (t, J=7.1

Hz, 2H); 3.00 (s, 3H); 3.35 (m, 2H); 4.35-4.45 (m, 2H); 4.73 (quin, J=6.8 Hz, 1H); 6.99 (broad s, 1H); 7.31 (d, J=8.8 Hz, 4H); 7.37 (d, J=8.8 Hz, 4H); 7.39-7.45 (m, 2H); 7.68 (t, J=1.7 Hz, 1H); 7.74 (dt, J=9.0; 1.7 Hz, 1H); 8.62 (d, J=7.8 Hz, 1H)

Mass spectrum: ES m/z=593 (MH$^+$, base peak), m/z=235 ($C_{13}H_9Cl_2^{+\cdot}$)

Elemental Analysis:

Calculated: C, 54.64%; H, 4.59%; N, 9.44%; S, 5.40%.

Measured: C, 54.44%; H, 4.54%; N, 9.48%; S, 5.36%; $H_2O<0.1\%$.

Optical rotation: $\alpha_D=-23.3+/-0.7$ (c=0.476, DMSO)

EXAMPLE 5

3-({1-[Bis(4-chlorophenyl)methyl]azetidin-3-yl}methanesulphonylamino)-N—((R)-1-carbamoyl-ethyl)benzamide (Compound No. 5)

67 mg of 1-hydroxybenzotriazole, 0.4 cm³ of triethylamine and 228 mg of 1-(3-dimethylaminopropyl)-3-ethylcarbodiimide hydrochloride are added successively to a solution of 500 mg of 3-({1-[bis(4-chlorophenyl)methyl]azetidin-3-yl}methanesulphonylaminobenzoic acid and 150 mg of D-alaninamide hydrochloride in 20 cm³ of tetrahydrofuran. The reaction mixture is left stirring overnight at a temperature in the region of 20° C. After concentration of the reaction medium to dryness under reduced pressure, the yellowish-white powder obtained is dissolved with dichloromethane. The organic phase is washed with water. After separation by settling out, the aqueous phase is again extracted with dichloromethane. The reaction crude obtained after concentration of the organic phases to dryness under reduced pressure is purified by flash chromatography on a Merck 30 g silica cartridge (elution gradient: 100/0 to 95/5 dichloromethane/methanol). After concentration of the fractions under reduced pressure, a product is obtained which is washed with diethyl ether and oven-dried under vacuum. 220 mg of 3-({1-[bis(4-chlorophenyl)methyl]azetidin-3-yl}methanesulphonylamino)-N—((R)-1-carbamoylethyl)benzamide are thus obtained in the form of white crystals.

Mp.: 235° C.

1H NMR spectrum (300 MHz; (δ in ppm); (DMSO-d6); referenced at 2.50 ppm): 1.34 (d, J=7.3 Hz, 3H); 2.71 (t, J=6.8 Hz, 2H); 2.97 (s, 3H); 3.32 (broad m, 2H); 4.38 (s, 1H); 4.42 (m, 1H); 4.74 (quin, J=6.8 Hz, 1H); 6.98 (broad s, 1H); 7.31 (d, J=8.8 Hz, 4H); 7.36 (d, J=8.8 Hz, 4H); 7.39 (broad s, 1H); 7.45-7.54 (m, 2H); 7.80 (broad s, 1H); 7.88 (m, 1H); 8.50 (d, J=7.6 Hz, 1H)

Mass spectrum: ES m/z=575 (MH$^+$, base peak), m/z=235 ($C_{13}H_9Cl_2^{+\cdot}$)

Elemental Analysis:

Calculated: C, 56.35%; H, 4.90%; N, 9.73%; S, 5.57%.

Measured: C, 56.84%; H, 5.17%; N, 9.56%; S, 5.51%.

Optical rotation: $\alpha_D=-6.6+/-0.5$ (c=0.493, DMSO)

EXAMPLE 6

3-({1-[bis(4-chlorophenyl)methyl]azetidin-3-yl}methanesulphonylamino)-N—((S)-1-carbamoyl-2-hydroxyethyl)benzamide (Compound No. 6)

0.114 cm³ of isobutyl chloroformate is added to a solution of 0.4 g of 3-({1-[bis(4-chlorophenyl)methyl]azetidin-3-yl}methanesulphonylamino)benzoic acid and 0.253 cm³ of triethylamine in 5 cm³ of tetrahydrofuran stirred at a temperature of between −10 and −15° C. A precipitate appears. The reaction medium is stirred at a temperature of less than 0° C. for 1 hour 15 minutes, before adding 0.166 g of L-serinamide hydrochloride with 3 cm³ of tetrahydrofuran, while at the same time maintaining the temperature of the reaction medium between −10 and −15° C. The white suspension obtained is stirred at a temperature in the region of 20° C. overnight. The reaction medium is again cooled and maintained at a temperature of between −10° C. and −15° C., before adding: 22 µl of triethylamine, 21 µl of isobutyl chloroformate and 22.2 mg of L-serinamide hydrochloride in 2 cm³ of tetrahydrofuran. After stirring for 3 hours at a temperature in the region of 20° C., the reaction medium is filtered through sintered glass and rinsed with dichloromethane. The filtrate is concentrated to dryness under reduced pressure, to give 0.726 g of a white foam which is purified by flash chromatography on a Merck 70 g silica cartridge (particle size: 15-40 µm; elution gradient: 99/1 to 98/2 ethyl acetate/methanol). After concentration of the fractions under reduced pressure, a white residue is obtained which is taken up in 35 cm³ of diethyl ether, filtered, and then dried under vacuum at a temperature in the region of 40° C. This operation is repeated a second time with 6 cm³ of diethyl ether. 0.21 g of 3-({1-[bis(4-chlorophenyl)methyl]azetidin-3-yl}methanesulphonylamino)-N—((S)-1-carbamoyl-2-hydroxyethyl)benzamide is thus obtained in the form of a white solid.

Mp.: 245-247° C.

1H NMR spectrum (400 MHz; (δ in ppm); (DMSO-d6); referenced at 2.50 ppm): 2.71 (t, J=6.9 Hz, 2H); 2.97 (s, 3H); 3.33 (m masked, 2H); 3.71 (m, 2H); 4.38 (s, 1H); 4.44 (m, 1H); 4.75 (quin, J=6.9 Hz, 1H); 4.93 (broad t, J=5.9 Hz, 1H); 7.10 (broad s, 1H); 7.31 (d, J=8.8 Hz, 4H); 7.36 (d, J=8.8 Hz, 4H); 7.41 (broad s, 1H); 7.45-7.55 (m, 2H); 7.81 (broad s, 1H); 7.88 (m, 1H); 8.30 (d, J=7.8 Hz, 1H)

Mass spectrum: ES m/z=591 (MH$^+$, base peak), m/z=235 ($C_{13}H_9Cl_2^{+\cdot}$)

Elemental Analysis

Calculated: C, 54.83%; H, 4.77%; N, 9.47%; S, 5.42%.

Measured: C, 53.60%; H, 5.04%; N, 9.00%; S, 4.90%; $H_2O=1.45\%$.

Optical rotation: $\alpha_D=+30.9+/-0.8$ (c=0.412, DMSO)

EXAMPLE 7

3-({1-[bis(4-chlorophenyl)methyl]azetidin-3-yl}methanesulphonylamino)-N-(2-carbamoylethyl)benzamide (Compound No. 7)

0.142 cm³ of isobutyl chloroformate is added to a solution of 0.5 g of 3-({1-[bis(4-chlorophenyl)methyl]azetidin-3-yl}methanesulphonylamino)benzoic acid and 0.317 cm³ of triethylamine in 6 cm³ of tetrahydrofuran stirred at a temperature of between −10 and −20° C. A precipitate appears. The reaction medium is stirred at a temperature of less than 0° C. for 2 hours, before adding 0.184 g of β-alaninamide hydrochloride with 2 cm³ of tetrahydrofuran while at the same time maintaining the temperature of the reaction medium between −10 and −20° C. The white suspension obtained is stirred at a temperature in the region of 20° C. for 3 hours. The reaction medium is again cooled and maintained at a temperature of between −10° C. and −20° C., before adding: 27.5 µl of triethylamine, 25.8 µl of isobutyl chloroformate and 24.6 mg of β-alaninamide hydrochloride in 2 cm³ of tetrahydrofuran. After stirring for 15 hours at a temperature in the region of 20° C., the reaction medium is filtered through sintered glass and rinsed with dichloromethane. The filtrate is concentrated to dryness under reduced pressure, to give 1 g of a white foam which is purified by flash chromatography on a Merck 70 g silica cartridge (particle size: 15-40 µm; eluent: 98/2 ethyl acetate/methanol). After concentration of the fractions under reduced pressure, a white residue is obtained which is taken up in 35 cm³ of diethyl ether, filtered, and then dried under vacuum at a temperature in the region of 40° C. 0.429 g of 3-({1-[bis(4-chlorophenyl)methyl]azetidin-3-yl}methanesulphonylamino)-N-(2-carbamoylethyl)benzamide is thus obtained in the form of a white solid.

Mp.: 190-192° C.

1H NMR spectrum (400 MHz; (δ in ppm); (DMSO-d6); referenced at 2.50 ppm): 2.35 (t, J=7.1 Hz, 2H); 2.69 (t, J=6.9 Hz, 2H); 2.95 (s, 3H); 3.34 (t, J=6.9 Hz, 2H); 3.44 (m, 2H); 4.37 (s, 1H); 4.73 (quin, J=6.9 Hz, 1H); 6.81 (broad s, 1H); 7.31 (d, J=8.8 Hz, 4H); 7.35 (s masked, 1H); 7.36 (d, J=8.8 Hz, 4H); 7.41-7.52 (m, 2H); 7.74 (broad s, 1H); 7.80 (m, 1H); 8.58 (t, J=5.6 Hz, 1H)

Mass spectrum: ES m/z=575 (MH⁺, base peak), m/z=235 ($C_{13}H_9Cl_2^+$)

Elemental Analysis:

Calculated: C, 56.35%; H, 4.90%; N, 9.73%; S, 5.57%.

Measured: C, 56.36%; H, 5.10%; N, 9.46%; S, 5.29%; $H_2O$=0.34%.

EXAMPLE 8

3-({1-[bis(4-chlorophenyl)methyl]azetidin-3-yl}methanesulphonylamino)-N-(2-morpholin-4-yl-2-oxoethyl)benzamide (Compound No. 8)

67 mg of 1-hydroxybenzotriazole, 0.14 cm³ of triethylamine and 270 mg of 1-(3-dimethylaminopropyl)-3-ethylcarbodiimide hydrochloride are added successively to a solution of 500 mg of 3-({1-[bis(4-chlorophenyl)methyl]azetidin-3-yl}methanesulphonylamino)benzoic acid and 215 mg of 2-amino-1-morpholin-4-ylethanone hydrochloride in 15 cm³ of tetrahydrofuran. The reaction mixture is left stirring overnight at a temperature in the region of 20° C. After concentration of the reaction medium to dryness under reduced pressure, the residue obtained is taken up with dichloromethane. The organic phase is washed with water, dried, and concentrated to dryness under reduced pressure, to give a reaction crude which is purified by flash chromatography on a Merck 30 g silica cartridge (elution gradient: 100/0 to 95/5 dichloromethane/methanol). After concentration of the fractions under reduced pressure, a white foam is obtained which crystallizes after trituration with diethyl ether. After filtration and drying using a vane pump, 470 mg of 3-({1-[bis(4-chlorophenyl)methyl]azetidin-3-yl}methanesulphonylamino)-N-(2-morpholin-4-yl-2-oxoethyl)benzamide are thus obtained in the form of white crystals.

Mp.: 176° C.

1H NMR spectrum (400 MHz; (δ in ppm); (DMSO-d6); referenced at 2.50 ppm): 2.71 (t, J=6.9 Hz, 2H); 2.97 (s, 3H); 3.34 (t, J=6.9 Hz, 2H); 3.48 (m, 4H); 3.58 (m, 4H); 4.13 (d, J=5.5 Hz, 2H); 4.37 (s, 1H); 4.74 (quin, J=6.9 Hz, 1H); 7.31 (d, J=8.8 Hz, 4H); 7.35 (d, J=8.8 Hz, 4H); 7.47-7.55 (m, 2H); 7.78 (broad s, 1H); 7.85 (m, 1H); 8.66 (t, J=5.5 Hz, 1H)

Mass spectrum: ES m/z=631 (MH⁺, base peak), m/z=235 ($C_{13}H_9Cl_2^+$)

Elemental Analysis:

Calculated: C, 57.05%; H, 5.11%; N, 8.87%; S, 5.08%.

Measured: C, 57.29%; H, 4.96%; N, 8.29%; S, 4.93%.

EXAMPLE 9

3-({1-[bis(4-chlorophenyl)methyl]azetidin-3-yl}methanesulphonylamino)-N—((S)-1-methylcarbamoylethyl)benzamide (Compound No. 9)

Pathway A 0.113 cm³ of isobutyl chloroformate is added to a solution of 0.4 g of 3-({1-[bis(4-chlorophenyl)methyl]azetidin-3-yl}methanesulphonylamino)benzoic acid and 0.256 cm³ of triethylamine in 4 cm³ of tetrahydrofuran, stirred under an inert atmosphere at a temperature of between −10 and −20° C. A precipitate appears. The reaction medium is stirred at a temperature of less than 0° C. for 1 hour, before adding 0.143 g of L-alanine methylamide hydrochloride with 2 cm³ of tetrahydrofuran while at the same time maintaining the temperature of the reaction medium between −10 and −20° C. The white suspension obtained is stirred at a temperature in the region of 20° C. for 18 hours. The reaction medium is again cooled and maintained at a temperature of between −10° C. and −20° C., before adding: 22 µl of triethylamine, 20.6 µl of isobutyl chloroformate and 22 mg of L-alanine methylamide hydrochloride in 2 cm³ of tetrahydrofuran. After stirring for 24 hours at a temperature in the region of 20° C., the reaction medium is filtered through sintered glass and rinsed with dichloromethane. The filtrate is concentrated to dryness under reduced pressure, to give 0.684 g of a white foam which is purified by flash chromatography on a Merck 70 g silica cartridge (particle size: 15-40 µm; eluent: 98/2 ethyl acetate/methanol). After concentration of the fractions under reduced pressure, a white residue is obtained which is recrystallized from an absolute ethanol/water mixture. The solid obtained is filtered through sintered glass and dried under vacuum at a temperature in the region of 40° C. 0.128 g of 3-({1-[bis(4-chlorophenyl)methyl]azetidin-3-yl}methanesulphonylamino)-N—((S)-1-methylcarbamoylethyl)benzamide is thus obtained in the form of a white solid.

Mp.: 171-173° C.

1H NMR spectrum (400 MHz; (δ in ppm); (DMSO-d6); referenced at 2.50 ppm): 1.32 (d, J=7.0 Hz, 3H); 2.59 (d, J=4.9 Hz, 3H); 2.71 (t, J=7.6 Hz, 2H); 2.97 (s, 3H); 3.33 (t, J=7.6 Hz partially masked, 2H); 4.38 (s, 1H); 4.44 (m, 1H); 4.74 (m, 1H); 7.31 (d, J=8.5 Hz, 4H); 7.35 (d, J=8.5 Hz, 4H); 7.44-7.52 (m, 2H); 7.80 (s, 1H); 7.83-7.91 (m, 2H); 8.59 (d, J=7.8 Hz, 1H)

Mass spectrum: ES m/z=589 (MH⁺, base peak)

Elemental Analysis:

Calculated: C, 57.05%; H, 5.13%; N, 9.50%; S, 5.44%.

Measured: C, 55.49%; H, 5.50%; N, 9.14%; S, 5.10%; $H_2O$=2.57%.

Optical rotation: $α_D$=+25.4+/−0.7 (c=0.427, DMSO)

Pathway B

Pathway B-a: (S)-2-[3-({1-[bis(4-chlorophenyl)methyl]azetidin-3-yl}methanesulphonyl-amino)benzoylamino]propionic acid tert-butyl ester 0.345 cm³ of triethylamine is added to a solution of 0.5 g of 3-({1-[bis(4-chlorophenyl)methyl]azetidin-3-yl}methanesulphonylamino)benzoic acid in 9 cm³ of anhydrous tetrahydrofuran, stirred under an inert atmosphere at a temperature in the region of −50° C. The reaction medium is stirred for 5 minutes, before adding, at the same temperature, 0.140 cm³ of isobutyl chloroformate. After stirring for 1 hour at a temperature in the region of −50° C., 0.270 g of (S)-2- aminopropionic acid tert-butyl ester hydrochloride is added with 6 cm³ of tetrahydrofuran. The reaction medium is stirred at a temperature in the region of −50° C. for 10 minutes, and is then allowed to return to a temperature in the region of 20° C. After stirring for 3 hours, the medium is hydrolyzed at a temperature of between −20° C. and −30° C. with 10 cm³ of water, and then stirred for 15 minutes at a temperature in the region of 20° C. The aqueous phase is extracted three times with 25 cm³ of ethyl acetate. The combined organic phases are dried over magnesium sulphate, filtered through sintered glass and concentrated to dryness under reduced pressure, to give 0.815 g of a crude product which is purified by flash chromatography on a Merck 70 g silica cartridge (particle size: 15-40 μm; eluent: 99/1 ethyl acetate/methanol). After concentration of the fractions under reduced pressure, 0.418 g of a white foam is obtained, which is taken up in pentane. The insoluble material is filtered off through sintered glass and then dried under vacuum at a temperature of 40° C. 0.364 g of (S)-2-[3-({1-[bis(4-chlorophenyl)methyl]azetidin-3-yl}methanesulphonylamino)-benzoylamino]propionic acid tert-butyl ester is thus obtained in the form of a white solid.

1H NMR spectrum (400 MHz; (δ in ppm); (DMSO-d6); referenced at 2.50 ppm): 1.38 (m masked, 3H); 1.39 (s, 9H); 2.71 (m, 2H); 2.97 (s, 3H); 3.34 (m partially masked, 2H); 4.35 (m, 1H); 4.37 (s, 1H); 4.74 (m, 1H); 7.30 (d, J=8.5 Hz, 4H); 7.34 (d, J=8.5 Hz, 4H); 7.43-7.55 (m, 2H); 7.79 (broad s, 1H); 7.86 (m, 1H); 8.72 (d, J=7.3 Hz, 1H)

Mass spectrum: ES m/z=632 (MH+, base peak)
Optical rotation: $\alpha_D$=+3.6+/−0.5 (c=0.448, DMSO)

Pathway B-b: (S)-2-[3-({1-[bis(4-chlorophenyl)methyl]azetidin-3-yl}methanesulphonyl-amino)benzoylamino]propionic acid 2.72 cm³ of trifluoroacetic acid are added dropwise to a solution of 0.5 g of (S)-2-[3-({1-[bis(4-chlorophenyl)methyl]azetidin-3-yl}methanesulphonylamino)benzoylamino]propionic acid tert-butyl ester in 11 cm³ of dichloromethane, stirred at a temperature in the region of 20° C. under an inert atmosphere. The reaction medium is stirred at a temperature in the region of 20° C. for 19 hours, before being concentrated to dryness under reduced pressure. In order to remove the excess trifluoroacetic acid, two entrainments are performed with 15 cm³ of toluene. The residue obtained is dissolved in 10 cm³ of water. The aqueous phase is basified at pH=7 with 3 drops of a 1M aqueous solution of sodium hydroxide, and then extracted three times with 20 cm³ of dichloromethane. The combined aqueous phases are dried over magnesium sulphate, filtered through sintered glass and concentrated to dryness under reduced pressure, to give 0.43 g of a yellowish foam which is purified by flash chromatography on a Merck 25 g silica cartridge (particle size: 15-40 μm; eluent: 100 ethyl acetate). After concentration of the fractions under reduced pressure, 0.207 g of a product is obtained which is triturated in a minimum amount of pentane. After concentration to dryness under reduced pressure and drying, 0.169 g of (S)-2-[3-({1-[bis(4-chlorophenyl)methyl]azetidin-3-yl}methanesulphonylamino)benzoylamino]propionic acid is obtained in the form of a white powder.

1H NMR spectrum (400 MHz; (δ in ppm); (DMSO-d6); referenced at 2.50 ppm): 1.39 (d, J=7.3 Hz, 3H); 2.71 (m, 2H); 2.97 (s, 3H); 3.23-3.45 (m masked, 2H); 4.38 (s, 1H); 4.39 (m, 1H); 4.74 (m, 1H); 7.30 (d, J=8.3 Hz, 4H); 7.35 (d, J=8.3 Hz, 4H); 7.44-7.56 (m, 2H); 7.80 (broad s, 1H); 7.86 (m, 1H); 8.70 (d, J=7.3 Hz, 1H)

Mass spectrum: ES m/z=576 (MH+, base peak)
Elemental Analysis:
Calculated: C, 56.25%; H, 4.72%; N, 7.29%; S, 5.56%.
Measured: C, 55.68%; H, 4.99%; N, 6.89%; S, 5.01%; H₂O=0.82%.
Optical rotation: $\alpha_D$=+10 (c=0.195, DMSO)

Pathway B-c: 3-({1-[bis(4-chlorophenyl)methyl]azetidin-3-yl}methanesulphonylamino)-N—((S)-1-methylcarbamoylethyl)benzamide (Compound No. 9)

60 mg of 1-hydroxybenzotriazole, 200 mg of 1-(3-dimethylaminopropyl)-3-ethylcarbodiimide hydrochloride, 0.700 cm³ of a 2M solution of methylamine in tetrahydrofuran, 0.370 cm³ of triethylamine and 8 cm³ of tetrahydrofuran are added successively to a solution of 0.5 g of (S)-2-[3-({1-[bis(4-chlorophenyl)methyl]azetidin-3-yl}methanesulphonylamino)benzoyl-amino]propionic acid in 15 cm³ of tetrahydrofuran, stirred at a temperature in the region of 20° C. under an inert atmosphere. The reaction medium is stirred at a temperature in the region of 20° C. for 18 hours. After concentration to dryness under reduced pressure, the residue is dissolved in a mixture consisting of 30/15 cm³ of dichloromethane/water. After separation by settling out, the aqueous phase is extracted twice with 15 cm³ of dichloromethane. The organic phases are combined, washed with 15 cm³ of a saturated aqueous solution of sodium chloride, dried over magnesium sulphate, filtered and then concentrated to dryness, to give 0.415 g of a crude product which is purified by flash chromatography on a Merck 25 g silica cartridge (particle size: 15-40 μm; eluent: 100 ethyl acetate). After concentration of the fractions under reduced pressure, 0.293 g of a product is obtained which is triturated in a minimum amount of pentane. After filtration, concentration to dryness under reduced pressure and drying, 0.247 g of a solid cream is obtained. 147 mg of this solid cream are injected onto a column 6 cm in diameter containing 700 g of Chiralpak IA 20 μM chiral stationary phase. The elution is carried out at 80 cm³ per minute with a mobile phase composed of 95% acetonitrile and 5% dichloromethane. The dextrorotatory enantiomer is eluted in the second position. After concentration of the mobile phase, 105 mg of 3-({1-[bis(4-chlorophenyl)methyl]azetidin-3-yl}methanesulphonylamino)-N—((S)-1-methyl-carbamoylethyl)benzamide are obtained in the form of an amorphous white powder.

Table 1 which follows illustrates the chemical structures (I) and the physical properties (Table 1A) of some examples of compounds according to the invention. In this table:

Na salt corresponds to the sodium salt; "Me" corresponds to a methyl group; "Et" corresponds to an ethyl group; "iPr" corresponds to an isopropyl group; "iBu" corresponds to an isobutyl group; "tBu" corresponds to a tert-butyl group; "Ph" is a phenyl group;

R is a methyl group;

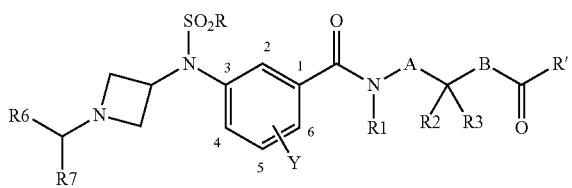

(I)

TABLE 1

| N° | R1 | A | B | R2, R3 | R' | R6 | R7 | Y | Salt/chirality |
|---|---|---|---|---|---|---|---|---|---|
| 1 | H | — | — | Me, H | NH$_2$ | 4-Cl—Ph | 4-Cl—Ph | H | Chiral (S) |
| 2 | H | — | — | H, H | NH$_2$ | 4-Cl—Ph | 4-Cl—Ph | 5-F | — |
| 3 | H | — | — | Me, H | NH$_2$ | 4-Cl—Ph | 4-Cl—Ph | 5-F | Chiral (S) |
| 4 | H | — | — | Me, H | NH$_2$ | 4-Cl—Ph | 4-Cl—Ph | 5-F | Chiral (R) |
| 5 | H | — | — | Me, H | NH$_2$ | 4-Cl—Ph | 4-Cl—Ph | H | Chiral (R) |
| 6 | H | — | — | CH$_2$OH, H | NH$_2$ | 4-Cl—Ph | 4-Cl—Ph | H | Chiral (S) |
| 7 | H | CH$_2$ | — | H, H | NH$_2$ | 4-Cl—Ph | 4-Cl—Ph | H | — |
| 8 | H | — | — | H, H | 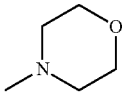 | 4-Cl—Ph | 4-Cl—Ph | H | — |
| 9 | H | — | — | H, Me | NHMe | 4-Cl—Ph | 4-Cl—Ph | H | Chiral (S) |
| 10 | H | — | — | H, Et | NH$_2$ | 4-Cl—Ph | 4-Cl—Ph | H | Chiral (S) |
| 11 | H | — | — | H, iBu | NH$_2$ | 4-Cl—Ph | 4-Cl—Ph | H | Chiral (S) |
| 12 | H | — | — | H, iPr | NH$_2$ | 4-Cl—Ph | 4-Cl—Ph | 5-F | Chiral (S) |
| 13 | H | — | — | CH$_2$OH, H | NH$_2$ | 4-Cl—Ph | 4-Cl—Ph | 5-F | Chiral (S) |
| 14 | H | — | — | Et, H | NH$_2$ | 4-Cl—Ph | 4-Cl—Ph | 5-F | Chiral (S) |
| 15 | H | — | — | H, H | NHMe | 4-Cl—Ph | 4-Cl—Ph | H | — |
| 16 | H | — | — | H, H | NH$_2$ | 4-Cl—Ph | 4-Cl—Ph | H | — |
| 17 | H | — | — | Me, H | OtBu | 4-Cl—Ph | 4-Cl—Ph | H | Chiral (S) |
| 18 | H | — | — | Me, H | OH | 4-Cl—Ph | 4-Cl—Ph | H | Chiral (S) |
| 19 | H | — | — | H, H | OtBu | 4-Cl—Ph | 4-Cl—Ph | H | — |
| 20 | H | CH$_2$ | CH$_2$ | H, H | OtBu | 4-Cl—Ph | 4-Cl—Ph | 5-F | — |
| 21 | H | — | — | H, Me | OtBu | 4-Cl—Ph | 4-Cl—Ph | 5-F | Chiral (S) |
| 22 | H | — | — | H, Me | NH$_2$ | 4-Cl—Ph | 4-Cl—Ph | 5-OMe | Chiral (S) |
| 23 | H | — | — | H, Me | NMe$_2$ | 4-Cl—Ph | 4-Cl—Ph | H | Chiral (S) |
| 24 | H | CH$_2$ | CH$_2$ | H, H | OtBu | 4-Cl—Ph | 4-Cl—Ph | H | — |
| 25 | H | — | — | H, Me | OH, | 4-Cl—Ph | 4-Cl—Ph | 5-F | Na salt Chiral (S) |
| 26 | H | — | — | H, Me | NHMe | 4-Cl—Ph | 4-Cl—Ph | 5-F | Chiral (S) |
| 27 | H | — | — | H, CH(OH)Me | NH$_2$ | 4-Cl—Ph | 4-Cl—Ph | H | Chiral (1S, 2R) |
| 28 | H | CH$_2$ | CH$_2$ | H, H | NH$_2$ | 4-Cl—Ph | 4-Cl—Ph | 5-F | — |
| 29 | H | — | — | H, H | OH | 4-Cl—Ph | 4-Cl—Ph | H | — |
| 30 | H | — | — | H, Me | NH$_2$ | 4-Cl—Ph | 4-Cl—Ph | 2-F | Chiral (S) |
| 31 | H | — | — | H, Me | NHMe | 4-Cl—Ph | 4-Cl—Ph | 2-F | Chiral (S) |
| 32 | H | — | — | H, Me | NH$_2$ | 4-Cl—Ph | 4-Cl—Ph | 6-F | Chiral (S) |
| 33 | H | — | — | H, Et | NH$_2$ | 4-Cl—Ph | 4-Cl—Ph | 6-F | Chiral (S) |
| 34 | H | — | — | H, iPr | NH$_2$ | 4-Cl—Ph | 4-Cl—Ph | 6-F | Chiral (S) |
| 35 | H | — | — | H, Me | NHMe | 4-Cl—Ph | 4-Cl—Ph | 6-F | Chiral (S) |
| 36 | H | — | — | H, Et | NH$_2$ | 4-Cl—Ph | 4-Cl—Ph | 4-F | Chiral (S) |
| 37 | H | — | — | H, H | NH$_2$ | 4-Cl—Ph | 4-Cl—Ph | 5-Me | — |
| 38 | H | — | — | H, Me | NH$_2$ | 4-Cl—Ph | 4-Cl—Ph | 5-Me | Chiral (S) |
| 39 | H | — | — | H, Et | NH$_2$ | 4-Cl—Ph | 4-Cl—Ph | 5-Me | Chiral (S) |
| 40 | H | — | — | H, iPr | NH$_2$ | 4-Cl—Ph | 4-Cl—Ph | 5-Me | Chiral (S) |
| 41 | H | — | — | H, Me | NHMe | 4-Cl—Ph | 4-Cl—Ph | 5-Me | Chiral (S) |
| 42 | H | — | — | H, CH$_2$OH | NH$_2$ | 4-Cl—Ph | 4-Cl—Ph | 5-Me | Chiral (S) |
| 43 | H | — | — | H, Me | NH$_2$ | 4-Cl—Ph | 4-Cl—Ph | 5-Cl | Chiral (S) |
| 44 | H | — | — | H, Et | NH$_2$ | 4-Cl—Ph | 4-Cl—Ph | 5-Cl | Chiral (S) |
| 45 | H | — | — | H, iPr | NH$_2$ | 4-Cl—Ph | 4-Cl—Ph | 5-Cl | Chiral (S) |
| 46 | H | — | — | H, Me | NHMe | 4-Cl—Ph | 4-Cl—Ph | 5-Cl | Chiral (S) |
| 47 | H | — | — | H, CH$_2$OH | NH$_2$ | 4-Cl—Ph | 4-Cl—Ph | 5-Cl | Chiral (S) |
| 48 | H | — | — | H, Me | NH$_2$ | 4-Cl—Ph | 4-Cl—Ph | 5-Br | Chiral (S) |
| 49 | H | — | — | H, Et | NH$_2$ | 4-Cl—Ph | 4-Cl—Ph | 5-Br | Chiral (S) |
| 50 | H | — | — | H, iPr | NH$_2$ | 4-Cl—Ph | 4-Cl—Ph | 5-Br | Chiral (S) |
| 51 | H | — | — | H, Me | NHMe | 4-Cl—Ph | 4-Cl—Ph | 5-Br | Chiral (S) |
| 52 | H | — | — | H, CH$_2$OH | NH$_2$ | 4-Cl—Ph | 4-Cl—Ph | 5-Br | Chiral (S) |
| 53 | H | — | — | H, H | NH$_2$ | 4-Cl—Ph | 4-Cl—Ph | 5-CF$_3$ | — |
| 54 | H | — | — | H, Me | NH$_2$ | 4-Cl—Ph | 4-Cl—Ph | 5-CF$_3$ | Chiral (S) |
| 55 | H | — | — | H, Et | NH$_2$ | 4-Cl—Ph | 4-Cl—Ph | 5-CF$_3$ | Chiral (S) |
| 56 | H | — | — | H, iPr | NH$_2$ | 4-Cl—Ph | 4-Cl—Ph | 5-CF$_3$ | Chiral (S) |
| 57 | H | — | — | H, Me | NHMe | 4-Cl—Ph | 4-Cl—Ph | 5-CF$_3$ | Chiral (S) |
| 58 | H | — | — | H, CH$_2$OH | NH$_2$ | 4-Cl—Ph | 4-Cl—Ph | 5-CF$_3$ | Chiral (S) |
| 59 | H | — | — | H, Me | NH$_2$ | 4-Cl—Ph | 4-Cl—Ph | 5-CN | Chiral (S) |
| 60 | H | — | — | H, Et | NH$_2$ | 4-Cl—Ph | 4-Cl—Ph | 5-CN | Chiral (S) |
| 61 | H | — | — | H, iPr | NH$_2$ | 4-Cl—Ph | 4-Cl—Ph | 5-CN | Chiral (S) |
| 62 | H | — | — | H, Me | NHMe | 4-Cl—Ph | 4-Cl—Ph | 5-CN | Chiral (S) |
| 63 | H | — | — | H, CH$_2$OH | NH$_2$ | 4-Cl—Ph | 4-Cl—Ph | 5-CN | Chiral (S) |
| 64 | H | — | — | H, Me | OH | 4-Cl—Ph | 4-Cl—Ph | 6-F | CF$_3$CO$_2^-$ salt Chiral (S) |
| 65 | H | — | — | H, Me | OH | 4-Cl—Ph | 4-Cl—Ph | 5-Me | CF$_3$CO$_2^-$ salt Chiral (S) |
| 66 | H | — | — | H, Me | OH | 4-Cl—Ph | 4-Cl—Ph | 5-Cl | CF$_3$CO$_2^-$ salt Chiral (S) |

TABLE 1-continued

| N° | R1 | A | B | R2, R3 | R' | R6 | R7 | Y | Salt/chirality |
|---|---|---|---|---|---|---|---|---|---|
| 67 | H | — | — | H, Me | OH | 4-Cl—Ph | 4-Cl—Ph | 5-Br | CF$_3$CO$_2^-$ salt Chiral (S) |
| 68 | H | — | — | H, Me | OH | 4-Cl—Ph | 4-Cl—Ph | 5-CF$^3$ | CF$_3$CO$_2^-$ salt Chiral (S) |
| 69 | H | — | — | H, Me | OH | 4-Cl—Ph | 4-Cl—Ph | 5-CN | CF$_3$CO$_2^-$ salt Chiral (S) |
| 70 | H | — | — | H, Me | NH$_2$ | 4-Br—Ph | 4-Br—Ph | 5-F | Chiral (S) |
| 71 | H | — | — | H, Me | NH$_2$ | 4-CF$_3$—Ph | 4-CF$_3$—Ph | 5-F | Chiral (S) |
| 72 | H | — | — | H, Me | NH$_2$ | 4-CN—Ph | 4-CN—Ph | 5-F | Chiral (S) |
| 73 | H | — | — | H, Me | NH$_2$ | 4-MeO—Ph | 4-MeO—Ph | 5-F | Chiral (S) |
| 74 | H | — | — | H, Me | NH$_2$ | 4-F—Ph | 4-F—Ph | 5-F | Chiral (S) |
| 75 | H | — | — | H, Me | OMe | 4-Cl—Ph | 4-Cl—Ph | 5-F | Chiral (S) |
| 76 | H | — | — | H, Et | NH$_2$ | 4-Me—Ph | 4-Me—Ph | 5-F | Chiral (S) |
| 77 | H | — | — | H, Me | NHMe | 4-Br—Ph | 4-Br—Ph | 5-F | Chiral (S) |
| 78 | H | — | — | H, Me | OH | 4-Br—Ph | 4-Br—Ph | 5-F | Chiral (S) |
| 79 | H | — | — | H, Me | OEt | 4-Cl—Ph | 4-Cl—Ph | 5-F | Chiral (S) |
| 80 | H | — | — | H, Et | NH$_2$ | 4-OCF$_3$—Ph | 4-OCF$_3$—Ph | 5-F | Chiral (S) |

TABLE 1A

| No. | Characterizations |
|---|---|
| 1 | Mp.: 229° C.; 1H NMR spectrum (300 MHz; (δ in ppm); (DMSO-d6); referenced at 2.50 ppm): 1.34 (d, J = 7.1 Hz, 3H); 2.71 (t, J = 6.8 Hz, 2H); 2.97 (s, 3H); 3.26-3.38 (m partially masked, 2H); 4.38 (s, 1H); 4.42 (m, 1 H); 4.73 (quin, J = 6.8 Hz, 1H); 6.98 (broad s, 1H); 7.31 (d, J = 8.5 Hz, 4H); 7.36 (d, J = 8.5 Hz, 4H); 7.39 (broad s, 1H); 7.44-7.54 (m, 2H); 7.80 (broad s, 1H); 7.89 (m, 1H); 8.50 (d, J = 7.4 Hz, 1H); Mass spectrum: ES m/z = 575 (MH$^+$, base peak), m/z = 235 (C$_{13}$H$_9$Cl$_2^+$), m/z = 573 (MH$^-$); Elemental analysis: Calculated: C: 56.35%- H: 4.90%- N: 9.73%- S: 5.57%; Measured: C: 56.72%- H: 4.99%- N: 9.50%- S: 5.65%; Optical rotation: α$_D$ = +10.3 (c = 0.428, MeOH) |
| 2 | Mp.: 154-156° C.; 1H NMR spectrum (400 MHz; (δ in ppm); (DMSO-d6); referenced at 2.50 ppm): 2.73 (t, J = 7.0 Hz, 2H); 3.00 (s, 3H); 3.36 (m, 2H); 3.81 (d, J = 5.9 Hz, 2H); 4.40 (s, 1H); 4.72 (m, 1H); 7.04 (broad s, 1H); 7.31 (d, J = 8.8 Hz, 4H); 7.35 (d, J = 8.8 Hz, 4H); 7.37-7.47 (m, 2H); 7.60-7.73 (m, 2H); 8.84 (t, J = 5.9 Hz, 1H); Mass spectrum: ES m/z = 579 (MH$^+$, base peak), m/z = 235 (C$_{13}$H$_9$Cl$_2^+$); Elemental analysis: Calculated: C: 53.89%- H: 4.35%- N: 9.67%- S: 5.53%; Measured: C: 53.88%- H: 4.71%- N: 9.16%- S: 5.66% |
| 3 | Mp.: 228-230° C.; 1H NMR spectrum (400 MHz; (δ in ppm); (DMSO-d6); referenced at 2.50 ppm): 1.33 (d, J = 7.3 Hz, 3H); 2.73 (t, J = 6.8 Hz, 2H); 3.00 (s, 3H); 3.24-3.43 (m partially masked, 2H); 4.34-4.48 (m, 2H); 4.72 (quin, J = 6.8 Hz, 1H); 6.99 (broad s, 1H); 7.31 (d, J = 8.5 Hz, 4H); 7.37 (d, J = 8.5 Hz, 4H); 7.39-7.45 (m, 2H); 7.67 (broad s, 1H); 7.74 (broad d, J = 8.8 Hz, 1H); 8.61 (d, J = 7.3 Hz, 1H); Mass spectrum: ES m/z = 593 (MH$^+$, base peak), m/z = 637 (MH$^-$ + HCO$_2$H), m/z = 591 (MH$^-$, base peak); Elemental analysis: Calculated: C: 54.64%- H: 4.59%- N: 9.44%- S: 5.40%; Measured: C: 54.09%- H: 4.66%- N: 9.34%- S: 5.43%- H$_2$O = 1.71%; Optical rotation: α$_D$ = +11.3 (c = 0.365, MeOH) |
| 4 | Mp.: 219-221° C.; 1H NMR spectrum (400 MHz; (δ in ppm); (DMSO-d6); referenced at 2.50 ppm): 1.33 (d, J = 6.8 Hz, 3H); 2.73 (t, J = 7.1 Hz, 2H); 3.00 (s, 3H); 3.35 (m, 2H); 4.35-4.45 (m, 2H); 4.73 (quin, J = 6.8 Hz, 1H); 6.99 (broad s, 1H); 7.31 (d, J = 8.8 Hz, 4H); 7.37 (d, J = 8.8 Hz, 4H); 7.39-7.45 (m, 2H); 7.68 (t, J = 1.7 Hz, 1H); 7.74 (dt, J = 9.0; 1.7 Hz, 1H); 8.62 (d, J = 7.8 Hz, 1H); Mass spectrum: ES m/z = 593 (MH$^+$, base peak), m/z = 235 (C$_{13}$H$_9$Cl$_2^+$); Elemental analysis: Calculated: C: 54.64%- H: 4.59%- N: 9.44%- S: 5.40%; Measured: C: 54.44%- H: 4.54%- N: 9.48%- S: 5.36%-H$_2$O < 0.1%; Optical rotation: α$_D$ = −23.3 (c = 0.476, DMSO) |
| 5 | Mp.: 235° C.; 1H NMR spectrum (300 MHz; (δ in ppm); (DMSO-d6); referenced at 2.50 ppm): 1.34 (d, J = 7.3 Hz, 3H); 2.71 (t, J = 6.8 Hz, 2H); 2.97 (s, 3H); 3.32 (m masked, 2H); 4.38 (s, 1H); 4.42 (m, 1H); 4.74 (quin, J = 6.8 Hz, 1H); 6.98 (broad s, 1H); 7.31 (d, J = 8.8 Hz, 4H); 7.36 (d, J = 8.8 Hz, 4H); 7.39 (broad s, 1H); 7.45-7.54 (m, 2H); 7.80 (broad s, 1H); 7.88 (m, 1H); 8.50 (d, J = 7.6 Hz, 1H); Mass spectrum: ES m/z = 575 (MH$^+$, base peak), m/z = 235 (C$_{13}$H$_9$Cl$_2^+$); Elemental analysis: Calculated: C: 56.35%- H: 4.90%- N: 9.73%- S: 5.57%; Measured: C: 56.84%- H: 5.17%- N: 9.56%- S: 5.51%; Optical rotation: α$_D$ = −6.6 (c = 0.493, DMSO) |
| 6 | Mp.: 245-247° C.; 1H NMR spectrum (400 MHz; (δ in ppm); (DMSO-d6); referenced at 2.50 ppm): 2.71 (t, J = 6.9 Hz, 2H); 2.97 (s, 3H); 3.33 (m masked, 2H); 3.71 (m, 2H); 4.38 (s, 1H); 4.44 (m, 1H); 4.75 (quin, J = 6.9 Hz, 1H); 4.93 (broad t, J = 5.9 Hz, 1H); 7.10 (broad s, 1H); 7.31 (d, J = 8.8 Hz, 4H); 7.36 (d, J = 8.8 Hz, 4H); 7.41 (broad s, 1H); 7.45-7.55 (m, 2H); 7.81 (broad s, 1H); 7.88 (m, 1H); 8.30 (d, J = 7.8 Hz, 1H); Mass spectrum: ES m/z = 591 (MH$^+$, base peak), m/z = 235 (C$_{13}$H$_9$Cl$_2^+$); Elemental analysis: Calculated: C: 54.83%- H: 4.77%- N: 9.47%- S: 5.42%; Measured: C: 53.60%- H: 5.04%- N: 9.00%- S: 4.90%-H$_2$O = 1.45%; Optical rotation: α$_D$ = +30.9 (c = 0.412, DMSO) |
| 7 | Mp.: 190-192° C.; 1H NMR spectrum (400 MHz; (δ in ppm); (DMSO-d6); referenced at 2.50 ppm): 2.35 (t, J = 7.1 Hz, 2H); 2.69 (t, J = 6.9 Hz, 2H); 2.95 (s, 3H); 3.34 (t, J = 6.9 Hz, 2H); 3.44 (m, 2H); 4.37 (s, 1H); 4.73 (quin, J = 6.9 Hz, 1H); 6.81 (broad s, 1H); 7.31 (d, J = 8.8 Hz, 4H); 7.35 (s masked, 1H); 7.36 (t, J = 8.8 Hz, 4H); 7.41-7.52 (m, 2H); 7.74 (broad s, 1H); 7.80 (m, 1H); 8.58 (t, J = 5.6 Hz, 1H); Mass spectrum: ES m/z = 575 (MH$^+$, base peak), m/z = 235 (C$_{13}$H$_9$Cl$_2^+$); Elemental analysis: Calculated: C: 56.35%- H: 4.90%- N: 9.73%- S: 5.57%; Measured: C: 56.36%- H: 5.10%- N: 9.46%- S: 5.29%-H$_2$O = 0.34% |
| 8 | Mp.: 176° C.; 1H NMR spectrum (400 MHz; (δ in ppm); (DMSO-d6); referenced at 2.50 ppm): 2.71 (t, J = 6.9 Hz, 2H); 2.97 (s, 3H); 3.34 (t, J = 6.9 Hz, 2H); 3.48 (m, 4H); 3.58 (m, 4H); 4.13 (d, J = 5.5 Hz, 2H); 4.37 (s, 1H); 4.74 (quin, J = 6.9 Hz, 1H); 7.31 (d, J = 8.8 Hz, 4H); 7.35 (d, J = 8.8 Hz, 4H); 7.47-7.55 (m, 2H); 7.78 (broad s, 1H); 7.85 (m, 1H); 8.66 (t, J = 5.5 Hz, 1H); Mass spectrum: ES m/z = 631 (MH$^+$, base peak), m/z = 235 (C$_{13}$H$_9$Cl$_2^+$); Elemental analysis: Calculated: C: 57.05%- H: 5.11%- N: 8.87%- S: 5.08%; Measured: C: 57.29%- H: 4.96%- N: 8.29%- S: 4.93% |
| 9 Pathway A | Mp.: 171-173° C.; 1H NMR spectrum (400 MHz; (δ in ppm); (DMSO-d6); referenced at 2.50 ppm): 1.32 (d, J = 7.0 Hz, 3H); 2.59 (d, J = 4.9 Hz, 3H); 2.71 (t, J = 7.6 Hz, 2H); 2.97 (s, 3H); 3.33 (t, J = 7.6 Hz partially masked, 2H); 4.38 (s, 1H); 4.44 (m, 1H); 4.74 (m, 1H); 7.31 (d, J = 8.5 Hz, 4H); 7.35 (d, J = 8.5 Hz, 4H); 7.44- 7.52, (m, 2H); 7.80 (s, 1H); 7.83-7.91 (m, 2H); 8.59 (d, J = 7.8 Hz, 1H); Mass spectrum: ES m/z = 589 (MH$^+$, base peak); Elemental analysis: Calculated: C: 57.05%- H: 5.13%- N: 9.50%- S: 5.44%; Measured: C: 55.49%- H: 5.50%- N: 9.14%- S: 5.10%-H$_2$O = 2.57%; Optical rotation: α$_D$ = +25.4 (c = 0.427, DMSO) |
| 9 Pathway B | 1H NMR spectrum (400 MHz; (δ in ppm); (DMSO-d6); referenced at 2.50 ppm): 1.32 (d, J = 7.1 Hz, 3H); 2.59 (d, J = 4.6 Hz, 3H); 2.71 (t, J = 7.3 Hz, 2H); 2.97 (s, 3H); 3.33 (t, J = 7.3 Hz, 2H); 4.38 (s, 1H); 4.44 (m, 1H); 4.74 (m, 1H); 7.30 (d, J = 8.6 Hz, 4H); 7.35 (d, J = 8.6 Hz, 4H); 7.45-7.53 (m, 2H); 7.80 (broad s, 1H); 7.82-7.92 (m, 2H); 8.57 (d, J = 7.3 Hz, 1H); |

TABLE 1A-continued

| No. | Characterizations |
|---|---|
|  | Mass spectrum: ES m/z = 589 (MH+, base peak); Elemental analysis: Calculated: C: 57.05%- H: 5.13%- N: 9.50%- S: 5.44%; Measured: C: 56.83%- H: 5.51%- N: 8.95%- S: 4.99%- H₂O = 0.57%; Optical rotation: α_D = +25.9 (c = 0.415, DMSO) |
| 10 | Mp.: 220-222° C.; 1H NMR spectrum (400 MHz; (δ in ppm); (DMSO-d6); referenced at 2.50 ppm): 0.90 (t, J = 7.3 Hz, 3H); 1.63-1.86 (m, 2H); 2.71 (t, J = 6.9 Hz, 2H); 2.97 (s, 3H); 3.31 (m masked, 2H); 4.32 (m, 1H); 4.38 (s, 1H); 4.74 (quin, J = 6.9 Hz, 1H); 7.01 (broad s, 1H); 7.30 (d, J = 8.8 Hz, 4H); 7.36 (d, J = 8.8 Hz, 4H); 7.42 (broad s, 1H); 7.45-7.56 (m, 2H); 7.80 (broad s, 1H); 7.88 (m, 1H); 8.40 (d, J = 7.8 Hz, 1H); Mass spectrum: ES m/z = 589 (MH+, base peak), m/z = 235 (C₁₃H₉Cl₂+·); Elemental analysis: Calculated: C: 57.05%- H: 5.13%- N: 9.50%- S: 5.44%; Measured: C: 56.59%- H: 5.43%- N: 9.20%- S: 4.93%-H₂O = 0.56%; Optical rotation: α_D = +17.4 (c = 0.427, MeOH) |
| 11 | 1H NMR spectrum (400 MHz; (δ in ppm); (DMSO-d6); referenced at 2.50 ppm): 0.88 (d, J = 6.4 Hz, 3H); 0.90 (d, J = 6.4 Hz, 3H); 1.50-1.73 (m, 2H); 2.71 (m, 2H); 2.97 (s, 3H); 3.33 (m, 2H); 4.37 (s, 1H); 4.46 (m, 1H); 4.74 (quin, J = 6.9 Hz, 1H); 6.97 (broad s, 1H); 7.30 (d, J = 8.8 Hz, 4H); 7.35 (d, J = 8.8 Hz, 4H); 7.42 (broad s, 1H); 7.45-7.55 (m, 2H); 7.81 (broad s, 1H); 7.90 (m, 1H); 8.46 (d, J = 8.2 Hz, 1H); Mass spectrum: ES m/z = 617 (MH+, base peak); Elemental analysis: Calculated: C: 58.34%- H: 5.55%- N: 9.07%- S: 5.19%; Measured: C: 58.74%- H: 5.68%- N: 8.69%- S: 4.77%; Optical rotation: α_D = +20.5 (c = 0.401, DMSO) |
| 12 | Mp.: 197-199° C.; 1H NMR spectrum (400 MHz; (δ in ppm); (DMSO-d6); referenced at 2.50 ppm): 0.91 (d, J = 6.8 Hz, 3H); 0.93 (d, J = 6.8 Hz, 3H); 2.10 (m, 1H); 2.74 (t, J = 7.2 Hz, 2H); 3.00 (s, 3H); 3.35 (t, J = 7.2 Hz, 2H); 4.26 (m, 1H); 4.41 (s, 1H); 4.73 (m, 1H); 7.06 (broad s, 1H); 7.31 (d, J = 8.3 Hz, 4H); 7.36 (d, J = 8.3 Hz, 4H); 7.42 (dt, J = 9.3; 2.2 Hz, 1H); 7.48 (broad s, 1H); 7.67 (t, J = 2.2 Hz, 1H); 7.76 (dt, J = 9.3; 2.2 Hz, 1H); 8.38 (d, J = 8.3 Hz, 1H); Mass spectrum: ES m/z = 621 (MH+, base peak); Elemental analysis: Calculated: C: 56.04%- H: 5.03%- N: 9.01%- S: 5.16%; Measured: C: 55.96%- H: 4.67%- N: 9.07%- S: 5.31%; Optical rotation: α_D = +12.1 (c = 0.480, DMSO) |
| 13 | Mp.: 212-214° C.; 1H NMR spectrum (400 MHz; (δ in ppm); (DMSO-d6); referenced at 2.50 ppm): 2.73 (t, J = 7.6 Hz, 2H); 3.00 (s, 3H); 3.36 (t, J = 7.6 Hz, 2H); 3.72 (m, 2H); 4.41 (s, 1H); 4.43 (m, 1H); 4.73 (m, 1H); 4.91 (broad m, 1H); 7.10 (broad s, 1H); 7.32 (d, J = 8.4 Hz, 4H); 7.37 (d, J = 8.4 Hz, 4H); 7.41-7.46 (m, 2H); 7.68 (broad s, 1H); 7.75 (broad d, J = 9.1 Hz, 1H); 8.44 (d, J = 8.3 Hz, 1H); Mass spectrum: ES m/z = 609 (MH+, base peak); Elemental analysis: Calculated: C: 53.21%- H: 4.47%- N: 9.19%- S: 5.26%; Measured: C: 53.01%- H: 4.43%- N: 9.09%- S: 5.01%; Optical rotation: α_D = +29.5 (c = 0.386, DMSO) |
| 14 | Mp.: 212-214° C.; 1H NMR spectrum (400 MHz; (δ in ppm); (DMSO-d6); referenced at 2.50 ppm): 0.90 (t, J = 7.3 Hz, 3H); 1.68 (m, 1H); 1.81 (m, 1H); 2.74 (t, J = 7.3 Hz, 2H); 3.00 (s, 3H); 3.35 (m partially masked, 2H); 4.30 (m, 1H); 4.41 (s, 1H); 4.73 (m, 1H); 7.02 (broad s, 1H); 7.31 (d, J = 8.3 Hz, 4H); 7.36 (d, J = 8.3 Hz, 4H); 7.39-7.47 (m, 2H); 7.68 (broad s, 1H); 7.76 (broad d, J = 9.3 Hz, 1H); 8.51 (d, J = 8.3 Hz, 1H); Mass spectrum: ES m/z = 607 (MH+, base peak); Elemental analysis: Calculated: C: 55.36%- H: 4.81%- N: 9.22%- S: 5.28%; Measured: C: 55.34%- H: 4.86%- N: 9.21%- S: 4.87%; Optical rotation: α_D = +19.7 (c = 0.547, DMSO) |
| 15 | Mp.: 216° C.; 1H NMR spectrum (400 MHz; (δ in ppm); (DMSO-d6); referenced at 2.50 ppm): 2.60 (d, J = 4.6 Hz, 3H); 2.71 (t, J = 7.5 Hz, 2H); 2.98 (s, 3H); 3.34 (m masked, 2H); 3.83 (d, J = 6.1 Hz, 2H); 4.39 (s, 1H); 4.73 (m, 1H); 7.32 (d, J = 8.3 Hz, 4H); 7.37 (d, J = 8.3 Hz, 4H); 7.45-7.56 (m, 2H); 7.80 (broad s, 1H); 7.82-7.90 (m, 2H); 8.84 (t, J = 6.1 Hz, 1H); Mass spectrum: ES m/z = 575 (MH+, base peak); Elemental analysis: Calculated: C: 56.35%- H: 4.90%- N: 9.73%- S: 5.57%; Measured: C: 56.72%- H: 4.89%- N: 9.65%- S: 5.29% |
| 16 | Mp.: 196-198° C.; 1H NMR spectrum (400 MHz; (δ in ppm); (DMSO-d6); referenced at 2.50 ppm): 2.71 (t, J = 7.2 Hz, 2H); 2.97 (s, 3H); 3.34 (m, 2H); 3.82 (d, J = 5.9 Hz, 2H); 4.37 (s, 1H); 4.73 (m, 1H); 7.02 (broad s, 1H); 7.30 (d, J = 8.8 Hz, 4H); 7.35 (d, J = 8.8 Hz, 4H); 7.37 (broad s, 1H); 7.45-7.54 (m, 2H); 7.79 (t, J = 1.8 Hz, 1H); 7.86 (dt, J = 7.0; 1.8 Hz, 1H); 8.73 (t, J = 5.9 Hz, 1H); Mass spectrum: ES m/z = 561 (MH+, base peak); Elemental analysis: Calculated: C: 55.62%- H: 4.67%- N: 9.98%- S: 5.71%- Cl: 12.63%; Measured: C: 55.33%- H: 4.64%- N: 9.68%- S: 5.78%- Cl: 13.08%-H₂O < 0.10% |
| 17 | 1H NMR spectrum (400 MHz; (δ in ppm); (DMSO-d6); referenced at 2.50 ppm): 1.38 (m masked, 3H); 1.39 (s, 9H); 2.71 (m, 2H); 2.97 (s, 3H); 3.34 (m partially masked, 2H); 4.35 (m, 1H); 4.37 (s, 1H); 4.74 (m, 1H); 7.30 (d, J = 8.5 Hz, 4H); 7.34 (d, J = 8.5 Hz, 4H); 7.43-7.55 (m, 2H); 7.79 (broad s, 1H); 7.86 (m, 1H); 8.72 (d, J = 7.3 Hz, 1H); Mass spectrum: ES m/z = 632 (MH+, base peak); Optical rotation: α_D = +3.6 (c = 0.448, DMSO) |
| 18 | 1H NMR spectrum (400 MHz; (δ in ppm); (DMSO-d6); referenced at 2.50 ppm): 1.39 (d, J = 7.3 Hz, 3H); 2.71 (m, 2H); 2.97 (s, 3H); 3.23-3.45 (m masked, 2H); 4.38 (s, 1H); 4.39 (m, 1H); 4.74 (m, 1H); 7.30 (d, J = 8.3 Hz, 4H); 7.35 (d, J = 8.3 Hz, 4H); 7.44-7.56 (m, 2H); 7.80 (broad s, 1H); 7.86 (m, 1H); 8.70 (d, J = 7.3 Hz, 1H); Mass spectrum: ES m/z = 576 (MH+, base peak); Elemental analysis: Calculated: C: 56.25%- H: 4.72%- N: 7.29%- S: 5.56% Measured: C: 55.68%- H: 4.99%- N: 6.89%- S: 5.01%-H₂O = 0.82%; Optical rotation: α_D = +10 (c = 0.195, DMSO) |
| 19 | Elemental analysis: Calculated: C: 58.25%- H: 5.38%- N: 6.79%- S: 5.18% Measured: C: 57.38%- H: 5.93%- N: 6.58%- S: 4.74%-H₂O = 1.49%; Mass spectrum: ES m/z = 618 (MH+), m/z = 616 (M − H)−, m/z = 662 ([M + HCO₂H − H]−, base peak) |
| 20 | Elemental analysis: Calculated: C: 57.83%- H: 5.46%- N: 6.32%- S: 4.82% Measured: C: 57.65%- H: 5.80%- N: 6.17%- S: 4.68%; Mass spectrum: ES m/z = 664 (MH+), m/z = 662 (M − H)−, m/z = 708 ([M + HCO₂H − H]−, base peak) |
| 21 | Optical rotation: α_D = +8.6 +/− 0.6 (c = 0.401, DMSO); Mass spectrum: ES m/z = 650(MH+), m/z = 648 (M − H)−, m/z = 694 ([M + HCO₂H − H]−, base peak) |
| 22 | Mp.: 183-185° C.; Elemental analysis: Calculated: C: 55.54%- H: 4.99%- N: 9.25%- S: 5.30% Measured: C: 54.77%- H: 5.04%- N: 8.99%- S: 4.80%-H₂O = 0.98%; Optical rotation: α_D = +27.7 (c = 0.406, DMSO) |
| 23 | Optical rotation: α_D = +8.1 +/− 0.7 (c = 0.417, DMSO); Mass spectrum: ES m/z = 603 (MH+), m/z = 601 (M − H)−, m/z = 647 ([M + HCO₂H − H]−, base peak) |
| 24 | Elemental analysis: Calculated: C: 59.44%- H: 5.77%- N: 6.50%- S: 4.96%- Cl: 10.97% Measured: C: 59.27%- H: 5.93%- N: 6.41%- S: 4.67%- Cl: 11.13%; Mass spectrum: ES m/z = 646 (MH+) |
| 25 | Optical rotation: α_D = +24.2 +/− 0.7 (c = 0.435, DMSO); Mass spectrum: ES m/z = 594 (MH+), m/z = 592 (M − H)−, m/z = 1185 (2M − H)− |
| 26 | Mp.: 150° C.; Elemental analysis: Calculated: C: 55.36%- H: 4.81%- N: 9.22%- S: 5.28% Measured: C: 55.35%- H: 5.02%- N: 8.82%- S: 4.88%; Optical rotation: α_D = +29.2 (c = 0.363, DMSO) |
| 27 | Elemental analysis: Calculated: C: 55.54%- H: 4.99%- N: 9.25%- S: 5.30% Measured: C: 55.43%- H: 5.20%- N: 8.85%- S: 4.88%; Optical rotation: α_D = +25.0 (c = 0.447, DMSO) |
| 28 | Mp.: 186° C.; Elemental analysis: Calculated: C: 55.36%- H: 4.81%- N: 9.22%- S: 5.28% Measured: C: 55.10%- H: 5.09%- N: 8.98%- S: 4.92% |
| 29 | Elemental analysis: Calculated: C: 55.52%- H: 4.48%- N: 7.47%- S: 5.70% Measured: C: 54.98%- H: 4.92%- N: 6.75%- S: 5.08%-H₂O = 1.97%; Mass spectrum: ES m/z = 562 (MH+, base peak), m/z = 1123 (2M − H)− |
| 30 | 1H NMR spectrum (500 MHz; (δ in ppm); (DMSO-d6)); referenced at 2.50 ppm), for this batch, we observe a 50-50 mixture of rotamers with: 1.30 (d, J = 7.2 Hz, 1.5H); 1.31 (d, J = 7.2 Hz, 1.5H); 2.61-2.69 (m, 1H); 2.75 (t, J = 7.1 Hz, 1H); 3.10 (s, 1.5H); 3.12 (s, 1.5 H); 3.33 (m partially masked, 2H); 4.32 (s, 0.5H); 4.33 (s, 0.5 H); 4.41 (m, 1H); 4.70 (m, 1H); 7.10 (broad s, 1H); 7.29-7.37 (m, 9H); 7.46 (m, 1H); 7.58 (m, 1H); 7.68 (m, 1H); 8.42 (dd, J = 7.4; 2.2Hz, 0.5 H); 8.47 (dd, J = 7.4; 2.2 Hz, 0.5H); Mass spectrum: ES m/z = 593 [M + H]+, m/z = 591 [M − H]−; Optical rotation: α_D = +31.3 (c = 0.5716, DMSO) |
| 31 | 1H NMR spectrum (500 MHz; (δ in ppm); (DMSO-d6)), this is a 50-50 mixture of rotamers with: 1.29 (resolved d, J = 6.7 Hz, 3H); 2.59-2.71 (m, 4H); 2.77 (t, J = 7.0 Hz, 1H); 3.10 (s, 1.5H); 3.12 (s, 1.5H); 3.33 (m, 2H); 4.32 (s, 0.5H); 4.33 (s, 0.5H); 4.42 (m, 1H); 4.70 (m, 1H); 7.23-7.36 (m, 9H); 7.58 (m, 1H); 7.68 (m, 1H); 7.92 (m, 1H) 8.42-8.53 (m, 1H); Mass spectrum: |

TABLE 1A-continued

| No. | Characterizations |
|---|---|
| | ES m/z = 607 [M+H]$^+$, m/z = 605 [M − H]$^−$; Optical rotation: $\alpha_D$ = +25.8 (c = 0.562, DMSO) |
| 32 | 1H NMR spectrum (500 MHz; (δ in ppm); (DMSO-d6)): 1.32 (d, J = 7.1 Hz, 3H); 2.71 (J = 7.1 Hz, 2H); 2.97 (s, 3H); 3.33 (partially masked, 2H); 4.41 (m, 2H); 4.71 (m, 1H); 7.09 (broad s, 1H); 7.27-7.34 (m, 5H); 7.36 (d, J = 8.5 hz, 4H); 7.44 (broad s, 1H); 7.48 (ddd, J = 8.9; 4.5; 2.8 Hz, 1H); 7.59 (dd, J = 6.4; 2.8 Hz, 1H); 8.32 (dd, J = 7.4; 3.8 Hz, 1H); Mass spectrum: ES m/z = 593 [M + H]$^+$, m/z = 591 [M − H]$^−$; Optical rotation: $\alpha_D$ = +18.0 (c = 0.549, DMSO) |
| 33 | 1H NMR spectrum (500 MHz; (δ in ppm); (DMSO-d6)): 0.89 (t, J = 7.4 Hz, 3H); 1.65 (m, 1H); 1.80 (m, 1H); 2.71 (m, 2H); 2.97 (s, 3H); 3.32 (m partially masked, 2H); 4.35 (m, 1H); 4.40 (s, 1H); 4.72 (m, 1H); 7.11 (broad s, 1H); 7.24-7.34 (m, 5H); 7.35-7.40 (d, J = 8.5 Hz, 4H); 7.43-7.52 (m, 2H); 7.57 (dd, J = 6.3; 3.0 Hz, 1H); 8.24 (dd, J = 6.3; 2.6 Hz, 1H); Mass spectrum: ES m/z = 607 [M + H]$^+$, m/z = 605 [M − H]$^−$; Optical rotation: $\alpha_D$ = +16.8 (c = 0.578, DMSO) |
| 34 | 1H NMR spectrum (500 MHz; (δ in ppm); (DMSO-d6)): 0.89 (d, J = 6.8 Hz, 3H); 0.93 (d, J = 6.8 Hz, 3H); 2.06 (m, 1H); 2.71 (t, J = 7.6 Hz, 2H); 2.96 (s, 3H); 3.32 (m partially masked, 2H); 4.33 (dd, J = 8.8; 6.7 Hz, 1H); 4.41 (s, 1H); 4.72 (m, 1H); 7.12 (broad s, 1H); 7.30-7.33 (m, 5H); 7.36 (d, J = 8.5 Hz, 4H); 7.45-7.52 (m, 2H); 7.54 (dd, J = 6.3; 2.7 Hz, 1H); 8.14 (dd, J = 8.7; 3.7 Hz, 1H); Mass spectrum: ES m/z = 621 [M + H]$^+$, m/z = 619 [M − H]$^−$; Optical rotation: $\alpha_D$ = +17.7 (c = 0.499, DMSO) |
| 35 | 1H NMR spectrum (500 MHz; (δ in ppm); (DMSO-d6)): 1.29 (d, J = 7.1 Hz, 3H); 2.62 (d, J = 4.7 Hz, 3H); 2.71 (t, J = 7.5 Hz, 2H); 2.97 (s, 3H); 3.32 (m, partially masked, 2H); 4.40 (s, 1H); 4.43 (m, 1H); 4.71 (m, 1H); 7.30-7.34 (m, 5H); 7.36 (d, J = 8.5 Hz, 4H); 7.48 (ddd, J = 8.9; 4.4; 2.9 Hz, 1H); 7.57 (dd, J = 6.3; 2.9 Hz, 1H); 7.93 (q, J = 4.7 Hz, 1H); 8.38 (dd, J = 7.2; 3.3 Hz, 1H); Mass spectrum: Es m/z = 607 [M + H]+, m/z = 605 [M − H]−; Optical rotation: $\alpha_D$ = +11.8 (c = 0.568, DMSO) |
| 36 | 1H NMR spectrum (500 MHz; (δ in ppm); (DMSO-d6)): this is a 50-50 mixture of rotamers with: 0.91 (m, 3H); 1.71 (m, 1H); 1.81 (m, 1H); 2.65-2.80 (m, 2H); 3.11 (s, 1.5H); 3.13 (s, 1.5H); 3.34 (m, 2H); 4.25-4.38 (m, 2H); 4.72 (m, 1H); 7.02 (broad s, 1H); 7.30 (m, 8H); 7.43-7.49 (m, 2H); 7.96-8.10 (m, 1H); 8.49 (resolved d, J = 8.1 Hz, 1H); Mass spectrum: ES m/z = 607 [M + H]$^+$, m/z = 605 [M − H]$^−$; Optical rotation: $\alpha_D$ = +22.4 (c = 0.588, DMSO) |
| 37 | 1H NMR spectrum (500 MHz; (δ in ppm); (DMSO-d6)): 2.36 (s, 3H); 2.70 (t, J = 7.5 Hz, 2H); 2.96 (s, 3H); 3.31-3.35 (m, 2H); 3.80 (d, J = 6.0 Hz, 2H); 4.38 (s, 1H); 4.70 (m, 1H); 7.02 (broad s, 1H); 7.31 (m, 5H); 7.36 (m, 5H); 7.58 (broad s, 1H); 7.68 (broad s, 1H); 8.66 (t, J = 6.0 Hz, 1H); Mass spectrum: ES m/z = 575 [M + H]$^+$, m/z = 573 [M − H]$^−$ |
| 38 | 1H NMR spectrum (500 MHz; (δ in ppm); (DMSO-d6)): 1.33 (d, J = 7.4 Hz, 3H); 2.36 (s, 3H); 2.70 (m, 2H); 2.96 (s, 3H); 3.31-3.36 (m, 2H); 4.38 (s, 1H); 4.43 (m, 1H); 4.71 (m, 1H); 6.98 (broad s, 1H); 7.28-7.40 (m, 10H); 7.59 (broad s, 1H); 7.71 (broad s, 1H); 8.42 (d, J = 7.4 Hz, 1H); Mass spectrum: ES m/z = 589 [M + H]$^+$, m/z = 587 ; [M − H]$^−$; Optical rotation: $\alpha_D$ = +26.4 (c = 0.503, DMSO) |
| 39 | 1H NMR spectrum (500 MHz; (δ in ppm); (DMSO-d6)): 0.90 (t, J = 7.4 Hz, 3H); 1.68 (m, 1H); 1.81 (m, 1H); 2.36 (s, 3H); 2.71 (m, 2H); 2.96 (s, 3H); 3.31-3.34 (m, 2H); 4.32 (td, J = 8.3; 5.2 Hz, 1H); 4.38 (s, 1H); 4.71 (m, 1H); 7.00 (broad s, 1H); 7.31 (m, 5H); 7.35 (d, J = 8.5 Hz, 4H); 7.40 (broad s, 1H); 7.59 (broad s, 1H); 7.73 (broad s, 1H); 8.31 (d, J = 8.3 Hz, 1H); Mass spectrum: ES m/z = 603 [M + H]$^+$, m/z = 601 [M − H]$^−$; Optical rotation: $\alpha_D$ = +20.4 (c = 0.529, DMSO) |
| 40 | 1H NMR spectrum (500 MHz; (δ in ppm); (DMSO-d6)): 0.91 (d, J = 6.9 Hz, 3H); 0.93 (d, J = 6.9 Hz, 3H); 2.09 (m, 1H); 2.37 (s, 3H); 2.71 (m, 2H); 2.96 (s, 3H); 3.31-3.35 (m, 2H); 4.27 (t, J = 8.4 Hz, 1H); 4.38 (s, 1H); 4.71 (m, 1H); 7.06 (broad s, 1H); 7.27-7.33 (m, 5H); 7.35 (d, J = 8.6 Hz, 4H); 7.47 (broad s, 1H); 7.58 (broad s, 1H); 7.72 (broad s, 1H); 8.17 (d, J = 8.4 Hz, 1H); Mass spectrum: ES m/z = 617 [M + H]$^+$, m/z = 615 [M − H]$^−$; Optical rotation: $\alpha_D$ = +19.1 (c = 0.483, DMSO) |
| 41 | 1H NMR spectrum (500 MHz; (δ in ppm); (DMSO-d6)): 1.31 (d, J = 7.4 Hz, 3H); 2.36 (s, 3H); 2.59 (d, J = 4.6 Hz, 3H); 2.70 (m, 2H); 2.96 (s, 3H); 3.33 (m, 2H); 4.38 (s, 1H); 4.43 (m, 1H); 4.70 (m, 1H); 7.31 (m, 5H); 7.35 (d, J = 8.5 Hz, 4H); 7.59 (s, 1H); 7.73 (s, 1H); 7.83 (q, J = 4.6 Hz, 1H); 8.49 (d, J = 7.4 Hz, 1H); Mass spectrum: ES m/z = 603 [M + H]$^+$, m/z = 601 |
| | [M − H]$^−$; Optical rotation: $\alpha_D$ = +27.4 (c = 0.507, DMSO) |
| 42 | 1H NMR spectrum (500 MHz; (δ in ppm); (DMSO-d6)): 2.37 (s, 3H); 2.70 (t, J = 7.5 Hz, 2H); 2.96 (s, 3H); 3.33 (m, 2H); 3.67-3.75 (m, 2H); 4.38 (s, 1H); 4.43 (m, 1H); 4.71 (m, 1H); 4.90 (t, J = 5.9 Hz, 1H); 7.09 (broad s, 1H); 7.29-7.32 (m, 5H); 7.36 (d, J = 8.5 Hz, 4H); 7.39 (broad s, 1H); 7.60 (s, 1H); 7.72 (s, 1H); 8.21 (d, J = 8.0 Hz, 1H); Mass spectrum: ES m/z = 605 [M + H]$^+$, m/z = 603 [M − H]$^−$; Optical rotation: $\alpha_D$ = +23.1 (c = 0.521, DMSO) |
| 43 | 1H NMR spectrum (400 MHz; (δ in ppm); (DMSO-d6)): 1.33 (d, J = 7.4 Hz, 3H); 2.74 (t, J = 7.5 Hz, 2H); 3.01 (s, 3H); 3.31-3.37 (m partially masked, 2H); 4.36-4.44 (m, 2H); 4.73 (m, 1H); 6.98 (broad s, 1H); 7.32 (d, J = 8.5 Hz, 4H); 7.34 (d, J = 8.5 Hz, 4H); 7.40 (broad s, 1H); 7.61 (t, J = 2.0 Hz, 1H); 7.77 (t, J = 2.0 Hz, 1H); 7.98 (t, J = 2.0 Hz, 1H); 8.65 (d, J = 7.4 Hz, 1H); Mass spectrum: ES m/z = 611 [M + H]$^+$, m/z = 609 [M − H]$^−$; Optical rotation: $\alpha_D$ = +27.2 (c = 0.569, DMSO) |
| 44 | 1H NMR spectrum (400 MHz; (δ in ppm); (DMSO-d6)): 0.90 (t, J = 7.4 Hz, 3H); 1.69 (m, 1H); 1.81 (m, 1H); 2.75 (t, J = 7.3 Hz, 2H); 3.00 (s, 3H); 3.31-3.36 (m partially masked, 2H); 4.30 (m, 1H); 4.41 (s, 1H); 4.74 (m, 1H); 7.00 (broad s, 1H); 7.31 (d, J = 8.5 Hz, 4H); 7.34 (d, J = 8.5 Hz, 4H); 7.43 (broad s, 1H); 7.61 (t, J = 2.0 Hz, 1H); 7.77 (t, J = 2.0 Hz, 1H); 8.00 (t, J = 2.0 Hz, 1H); 8.55 (d, J = 8.2 Hz, 1H); Mass spectrum: ES m/z = 625 [M + H]$^+$, m/z = 623 [M − H]$^−$; Optical rotation: $\alpha_D$ = +22.5 (c = 0.498, DMSO) |
| 45 | 1H NMR spectrum (400 MHz; (δ in ppm); (DMSO-d6)): 0.90 (d, J = 6.6 Hz, 3H); 0.92 (d, J = 6.6 Hz, 3H); 2.11 (m, 1H); 2.74 (m, 2H); 3.00 (s, 3H); 3.33 (m, 2H); 4.28 (m, 1H); 4.41 (s, 1H); 4.75 (m, 1H); 7.05 (broad s, 1H); 7.31 (d, J = 8.5 Hz, 4H); 7.35 (d, J = 8.5 Hz, 4H); 7.48 (broad s, 1H); 7.61 (t, J = 1.9 Hz, 1H); 7.76 (t, J = 1.9 Hz, 1H); 7.99 (t, J = 1.9 Hz, 1H); 8.44 (d, J = 8.6 Hz, 1H); Mass spectrum: ES m/z = 639 [M + H]$^+$; m/z = 623 [M − H]$^−$; Optical rotation: $\alpha_D$ = +22.3 (c = 0.558, DMSO) |
| 46 | 1H NMR spectrum (400 MHz; (δ in ppm); (DMSO-d6)): 1.32 (d, J = 7.1 Hz, 3H); 2.59 (d, J = 4.7 Hz, 3H); 2.73 (t, J = 7.1 Hz, 2H); 3.01 (s, 3H); 3.33 (m, 2H); 4.37-4.46 (m, 2H); 4.73 (m, 1H); 7.32 (d, J = 8.6 Hz, 4H); 7.34 (d, J = 8.6 Hz, 4H); 7.62 (t, J = 1.9 Hz, 1H); 7.77 (t, J = 1.9 Hz, 1H); 7.85 (q, J = 4.7 Hz, 1H); 8.00 (t, J = 1.9 Hz, 1H); 8.71 (d, J = 7.5 Hz, 1H); Mass spectrum: ES m/z = 625 [M + H]$^+$; m/z = 623 [M − H]$^−$; Optical rotation: $\alpha_D$ = +28.1 (c = 0.557, DMSO) |
| 47 | 1H NMR spectrum (400 MHz; (δ in ppm); (DMSO-d6)): 2.73 (t, J = 7.4 Hz, 2H); 3.01 (s, 3H); 3.34 (t, J = 7.1 Hz, 2H); 3.65-3.76 (m, 2H); 4.39-4.46 (m, 2H); 4.74 (m, 1H); 4.89 (t, J = 5.9 Hz, 1H); 7.09 (broad s, 1H); 7.32 (d, J = 8.6 Hz, 4H); 7.35 (d, J = 8.6 Hz, 4H); 7.41 (broad s, 1H); 7.62 (t, J = 1.9 Hz, 1H); 7.77 (t, J = 1.9 Hz, 1H); 7.99 (t, J = 1.9 Hz, 1H); 8.47 (d, J = 8.0 Hz, 1H); Mass spectrum: ES m/z = 627 [M + H]$^+$, m/z = 625 [M − H]$^−$; Optical rotation: $\alpha_D$ = +24.4 (c = 0.534, DMSO) |
| 48 | 1H NMR spectrum (400 MHz; (δ in ppm); (DMSO-d6)): 1.33 (d, J = 7.2 Hz, 3H); 2.74 (t, J = 7.1 Hz, 2H); 3.00 (s, 3H); 3.33 (t, J = 7.1 Hz, 2H); 4.35-4.44 (m, 2H); 4.72 (m, 1H); 6.97 (broad s, 1H); 7.32 (d, J = 8.5 Hz, 4H); 7.34 (d, J = 8.5 Hz, 4H); 7.40 (broad s, 1H); 7.74 (t, J = 1.8 Hz, 1H); 7.80 (t, J = 1.8 Hz, 1H); 8.12 (t, J = 1.8 Hz, 1H); 8.65 (d, J = 7.5 Hz, 1H); Mass spectrum: ES m/z = 655 [M + H]$^+$; m/z = 653 [M − H]$^−$; Optical rotation: $\alpha_D$ = +27.7 (c = 0.5826, DMSO) |
| 49 | 1H NMR spectrum (400 MHz; (δ in ppm); (DMSO-d6)): 0.90 (t, J = 7.6 Hz, 3H); 1.68 (m, 1H); 1.82 (m, 1H); 2.74 (t, J = 7.3 Hz, 2H); 3.00 (s, 3H); 3.33 (t, J = 7.3 Hz, 2H); 4.30 (m, 1H); 4.41 (s, 1H); 4.74 (m, 1H); 7.00 (broad s, 1H); 7.31 (d, J = 8.6 Hz, 4H); 7.34 (d, J = 8.6 Hz, 4H); 7.43 (broad s, 1H); 7.74 (t, J = 1.2 Hz, 1H); 7.81 (t, J = 1.2 Hz, 1H) 8.14 (t, J = 1.2 Hz, 1H); 8.55 (d, J = 8.2 Hz, 1H); Mass spectrum: ES m/z = 667 [M + H]$^+$; m/z = 665 [M − H]$^−$; Optical rotation: $\alpha_D$ = +21.3 (c = 0.559, DMSO) |
| 50 | 1H NMR spectrum (400 MHz; (δ in ppm); (DMSO-d6)): 0.92 (t, J = 6.8 Hz, 3H); 2.10 (m, 1H); 2.75 (t, J = 7.1 Hz, 2H); 3.00 (s, 3H); 3.32 (m partially masked, 2H); 4.27 (t, J = 8.2 Hz, 1H); 4.41 (s, 1H); 4.74 (m, 1H); 7.05 (broad s, 1H); 7.30 (d, J = 8.6 Hz, 4H); 7.34 (d, J = 8.6 Hz, 4H); 7.48 (broad s, 1H); 7.74 (t, J = 1.2 Hz, 1H); 7.80 (t, J = 1.2 Hz, 1H); 8.13 (t, J = 1.2 Hz, 1H); 8.45 (d, J = 8.2 Hz, 1H); Mass spectrum: ES m/z = 681 [M + H]$^+$; m/z = 679 [M − H]$^−$; Optical rotation: $\alpha_D$ = +22.3 (c = 0.522, DMSO) |
| 51 | 1H NMR spectrum (400 MHz; (δ in ppm); (DMSO-d6)): 1.32 (d, J = 7.3 Hz, 3H); 2.59 (d, J = 4.9 Hz, 3H); 2.74 (t, J = 7.1 Hz, |

TABLE 1A-continued

| No. | Characterizations |
|---|---|
| | 2H); 3.00 (s, 3H); 3.33 (m partially masked, 2H); 4.37-4.46 (m, 2H); 4.73 (m, 1H); 7.31 (d, J = 8.7 Hz, 4H); 7.34 (d, J = 8.7 Hz, 4H); 7.75 (t, J = 1.0 Hz, 1H); 7.80 (t, J = 1.0 Hz, 1H); 7.85 (q, J = 4.9 Hz, 1H); 8.14 (t, J = 1.0 Hz, 1H); 8.72 (d, J = 7.7 Hz, 1H); Mass spectrum: ES m/z = 667 [M + H]$^+$, m/z = 665 [M − H]$^-$; Optical rotation: $\alpha_D$ = +27.6 (c = 0.504, DMSO) |
| 52 | 1H NMR spectrum (400 MHz; (δ in ppm); (DMSO-d6)): 2.74 (t, J = 7.2 Hz, 2H); 3.01 (s, 3H); 3.33 (t, J = 7.2 Hz, 2H); 3.71 (m, 2H); 4.41-4.47 (m, 2H); 4.74 (m, 1H); 4.89 (t, J = 6.1 Hz, 1H); 7.09 (broad s, 1H); 7.31 (d, J = 8.6 Hz, 4H); 7.35 (d, J = 8.6 Hz, 4H); 7.41 (broad s, 1H); 7.74 (t, J = 1.3 Hz, 1H); 7.80 (t, J = 1.3 Hz, 1H); 8.13 (t, J = 1.3 Hz, 1H); 8.48 (d, J = 8.2 Hz, 1H); Mass spectrum: ES m/z = 669[M + H]$^+$, m/z = 667 [M − H]$^-$; Optical rotation: $\alpha_D$ = +23.3 (c = 0.553, DMSO) |
| 53 | 1H NMR spectrum (400 MHz; (δ in ppm); (DMSO-d6)): 2.76 (t, J = 7.3 Hz, 2H);3.03 (s, 3H); 3.35 (m, 2H); 3.84 (d, J = 5.9 Hz, 2H); 4.41 (s, 1H); 4.80 (m, 1H); 7.06(broad s, 1H); 7.30 (d, J = 8.6 Hz, 4H); 7.33 (d, J = 8.6 Hz, 4H); 7.43 (broad s, 1H); 7.86 (broad s, 1H); 8.08 (broad s, 1H); 8.22 (broad s, 1H); 9.04 (t, J = 5.9 Hz, 1H); Mass spectrum: ES m/z = 629 [M + H]$^+$, m/z = 627 [M − H]$^-$ |
| 54 | 1H NMR spectrum (400 MHz; (δ in ppm); (DMSO-d6)): 1.35 (d, J = 7.3 Hz, 3H); 2.76 (t, J = 7.2 Hz, 2H); 3.02 (s, 3H); 3.34 (t, J = 7.2 Hz, 2H); 4.33-4.50 (m, 2H); 4.81 (m, 1H); 6.99 (broad s, 1H); 7.30 (d, J = 8.7 Hz, 4H); 7.33 (d, J = 8.7 Hz, 4H); 7.43 (broad s, 1H); 7.86 (broad s, 1H); 8.09 (broad s, 1H); 8.28 (broad s, 1H); 8.83 (d, J = 7.7 Hz, 1H); Mass spectrum: ES m/z = 643 [M + H]$^+$, m/z = 641 [M − H]$^-$; Optical rotation: $\alpha_D$ = +22.5 (c = 0.516, DMSO) |
| 55 | 1H NMR spectrum (400 MHz; (δ in ppm); (DMSO-d6)): 0.91 (t, J = 7.3 Hz, 3H); 1.71 (m, 1H); 1.84 (m, 1H); 2.77 (t, J = 7.1 Hz, 2H); 3.02 (s, 3H); 3.34 (t, J = 7.1 Hz, 2H); 4.34 (m, 1H); 4.41 (s, 1H); 4.81 (m, 1H); 7.02 (broad s, 1H); 7.28-7.34 (m, 8H); 7.46 (broad s, 1H); 7.86 (broad s, 1H); 8.10 (broad s, 1H); 8.30 (broad s, 1H); 8.74 (d, J = 8.3 Hz, 1H); Mass spectrum: ES m/z = 657 [M + H]$^+$, m/z = 655 [M − H]$^-$; Optical rotation: $\alpha_D$ = +18.3 (c = 0.529, DMSO) |
| 56 | 1H NMR spectrum (400 MHz; (δ in ppm); (DMSO-d6)): 0.92 (t, J = 6.8 Hz, 3H); 0.95 (t, J = 6.8 Hz, 3H); 2.12 (m, 1H); 2.77 (t, J = Hz, 2H); 3.02 (s, 3H); 3.33 (t, J = 7.1 Hz, 2H); 4.34 (m, 1H); 4.41 (s, 1H); 4.81 (m, 1H); 7.07 (broad s, 1H); 7.25-7.36 (m, 8H); 7.52 (broad s, 1H); 7.86 (broad s, 1H); 8.10 (broad s, 1H); 8.28 (broad s, 1H); 8.66 (d, J = 8.5 Hz, 1H); Mass spectrum: ES m/z = 671 [M + H]$^+$, m/z = 669 [M − H]$^-$; Optical rotation: $\alpha_D$ = +17.6 (c = 0.548, DMSO) |
| 57 | 1H NMR spectrum (400 MHz; (δ in ppm); (DMSO-d6)): 1.34 (d, J = 7.3 Hz, 3H); 2.60 (d, J = 4.6 Hz, 3H); 2.77 (t, J = 7.2 Hz, 2H); 3.03 (s, 3H); 3.34 (t, J = 7.2 Hz, 2H); 4.41 (s, 1H); 4.46 (m, 1H); 4.81 (m, 1H); 7.26-7.37 (m, 8H); 7.83-7.92 (m, 2H); 8.10 (broad s, 1H); 8.29 (broad s, 1H); 8.89 (d, J = 7.6 Hz, 1H); Mass spectrum: ES m/z = 657 [M + H]$^+$; m/z = 655 [M − H]$^-$; Optical rotation: $\alpha_D$ = +22.1 (c = 0.523, DMSO) |
| 58 | 1H NMR spectrum (400 MHz; (δ in ppm); (DMSO-d6)): 2.77 (t, J = 7.3 Hz, 2H); 3.03 (s, 3H); 3.34 (t, J = 7.3 Hz, 2H); 3.63-3.86 (m, 2H); 4.42 (s, 1H); 4.47 (m, 1H); 4.82 (m, 1H); 4.91 (t, J = 6.0 Hz, 1H); 7.11 (broad s, 1H); 7.30 (d, J = 8.6 Hz, 4H); 7.34 (d, J = 8.6 Hz, 4H); 7.44 (broad s, 1H); 7.87 (broad s, 1H); 8.10 (broad s, 1H); 8.29 (broad s, 1H); 8.68 (d, J = 8.0 Hz, 1H); Mass spectrum: ES m/z = 659 [M + H]$^+$; m/z = 657 [M − H]$^-$; Optical rotation: $\alpha_D$ = +19.5 (c = 0.546, DMSO) |
| 59 | 1H NMR spectrum (400 MHz; (δ in ppm); (DMSO-d6)): 1.34 (d, J = 7.3 Hz, 3H); 2.74 (t, J = 7.3 Hz, 2H); 3.03 (s, 3H); 3.36 (t, J = 7.3 Hz, 2H); 4.36-4.46 (m, 2H); 4.75 (m, 1H); 7.00 (broad s, 1H); 7.31 (d, J = 8.8 Hz, 4H); 7.34 (d, J = 8.8 Hz, 4H); 7.42 (broad s, 1H); 8.02 (broad s, 1H); 8.09 (broad s, 1H); 8.36 (broad s, 1H); 8.75 (d, J = 7.5 Hz, 1H); Mass spectrum: ES m/z = 600 [M + H]$^+$; m/z = 598 [M − H]$^-$; Optical rotation: $\alpha_D$ = +28.9 (c = 0.568, DMSO) |
| 60 | 1H NMR spectrum (400 MHz; (δ in ppm); (DMSO-d6)): 0.91 (t, J = 7.6 Hz, 3H); 1.69 (m, 1H); 1.80 (m, 1H); 2.75 (t, J = 7.3 Hz, 2H); 3.03 (s, 3H); 3.35 (t, J = 7.3 Hz, 2H); 4.32 (m, 1H); 4.40 (s, 1H); 4.75 (m, 1H); 7.02 (broad s, 1H); 7.26-7.37 (m, 8H); 7.45 (broad s, 1H); 8.03 (broad s, 1H); 8.10 (broad s, 1H); 8.39 (broad s, 1H); 8.64 (d, J = 7.9 Hz, 1H); Mass spectrum: ES m/z = 614 [M + H]$^+$; m/z = 612 [M − H]$^-$; Optical rotation: $\alpha_D$ = +24.4 (c = 0.516, DMSO) |
| 61 | 1H NMR spectrum (400 MHz; (δ in ppm); (DMSO-d6)): 0.92 (d, J = 6.8 Hz, 3H); 0.94 (d, J = 6.8 Hz, 3H); 2.11 (m, 1H); 2.75 (t, J = 7.1 Hz, 2H); 3.03 (s, 3H); 3.35 (t, J = 7.1 Hz, 2H); 4.30 (m, 1H); 4.40 (s, 1H); 4.75 (m, 1H); 7.07 (broad s, 1H); 7.28-7.35 (m, 8H); 7.50 (broad s, 1H); 8.02 (broad s, 1H); 8.08 (broad s, 1H); 8.40 (broad s, 1H); 8.52 (d, J = 8.8 Hz, 1H); Mass spectrum: ES m/z = 628 [M + H]$^+$; m/z = 626 [M − H]$^-$; Optical rotation: $\alpha_D$ = +25.2 (c = 0.562, DMSO) |
| 62 | 1H NMR spectrum (400 MHz; (δ in ppm); (DMSO-d6)): 1.33 (d, J = 7.3 Hz, 3H); 2.59 (d, J = 4.6 Hz, 3H); 2.75 (t, J = 7.1 Hz, 2H); 3.03 (s, 3H); 3.35 (t, J = 7.1 Hz, 2H); 4.40 (s, 1H); 4.43 (m, 1H); 4.74 (m, 1H); 7.24-7.39 (m, 8H); 7.88 (q, J = 4.6 Hz, 1H); 8.03 (broad s, 1H); 8.10 (broad s, 1H); 8.37 (broad s, 1H); 8.81 (d, J = 7.6 Hz, 1H); Mass spectrum: ES m/z = 614 [M + H]$^+$, m/z = 612 [M − H]$^-$; Optical rotation: $\alpha_D$ = +28.1 (c = 0.578, DMSO) |
| 63 | 1H NMR spectrum (400 MHz; (δ in ppm); (DMSO-d6)): 2.75 (t, J = 7.3 Hz, 2H); 3.03 (s, 3H); 3.36 (m, 2H); 3.73 (m, 2H); 4.41 (s, 1H); 4.44 (m, 1H); 4.75 (m, 1H);4.91 (t, J = 5.9 Hz, 1H); 7.11 (broad s, 1H); 7.31 (d, J = 8.8 Hz, 4H); 7.35 (d, J = 8.8 Hz, 4H); 7.43 (broad s, 1H); 8.03 (broad s, 1H); 8.09 (broad s, 1H); 8.38 (broad s, 1H); 8.60 (d, J = 8.1 Hz, 1H); Mass spectrum: ES m/z = 616 [M + H]$^+$; m/z =614 [M − H]$^-$; Optical rotation: $\alpha_D$ = +24.4 (c = 0.528, DMSO) |
| 64 | 1H NMR spectrum (400 MHz; (δ in ppm); (DMSO-d6)): 1.37 (d, J = Hz, 3H); 3.00 (broad s, 3H); 2.50-3.60 (very broad m, 4H); 4.39 (m, 2H); 4.80 (broad m, 1H); 7.32-7.46 (m, 9H); 7.48-7.60 (m, 2H); 8.63 (broad d, J = 7.0 Hz, 1H); 12.70 (broad m, 1H); Mass spectrum: ES m/z = 594 [M + H]$^+$, m/z = 592 [M − H]$^-$; Optical rotation: $\alpha_D$ = +20.7 (c = 0.326, DMSO) |
| 65 | 1H NMR spectrum (500 MHz; (δ in ppm); (DMSO-d6)): 1.40 (d, J = 7.3 Hz, 3H); 2.38 (s, 3H); 3.00 (broad s, 3H); 2.70-4.30 (very broad m, 5H); 4.41 (m, 1H); 4.83 (broad m, 1H); 7.33 (broad s, 1H); 7.33-7.47 (m, 8H); 7.61 (broad s, 1H); 7.74 (broad s, 1H); 8.71 (d, J = 7.5 Hz, 1H); 12.61 (broad m, 1H); Mass spectrum: ES m/z = 590 [M + H]$^+$, m/z = 588 [M − H]$^-$; Optical rotation: $\alpha_D$ = +13 (c = 0.313, DMSO) |
| 66 | 1H NMR spectrum (500 MHz; (δ in ppm); (DMSO-d6)): 1.40 (d, J = 7.3 Hz, 3H); 2.70-4.30 (very broad m, 5H); 3.04 (broad s, 3H); 4.42 (m, 1H); 4.85 (broad m, 1H); 7.38 (m, 8H); 7.66 (broad s, 1H); 7.79 (broad s, 1H); 7.99 (broad s, 1H); 8.89 (d, J = 7.4 Hz, 1H); 12.67 (broad m, 1H); Mass spectrum: ES m/z = 610 [M + H]$^+$, m/z = 608 [M − H]$^-$; Optical rotation: $\alpha_D$ = +15.8 (c = 0.310, DMSO) |
| 67 | 1H NMR spectrum (500 MHz; (δ in ppm); (DMSO-d6)): 1.40 (d, J = 7.3 Hz, 3H); 2.70-4.30 (very broad m, 5H); 3.03 (broad s, 3H); 4.41 (m, 1H); 4.84 (broad m, 1H); 7.23 (m, 8H); 7.78 (broad s, 1H); 7.82 (broad s, 1H); 8.12 (broad s, 1H); 8.90 (d, J = 7.3 Hz, 1H); 12.65 (broad m, 1H); Mass spectrum: ES m/z = 654 [M + H]$^+$; m/z = 652 [M − H]$^-$; Optical rotation: $\alpha_D$ = +20.9 (c = 0.5236, DMSO) |
| 68 | 1H NMR spectrum (500 MHz; (δ in ppm); (DMSO-d6)): 1.42 (d, J = 7.3 Hz, 3H); 2.70-4.30 (very broad m, 5H); 3.05 (broad s, 3H); 4.45 (m, 1H); 4.93 (broad m, 1H); 7.37 (m, 8H); 7.91 (broad s, 1H); 8.12 (broad s, 1H); 8.29 (broad s, 1H); 9.06 (d, J = 7.3 Hz, 1H); 12.70 (broad m, 1H); Mass spectrum: ES m/z = 644 [M + H]$^+$, m/z = 642 [M − H]$^-$; Optical rotation: $\alpha_D$ = +14.3 (c = 0.349, DMSO) |
| 69 | 1H NMR spectrum (500 MHz; (δ in ppm); (DMSO-d6)): 1.41 (d, J = 7.3 Hz, 3H); 2.70-4.30 (very broad m, 5H); 3.05 (broad s, 3H); 4.43 (m, 1H); 4.83 (broad m, 1H); 7.37 (m, 8H); 8.05 (broad s, 1H); 8.12 (broad s, 1H); 8.36 (broad s, 1H); 8.97 (d, J = 7.2 Hz, 1H); 12.72 (broad m, 1H); Mass spectrum: ES m/z = 601 [M + H]$^+$, m/z = 599 [M − H]$^-$; Optical rotation: $\alpha_D$ = +8 (c = 0.226, DMSO) |
| 70 | 1H NMR spectrum (400 MHz; (δ in ppm); (DMSO-d6)): 1.33 (d, J = 7.1 Hz, 3H); 2.73 (m, 2H); 3.00 (s, 3H); 3.35 (m, 2H); 4.38 (s, 1H); 4.41 (m, 1H); 4.72 (m, 1H); 6.98 (broad s, 1H); 7.30 (d, J = 8.6 Hz, 4H); 7.39 (broad s, 1H); 7.42 (m partially masked, 1H); 7.45 (d, J = 8.6 Hz, 4H); 7.67 (t, J = 1.8 Hz, 1H); 7.74 (dt, J = 9.2; 1.8 Hz, 1H); 8.60 (d, J = 7.5 Hz, 1H); Mass spectrum: ES m/z = 681 [M + H]$^+$, m/z = 679 [M − H]$^-$; Optical rotation: $\alpha_D$ = +21.4 (c = 0.352, DMSO) |
| 71 | 1H NMR spectrum (400 MHz; (δ in ppm); (DMSO-d6)): 1.33 (d, J = 7.1 Hz, 3H); 2.81 (t, J = 7.6 Hz, 2H); 3.01 (s, 3H); 3.41 (t, J = 7.6 Hz, 2H); 4.41 (m, 1H); 4.66 (s, 1H); 4.77 (m, 1H); 6.98 (broad s, 1H); 7.39 (broad s, 1H); 7.43 (dt, J = 9.5; 2.0 Hz, 1H); 7.61 (d, J = 8.7 Hz, 4H); 7.64 (d, J = 8.7 Hz, 4H); 7.69 (t, J = 2.0 Hz, 1H); 7.75 (dt, J = 9.5; 2.0 Hz, 1H); 8.61 (d, J = 7.6 Hz, 1H); Mass spectrum: ES m/z = 661 [M + H]$^+$, m/z = 659 |

TABLE 1A-continued

| No. | Characterizations |
|---|---|
|  | [M − H]⁻; Optical rotation: $\alpha_D$ = +21.8 (c = 0.361, DMSO) |
| 72 | 1H NMR spectrum (400 MHz; (δ in ppm); (DMSO-d6)): 1.34 (d, J = 7.3 Hz, 3H); 2.79 (t, J = 7.5 Hz, 2H); 3.01 (s, 3H); 3.39 (m, 2H); 4.41 (m, 1H); 4.65 (s, 1H); 4.76 (m, 1H); 6.98 (broad s, 1H); 7.40 (broad s, 1H); 7.42 (dt, J = 9.6; 1.9 Hz, 1H); 7.58 (d, J = 8.6 Hz, 4H); 7.68 (t, J = 1.9 Hz, 1H); 7.74 (m, 5H); 8.60 (d, J = 7.6 Hz, 1H); Mass spectrum: ES m/z = 575 [M + H]⁺, m/z = 573 [M − H]⁻; Optical rotation: $\alpha_D$ = +16 (c = 0.289, DMSO) |
| 73 | 1H NMR spectrum (400 MHz; (δ in ppm); (DMSO-d6)): 1.33 (d, J = 7.3 Hz, 3H); 2.67 (t, J = 7.2 Hz, 2H); 2.99 (s, 3H); 3.31 (m partially masked, 2H); 3.67 (s, 6H); 4.19 (s, 1H); 4.40 (m, 1H); 4.69 (m, 1H); 6.79 (d, J = 8.8 Hz, 4H); 6.98 (broad s, 1H); 7.22 (d, J = 8.8 Hz, 4H); 7.39 (broad s, 1H); 7.42 (dt, J = 9.5; 1.8 Hz, 1H); 7.67 (t, J = 1.8 Hz, 1H); 7.73 (broad d, J = 9.5 Hz, 1H); 8.60 (d, J = 7.7 Hz, 1H); Mass spectrum: ES m/z = 585 [M + H]⁺, m/z = 583 [M − H]⁻; Optical rotation: $\alpha_D$ = +18.9 (c = 0.398, DMSO) |
| 74 | 1H NMR spectrum (400 MHz; (δ in ppm); (DMSO-d6)): 1.33 (d, J = 7.3 Hz, 3H); 2.72 (t, J = 7.1 Hz, 2H); 2.99 (s, 3H); 3.33 (m partially masked, 2H); 4.39 (s, 1H); 4.40 (m, 1H); 4.71 (m, 1H); 6.98 (broad s, 1H); 7.07 (t, J = 8.8 Hz, 4H); 7.33-7.45 (m, 6H); 7.67 (broad s, 1H); 7.74 (broad d, J = 9.5 Hz, 1H); 8.60 (d, J = 7.7 Hz, 1H); Mass spectrum: ES m/z = 561 [M + H]⁺, m/z = 559 [M − H]⁻; Optical rotation: $\alpha_D$ = +18.1 (c = 0.309, DMSO) |
| 75 | 1H NMR spectrum (400 MHz; (δ in ppm); (DMSO-d6)): 1.41 (d, J = 7.3 Hz, 3H); 2.74 (m, 2H); 3.00 (s, 3H); 3.36 (m, 2H); 3.64 (s, 3H); 4.40 (s, 1H); 4.48 (m, 1H); 4.72 (m, 1H); 7.31 (d, J = 8.6 Hz, 4H); 7.36 (d, J = 8.6 Hz, 4H); 7.46 (dm, J = 9.5 Hz, 1H); 7.68 (broad s, 1H); 7.71 (broad d, J = 9.5 Hz, 1H); 8.93 (d, J = 6.8 Hz, 1H); Mass spectrum: ES m/z = 608 [M + H]⁺, m/z = 606 [M − H]⁻; Optical rotation: $\alpha_D$ = +6.7 (c = 0.347, DMSO) |
| 76 | 1H NMR spectrum (400 MHz; (δ in ppm); (DMSO-d6)): 0.90 (t, J = 7.3 Hz, 3H); 1.70 (m, 1H); 1.81 (m, 1H); 2.20 (s, 6H); 2.69 (m, 2H); 2.99 (s, 3H); 3.33 (m partially masked, 2H); 4.22 (s, 1H); 4.30 (m, 1H); 4.70 (m, 1H); 7.01 (broad s, 1H); 7.03 (d, J = 8.1 Hz, 4H); 7.20 (d, J = 8.1 Hz, 4H); 7.39-7.44 (m, 2H); 7.67 (broad s, 1H); 7.75 (dm, J = 9.5 Hz, 1H); 8.5 (d, J = 7.8 Hz, 1H); Mass spectrum: ES m/z = 567 [M + H]⁺, m/z = 565 [M − H]⁻; Optical rotation: $\alpha_D$ = +17.7 (c = 0.474, DMSO) |
| 77 | 1H NMR spectrum (400 MHz; (δ in ppm); (DMSO-d6)): 1.32 (d, J = 7.3 Hz, 3H); 2.59 (d, J = 4.7 Hz, 3H); 2.74 (m, 2H); 3.00 (s, 3H); 3.35 (m, 2H); 4.37 (s, 1H); 4.42 (m, 1H); 4.72 (m, 1H); 7.29 (d, J = 8.7 Hz, 4H); 7.42 (m partially masked, 1H); 7.45 (d, J = 8.7 Hz, 4H); 7.68 (t, J = 1.9 Hz, 1H); 7.76 (ddd, J = 9.4; 1.9 Hz, 1H); 7.85 (q, J = 4.7 Hz, 1H); 8.67 (d, J = 7.6 Hz, 1H); Mass spectrum: ES m/z = 695 [M + H]⁺, m/z = 693 [M − H]⁻; Optical rotation: $\alpha_D$ = +20.6 (c = 0.399, DMSO) |
| 78 | 1H NMR spectrum (400 MHz; (δ in ppm); (DMSO-d6)): 1.34 (d, J = 7.3 Hz, 3H); 2.74 (m, 2H); 2.99 (s, 3H); 3.34 (m, 2H); 4.19 (m, 1H); 4.39 (s, 1H); 4.73 (m, 1H); 7.30 (d, J = 8.7 Hz, 4H); 7.42 (m partially masked, 1H); 7.45 (d, J = 8.7 Hz, 4H); 7.60-7.68 (m, 2H); 8.53 (broad d, J = 6.6 Hz, 1H); 12.70 (very broad m, 1H); Mass spectrum: ES m/z = 682 [M + H]⁺, m/z = 680 [M − H]⁻; Optical rotation: $\alpha_D$ = −9.1 (c = 0.351, DMSO) |
| 79 | 1H NMR spectrum (400 MHz; (δ in ppm); (DMSO-d6)): 1.18 (t, J = 7.1 Hz, 3H); 1.41 (d, J = 7.3 Hz, 3H); 2.74 (m, 2H); 3.01 (s, 3H); 3.36 (m, 2H); 4.11 (m, 2H); 4.40 (s, 1H); 4.45 (m, 1H); 4.73 (m, 1H); 7.31 (d, J = 8.6 Hz, 4H); 7.36 (d, J = 8.6 Hz, 4H); 7.46 (dt, J = 9.5; 2.0 Hz, 1H); 7.68 (t, J = 2.0 Hz, 1H); 7.71 (dt, J = 9.7; 2.0 Hz, 1H); 8.91 (d, J = 7.0 Hz, 1H); Mass spectrum: ES m/z = 622 [M + H]⁺; m/z = 620 [M − H]⁻; Elemental analysis: Calculated: C: 55.95%- H: 4.86%- N: 6.75%- S: 5.15% Measured: C: 55.61%- H: 5.01%- N: 6.70%- S: 4.85% Optical rotation: $\alpha_D$ = +5 (c = 0.518, DMSO) |
| 80 | 1H NMR spectrum (400 MHz; (δ in ppm); (DMSO-d6)): 0.90 (t, J = 7.3 Hz, 3H); 1.69 (m, 1H); 1.80 (m, 1H); 2.77 (t, J = 7.3 Hz, 2H); 3.00 (s, 3H); 3.37 (t, J = 7.3 Hz, 2H); 4.30 (m, 1H); 4.51 (s, 1H); 4.74 (m, 1H); 7.00 (broad s, 1H); 7.26 (d, J = 8.8 Hz, 4H); 7.43 (m, 2H); 7.49 (d, J = 8.8 Hz, 4H); 7.69 (t, J = 1.7 Hz, 1H); 7.76 (dt, J = 9.4; 1.7 Hz, 1H); 8.50 (d, J = 8.1 Hz, 1H); Mass spectrum: ES m/z = 707 [M + H]⁺; m/z = 705 [M − H]⁻; Optical rotation: $\alpha_D$ = +18.2 (c = 0.5976, DMSO); Elemental analysis: Calculated: C: 50.99%- H: 4.14%- N: 7.93%- S: 4.54% Measured: C: 50.75%- H: 4.48%- N: 7.92%- S: 4.39% |

The compounds according to the invention were the subject of pharmacological tests for determining the activity with respect to human cannabinoid CB1-type receptors. The efficacy of the compounds of formula (I) was determined in a functional test which measures cannabinoid CB1 receptor activity (intracellular cyclic AMP test). The test for detecting intracellular cyclic AMP in U373MG cells naturally expressing the human CB1 receptor was carried out as described in the reference: Bouaboula et al., 1995, J. Biol. Chem. 270: 13973-13980. The HTRF cAMP Dynamic Kit from CisBio was used to quantify the intracellular cyclic AMP. In this test, the $IC_{50}$ values are between 0.001 μM and 2 μM.

For example, compounds No. 1, 3, 4, 6, 12, 36, 56, 68, 70 and 79 showed $IC_{50}$ values of, respectively, 0.043; 0.009; 0.284; 0.020; 0.009; 0.952; 0.041; 0.024; 0.031 and 0.070 μM.

Other tests consisting in measuring the in vivo activity of the compounds of the invention were carried out. The antagonist activity of said compounds was shown by means of the model of hypothermia induced by a cannabinoid CB receptor agonist (racemic CP55,940 (1RS, 3RS, 4RS)-3-[hydroxy-2-(1,1-dimethylheptyl)phenyl]-4-(3-hydroxypropyl)cyclohexan-1-ol) at a dose of 1.25 mg/kg, in mice, according to the method described by R. G. Pertwee in Marijuana 84, Harvey D. J. eds, Oxford IRL Press, 263-277 (1985). At time 0 min, the rectal temperature of male CD1 mice is measured before injection of the test product. At 30 minutes, a further measurement of the rectal temperature of the mice is taken and the racemic CP55,940 agonist ORS, 3RS, 4RS-3-[hydroxy-2-(1,1-dimethylheptyl)phenyl]-4-(3-hydroxypropyl)cyclohexan-1-ol) (1.25 mg/kg i.p. in 10% cremophor) is administered. At 90 minutes, the rectal temperature is again taken. The results are expressed as % relative to the control batch injected with the CP55,940 (minimum temperature) and to the carrier batch without CP55,940 treatment (maximum temperature). For example, compounds No. 1, 38, 55 and 57 showed percentages of inhibition of the decrease in temperature induced by the agonist of 5%, 17%, 28% and 21%, respectively, at 3 mg/kg po.

The antagonistic activity of the compounds was also shown by means of the model of inhibition of gastrointestinal transit induced by racemic CP55,940 (1RS, 3RS, 4RS-3-[hydroxy-2-(1,1-dimethylheptyl)phenyl]-4-(3-hydroxypropyl)cyclohexan-1-ol) in mice, according to the method described by Rinaldi-Carmona et al., J. Pharmacol. Exp. Ther. 2004, 310, 905-914. Briefly, male CD1 mice received the test product per os 30 minutes or 2 hours before administration of the racemic CP55,940 agonist (1RS, 3RS, 4RS-3-[hydroxy-2-(1,1-dimethylheptyl)phenyl]-4-(3-hydroxypropyl)cyclohexan-1-ol) (0.15 mg/kg ip in 10% cremophor). After a further 30 minutes, the animals received a charcoal bolus po. Thirty minutes later, the animals are sacrificed by euthanasia ($CO_2/O_2$) and the intestine is dissected. The progression of the charcoal bolus in the intestine is expressed as percentage of the total length of the intestine.

For example, compounds No. 1, 3, 16, 55, 57 and 68 showed percentages of inhibition at 1 mg/kg of 39.2%, 49%, 18%, 74%, 78% and 7%, respectively, at 3 hours after administration of the product.

Consequently, the compounds of the invention of formula (I) are cannabinoid CB1-type receptor antagonists in vitro and in vivo. Some compounds are active in vivo on both the hypothermia test and the transit test, and some compounds show dissociated activities between the hypothermia test and the transit test.

Thus, the compounds according to the invention can be used in the treatment or prevention of diseases involving cannabinoid CB1 receptors.

For example and in a nonlimiting manner, the compounds of formula (I) are of use as psychotropic medicaments, in particular for the treatment of psychiatric disorders including anxiety, depression, mood disorders, insomnia, delirium disorders, obsessive disorders, psychoses in general, schizophrenia, attention deficit hyperactivity disorders (ADHD) in hyperkinetic children (MBD), and also for the treatment of disorders associated with the use of psychotropic substances, in particular in the case of a substance abuse and/or a substance dependence, including alcohol dependence and nicotine dependence and withdrawal disorders. The compounds of formula (I) according to the invention can be used as medicaments for the treatment of migraine, stress, diseases of psychosomatic origin, panic attacks, epilepsy, motor disorders, in particular dyskinesia or Parkinson's disease, shaking and dystonia.

The compounds of formula (I) according to the invention can also be used as medicaments for skin cancer and skin protection.

The compounds of formula (I) according to the invention can also be used as medicaments in the treatment of memory disorders, cognitive disorders, in particular in the treatment of cognitive disorders associated with senile dementia, with Alzheimer's disease, with schizophrenia and with neurodegenerative diseases, and also in the treatment of attention or consciousness disorders.

Furthermore, the compounds of formula (I) may be of use as neuroprotectors, in the treatment of ischemia and cranial traumas and the treatment of neurodegenerative diseases: including Huntington's chorea and Tourrette's syndrome.

The compounds of formula (I) according to the invention can be used as medicaments in the treatment of pain: neuropathic pain, acute peripheral pain, chronic pain and pain of inflammatory origin.

The compounds of formula (I) according to the invention can be used as medicaments in the treatment of appetite disorders, appetence disorders (craving for sugars, carbohydrates, drugs, alcohols or any appetizing substance) and/or eating disorders, in particular for the treatment of boulemia and also for the treatment of type II diabetes or non-insulin-dependent diabetes and for the treatment of dyslipidemia and metabolic syndrome. Thus, the compounds of formula (I) according to the invention are of use in the treatment of obesity and the risks associated with obesity, in particular cardiovascular risks.

Furthermore, the compounds of formula (I) according to the invention can be used as medicaments in the treatment of gastrointestinal disorders, diarrhoea disorders, ulcers, vomiting, bladder and urinary disorders, disorders of endocrine origin, cardiovascular disorders, hypotension, haemorrhagic shock, septic shock, cirrhosis, hepatic fibrosis, steatohepatitis and hepatic steatosis, irrespective of the etiology of these conditions: in particular, virus, alcohol, medicament, chemical product, autoimmune disease, obesity, diabetes, congenital metabolic disease (haemochromatosis, alpha-1 antitrypsin deficiency, Wilson's disease, etc.), chronic liver cirrhosis, fibrosis, non-alcoholic steatohepatitis (NASH), asthma, chronic obstructive pulmonary diseases, Raynaud's syndrome, glaucoma, fertility disorders, inflammatory phenomena, inflammatory diseases, immune system diseases, in particular autoimmune or neuroinflammatory diseases such as rheumatoid arthritis, reactive arthritis, diseases which result in demyelination, multiple sclerosis, infectious and viral diseases such as encephalitis, cerebral strokes, and also as medicaments for anticancer chemotherapy, for the treatment of Guillain-Barré syndrome and for the treatment of osteoporosis and sleep apnoea.

According to one of its aspects, the present invention relates to the use of a compound of formula (I), of the pharmaceutically acceptable salts thereof, and of the solvates or hydrates thereof, for the treatment of the disorders and diseases indicated above.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or the salt thereof, can be administered in unit administration form, as a mixture with conventional pharmaceutical excipients for the treatment of the disorders or diseases mentioned above.

Suitable unit administration forms comprise oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

There may be specific cases where higher or lower dosages are appropriate; such dosages do not depart from the context of the invention. According to customary practice, the dosage suitable for each patient is determined by the physician according to the method of administration and the weight and response of said patient.

According to another of its aspects, the present invention also relates to a method for treating the pathologies indicated above, which comprises the administration, to a patient, of an effective dose of a compound according to the invention or of a pharmaceutically acceptable salt thereof.

The invention claimed is:

1. A Compound of formula (I):

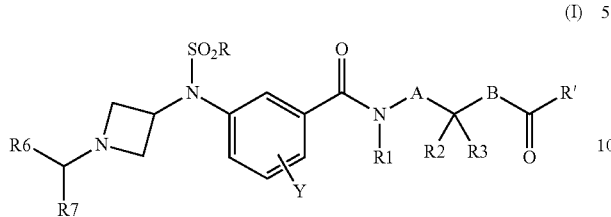

wherein:
R represents a $(C_1-C_6)$alkyl or halo$(C_1-C_6)$alkyl group;
R' represents an NR4R5 or OR8 group;
A and B, which can be present or not, which if they are present, are, independently of one another, one or two carbon atoms, these carbon atoms being substituted with one or more hydrogens or $(C_1-C_6)$alkyl group; the $(C_1-C_6)$alkyl group(s) being optionally substituted with one or more hydroxyl, $(C_1-C_6)$alkoxy, halo$(C_1-C_6)$alkyl, $(C_1-C_6)$alkylS(O)$_p$, NR4R5 or CONR4R5 groups;
A+B represents at most two carbons;
R1 represents a hydrogen atom or a $(C_1-C_6)$alkyl group;
R2 and R3 are, independently of one another, a hydrogen atom or a $(C_1-C_6)$alkyl group; the $(C_1-C_6)$alkyl group being optionally substituted with one or more hydroxyl, $(C_1-C_6)$alkoxy, halo$(C_1-C_6)$alkyl, $(C_1-C_6)$alkylS(O)$_p$, NR4R5 or CONR4R5 groups;
R4 and R5 are, independently of one another, a hydrogen atom or a $(C_1-C_6)$alkyl group, or R4 and R5, together with the nitrogen atom which carries them, form an azetidine, pyrrolidine, piperidine, azepane, piperazine, homopiperazine, morpholine, thiomorpholine, thiomorpholine S-oxide or thiomorpholine S-dioxide group, the NR4R5 group being optionally substituted by a $(C_1-C_6)$ alkyl group;
R6 and R7 each represent a phenyl group, the phenyl group being optionally substituted with one or more substituents selected from a hydrogen atom, a halogen, a $(C_1-C_6)$alkyl, halo$(C_1-C_6)$alkyl, $(C_1-C_6)$alkoxy, halo$(C_1-C_6)$ alkoxy or cyano group;
Y represents a hydrogen atom, halogen, $(C_1-C_6)$alkyl, halo $(C_1-C_6)$alkyl, $(C_1-C_6)$alkoxy, halo$(C_1-C_6)$alkoxy, $(C_1-C_6)$alkylS(O)$_p$ or cyano group;
R8 represents a hydrogen atom, a $(C_1-C_6)$alkyl, halo$(C_1-C_6)$alkyl group, allyl or a phenyl$(C_1-C_6)$alkyl group, the phenyl group being optionally substituted with 1 or 2 O-methyl groups; and
p is 0, 1 or 2;
or a salt thereof.

2. The compound of formula (I) according to claim 1, wherein:
R represents a methyl;
A and B, which can be present or not, which if they are present, are, independently of one another, a —CH$_2$—;
R1 represents a hydrogen atom;
R2 and R3 represent, independently of one another, a hydrogen atom or a $(C_1-C_6)$alkyl group; the $(C_1-C_6)$ alkyl group being optionally substituted with a hydroxyl group;
R4 and R5 represent, independently of one another, a hydrogen atom or a methyl group, or R4 and R5, together with the nitrogen atom which carries them, form a morpholine;
R6 and R7 each represent a phenyl group, optionally substituted in the para position with one or more substituents selected from a halogen, $(C_1-C_6)$alkyl, halo$(C_1-C_6)$ alkyl, $(C_1-C_6)$alkoxy, halo$(C_1-C_6)$alkoxy or cyano group;
R8 represents a hydrogen atom or a $(C_1-C_6)$alkyl group; and
Y represents a hydrogen, halogen, $(C_1-C_6)$alkoxy group, $(C_1-C_6)$alkyl; a cyano; or a halo$(C_1-C_6)$alkyl group.

3. The compound of formula (I) according to claim 2, wherein:
R6 and R7 are each a phenyl group substituted with a chlorine, fluorine or bromine atom or a Me, OMe, CN, CF$_3$ or OCF$_3$ group, in the para-position; and
Y represents a hydrogen, a halogen, a $(C_1-C_6)$alkoxy group; a $(C_1-C_6)$alkyl group; a cyano; or a halo$(C_1-C_6)$ alkyl group.

4. The compound of formula (I) according to claim 2, wherein:
Y is a hydrogen, chlorine, fluorine or bromine atom or a Me, OMe, CN or CF$_3$ group.

5. The compound of formula (I) according to claim 4, wherein:
R6 and R7 are each a phenyl group substituted with a chlorine, fluorine or bromine atom or a Me, OMe, CN, CF$_3$ or OCF$_3$ group, in the para-position.

6. The compound of formula (I) according to claim 1, wherein said compound is selected from the group consisting of:
3-({1-[bis(4-chlorophenyl)methyl]azetidin-3-yl}methanesulphonylamino)-N—((S)-1-carbamoylethyl)benzamide;
3-({1-[bis(4-chlorophenyl)methyl]azetidin-3-yl}methanesulphonylamino)-N-carbamoylmethyl-5-fluorobenzamide;
3-({1-[bis(4-chlorophenyl)methyl]azetidin-3-yl}methanesulphonylamino)-N—((S)-1-carbamoylethyl)-5-fluorobenzamide;
3-({1-[bis(4-chlorophenyl)methyl]azetidin-3-yl}methanesulphonylamino)-N—((R)-1-carbamoylethyl)-5-fluorobenzamide;
3-({1-[bis(4-chlorophenyl)methyl]azetidin-3-yl}methanesulphonylamino)-N—((R)-1-carbamoylethyl)benzamide;
3-({1-[bis(4-chlorophenyl)methyl]azetidin-3-yl}methanesulphonylamino)-N—((S)-1-carbamoyl-2-hydroxyethyl)benzamide;
3-({1-[bis(4-chlorophenyl)methyl]azetidin-3-yl}methanesulphonylamino)-N-(2-carbamoylethyl)benzamide;
3-({1-[bis(4-chlorophenyl)methyl]azetidin-3-yl}methanesulphonylamino)-N-(2-morpholin-4-yl-2-oxoethyl)benzamide;
3-({1-[bis(4-chlorophenyl)methyl]azetidin-3-yl}methanesulphonylamino)-N—((S)-1-methylcarbamoylethyl)benzamide;
3-({1-[bis(4-chlorophenyl)methyl]azetidin-3-yl}methanesulphonylamino)-N—((S)-1-carbamoylpropyl)benzamide;
3-({1-[bis(4-chlorophenyl)methyl]azetidin-3-yl}methanesulphonylamino)-N—((S)-1-carbamoyl-3-methylbutyl)benzamide;
3-({1-[bis(4-chlorophenyl)methyl]azetidin-3-yl}methanesulphonylamino)-N—((S)-1-carbamoyl-2-methylpropyl)-5-fluorobenzamide;

3-({1-[bis(4-chlorophenyl)methyl]azetidin-3-yl}methanesulphonylamino)-N—((S)-1-carbamoyl-2-hydroxyethyl)-5-fluorobenzamide;

3-({1-[bis(4-chlorophenyl)methyl]azetidin-3-yl}methanesulphonylamino)-N—((S)-1-carbamoylpropyl)-5-fluorobenzamide;

3-({1-[bis(4-chlorophenyl)methyl]azetidin-3-yl}methanesulphonylamino)-N-(methylcarbamoylmethyl)benzamide;

3-({1-[bis(4-chlorophenyl)methyl]azetidin-3-yl}methanesulphonylamino)-N-(carbamoylmethyl)benzamide;

(S)-2-[3-({1-[bis(4-chlorophenyl)methyl]azetidin-3-yl}methanesulphonylamino)benzoylamino]propionic acid tert-butyl ester;

(S)-2-[3-({1-[bis(4-chlorophenyl)methyl]azetidin-3-yl}methanesulphonylamino)benzoylamino]propionic acid;

3-({1-[bis(4-chlorophenyl)methyl]azetidin-3-yl}methanesulphonylamino)benzoylaminoacetic acid tert-butyl ester;

4-[3-({1-[bis(4-chlorophenyl)methyl]azetidin-3-yl}methanesulphonylamino)-5-fluorobenzoylamino]butyric acid tert-butyl ester;

(S)-2-[3-({1-[bis(4-chlorophenyl)methyl]azetidin-3-yl}methanesulphonylamino)-5-fluorobenzoylamino]propionic acid tert-butyl ester;

3-({1-[bis(4-chlorophenyl)methyl]azetidin-3-yl}methanesulphonylamino)-N—((S)-1-carbamoylethyl)-5-methoxybenzamide;

3-({1-[bis(4-chlorophenyl)methyl]azetidin-3-yl}methanesulphonylamino)-N—((S)-1-dimethylcarbamoylethyl)benzamide;

4-[3-({1-[bis(4-chlorophenyl)methyl]azetidin-3-yl}methanesulphonylamino)benzoylamino]butyric acid tert-butyl ester;

(S)-2-[3-({1-[bis(4-chlorophenyl)methyl]azetidin-3-yl}methanesulphonylamino)-5-fluorobenzoylamino]propionic acid and the sodium salt thereof;

3-({1-[bis(4-chlorophenyl)methyl]azetidin-3-yl}methanesulphonylamino)-5-fluoro-N—((S)-1-methylcarbamoylethyl)benzamide;

3-({1-[bis(4-chlorophenyl)methyl]azetidin-3-yl}methanesulphonylamino)-N-((1S,2R)-1-carbamoyl-2-hydroxypropyl)benzamide;

3-({1-[bis(4-chlorophenyl)methyl]azetidin-3-yl}methanesulphonylamino)-N-(3-carbamoylpropyl)-5-fluorobenzamide;

[3-({1-[bis(4-chlorophenyl)methyl]azetidin-3-yl}methanesulphonylamino)benzoylamino]acetic acid;

3-({1-[bis(4-chlorophenyl)methyl]azetidin-3-yl}methanesulphonylamino)-N—((S)-1-carbamoylethyl)-2-fluorobenzamide;

3-({1-[bis(4-chlorophenyl)methyl]azetidin-3-yl}methanesulphonylamino)-N—((S)-1-methylcarbamoylethyl)-2-fluorobenzamide;

3-({1-[bis(4-chlorophenyl)methyl]azetidin-3-yl}methanesulphonylamino)-N—((S)-1-carbamoylethyl)-6-fluorobenzamide;

3-({1-[bis(4-chlorophenyl)methyl]azetidin-3-yl}methanesulphonylamino)-N—((S)-1-carbamoylpropyl)-6-fluorobenzamide;

3-({1-[bis(4-chlorophenyl)methyl]azetidin-3-yl}methanesulphonylamino)-N—((S)-1-carbamoyl-2-methylpropyl)-6-fluorobenzamide;

3-({1-[bis(4-chlorophenyl)methyl]azetidin-3-yl}methanesulphonylamino)-N—((S)-1-methylcarbamoylethyl)-6-fluorobenzamide;

3-({1-[bis(4-chlorophenyl)methyl]azetidin-3-yl}methanesulphonylamino)-N—((S)-1-carbamoylpropyl)-4-fluorobenzamide;

3-({1-[bis(4-chlorophenyl)methyl]azetidin-3-yl}methanesulphonylamino)-N-carbamoylmethyl-5-methylbenzamide;

3-({1-[bis(4-chlorophenyl)methyl]azetidin-3-yl}methanesulphonylamino)-N—((S)-1-carbamoylethyl)-5-methylbenzamide;

3-({1-[bis(4-chlorophenyl)methyl]azetidin-3-yl}methanesulphonylamino)-N—((S)-1-carbamoylpropyl)-5-methylbenzamide;

3-({1-[bis(4-chlorophenyl)methyl]azetidin-3-yl}methanesulphonylamino)-N—((S)-1-carbamoyl-2-methylpropyl)-5-methylbenzamide;

3-({1-[bis(4-chlorophenyl)methyl]azetidin-3-yl}methanesulphonylamino)-N—((S)-1-methylcarbamoylethyl)-5-methylbenzamide;

3-({1-[bis(4-chlorophenyl)methyl]azetidin-3-yl}methanesulphonylamino)-N—((S)-1-carbamoyl-2-hydroxyethyl)-5-methylbenzamide;

3-({1-[bis(4-chlorophenyl)methyl]azetidin-3-yl}methanesulphonylamino)-N—((S)-1-carbamoylethyl)-5-chlorobenzamide;

3-({1-[bis(4-chlorophenyl)methyl]azetidin-3-yl}methanesulphonylamino)-N—((S)-1-carbamoylpropyl)-5-chlorobenzamide;

3-({1-[bis(4-chlorophenyl)methyl]azetidin-3-yl}methanesulphonylamino)-N—((S)-1-carbamoyl-2-methylpropyl)-5-chlorobenzamide;

3-({1-[bis(4-chlorophenyl)methyl]azetidin-3-yl}methanesulphonylamino)-N—((S)-1-methylcarbamoylethyl)-5-chlorobenzamide;

3-({1-[bis(4-chlorophenyl)methyl]azetidin-3-yl}methanesulphonylamino)-N—((S)-1-carbamoyl-2-hydroxyethyl)-5-chlorobenzamide;

3-({1-[bis(4-chlorophenyl)methyl]azetidin-3-yl}methanesulphonylamino)-N—((S)-1-carbamoylethyl)-5-bromobenzamide;

3-({1-[bis(4-chlorophenyl)methyl]azetidin-3-yl}methanesulphonylamino)-N—((S)-1-carbamoylpropyl)-5-bromobenzamide;

3-({1-[bis(4-chlorophenyl)methyl]azetidin-3-yl}methanesulphonylamino)-N—((S)-1-carbamoyl-2-methylpropyl)-5-bromobenzamide;

3-({1-[bis(4-chlorophenyl)methyl]azetidin-3-yl}methanesulphonylamino)-N—((S)-1-methylcarbamoylethyl)-5-bromobenzamide;

3-({1-[bis(4-chlorophenyl)methyl]azetidin-3-yl}methanesulphonylamino)-N—((S)-1-carbamoyl-2-hydroxyethyl)-5-bromobenzamide;

3-({1-[bis(4-chlorophenyl)methyl]azetidin-3-yl}methanesulphonylamino)-N-carbamoylmethyl-5-trifluoromethylbenzamide;

3-({1-[bis(4-chlorophenyl)methyl]azetidin-3-yl}methanesulphonylamino)-N—((S)-1-carbamoylethyl)-5-trifluoromethylbenzamide;

3-({1-[bis(4-chlorophenyl)methyl]azetidin-3-yl}methanesulphonylamino)-N—((S)-1-carbamoylpropyl)-5-trifluoromethylbenzamide;

3-({1-[bis(4-chlorophenyl)methyl]azetidin-3-yl}methanesulphonylamino)-N—((S)-1-carbamoyl-2-methylpropyl)-5-trifluoromethylbenzamide;

3-({1-[bis(4-chlorophenyl)methyl]azetidin-3-yl}methanesulphonylamino)-N—((S)-1-methylcarbamoylethyl)-5-trifluoromethylbenzamide;

3-({1-[bis(4-chlorophenyl)methyl]azetidin-3-yl}methanesulphonylamino)-N—((S)-1-carbamoyl-2-hydroxyethyl)-5-trifluoromethylbenzamide;

3-({1-[bis(4-chlorophenyl)methyl]azetidin-3-yl}methanesulphonylamino)-N—((S)-1-carbamoylethyl)-5-cyanobenzamide;

3-({1-[bis(4-chlorophenyl)methyl]azetidin-3-yl}methanesulphonylamino)-N—((S)-1-carbamoylpropyl)-5-cyanobenzamide;

3-({1-[bis(4-chlorophenyl)methyl]azetidin-3-yl}methanesulphonylamino)-N—((S)-1-carbamoyl-2-methylpropyl)-5-cyanobenzamide;

3-({1-[bis(4-chlorophenyl)methyl]azetidin-3-yl}methanesulphonylamino)-N—((S)-1-methylcarbamoylethyl)-5-cyanobenzamide;

3-({1-[bis(4-chlorophenyl)methyl]azetidin-3-yl}methanesulphonylamino)-N—((S)-1-carbamoyl-2-hydroxyethyl)-5-cyanobenzamide;

(S)-2-[3-({1-[bis(4-chlorophenyl)methyl]azetidin-3-yl}methanesulphonylamino)-6-fluorobenzoylamino]propionic acid and the trifluoroacetic acid salt thereof;

(S)-2-[3-({1-[bis(4-chlorophenyl)methyl]azetidin-3-yl}methanesulphonylamino)-5-methylbenzoylamino]propionic acid and the trifluoroacetic acid salt thereof;

(S)-2-[3-({1-[bis(4-chlorophenyl)methyl]azetidin-3-yl}methanesulphonylamino)-5-chlorobenzoylamino]propionic acid and the trifluoroacetic acid salt thereof;

(S)-2-[3-({1-[bis(4-chlorophenyl)methyl]azetidin-3-yl}methanesulphonylamino)-5-bromobenzoylamino]propionic acid and the trifluoroacetic acid salt thereof;

(S)-2-[3-({1-[bis(4-chlorophenyl)methyl]azetidin-3-yl}methanesulphonylamino)-3-trifluoromethylbenzoylamino]propionic acid and the trifluoroacetic acid salt thereof;

(S)-2-[3-({1-[bis(4-chlorophenyl)methyl]azetidin-3-yl}methanesulphonylamino)-5-cyanobenzoylamino]propionic acid and the trifluoroacetic acid salt thereof;

3-({1-[bis(4-bromophenyl)methyl]azetidin-3-yl}methanesulphonylamino)-N—((S)-1-carbamoylethyl)-5-fluorobenzamide;

3-({1-[bis(4-trifluoromethylphenyl)methyl]azetidin-3-yl}methanesulphonylamino)-N—((S)-1-carbamoylethyl)-5-fluorobenzamide;

3-({1-[bis(4-cyanophenyl)methyl]azetidin-3-yl}methanesulphonylamino)-N—((S)-1-carbamoylethyl)-5-fluorobenzamide;

3-({1-[bis(4-methoxyphenyl)methyl]azetidin-3-yl}methanesulphonylamino)-N—((S)-1-carbamoylethyl)-5-fluorobenzamide;

3-({1-[bis(4-fluorophenyl)methyl]azetidin-3-yl}methanesulphonylamino)-N—((S)-1-carbamoylethyl)-5-fluorobenzamide;

(S)-2-[3-({1-[bis(4-chlorophenyl)methyl]azetidin-3-yl}methanesulphonylamino)-5-fluorobenzoylamino]propionic acid methyl ester;

3-({1-[bis(4-methylphenyl)methyl]azetidin-3-yl}methanesulphonylamino)-N—((S)-1-carbamoylpropyl)-5-fluorobenzamide;

3-({1-[bis(4-bromophenyl)methyl]azetidin-3-yl}methanesulphonylamino)-N—((S)-1-methylcarbamoylethyl)-5-fluorobenzamide;

(S)-2-[3-({1-[bis(4-bromophenyl)methyl]azetidin-3-yl}methanesulphonylamino)-5-fluorobenzoylamino]propionic acid;

(S)-2-[3-({1-[bis(4-chlorophenyl)methyl]azetidin-3-yl}methanesulphonylamino)-5-fluorobenzoylamino]propionic acid ethyl ester and 3-({1-[bis(4-trifluoromethoxyphenyl)methyl]azetidin-3-yl}methanesulphonylamino)-N—((S)-1-carbamoylpropyl)-5-fluorobenzamide.

7. A pharmaceutical composition comprising a compound of formula (I) according to claim 1.

8. A pharmaceutical composition comprising a compound of formula (I) according to claim 1 or a pharmaceutically acceptable salt thereof and at least one pharmaceutically acceptable excipient.

9. A process for preparing compounds of formula (I), according to claim 1, for which R' is NR4R5, comprising reacting a compound of formula (5),

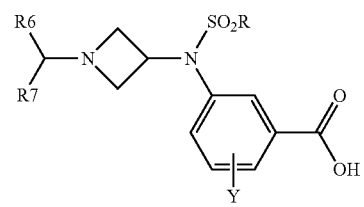

in which R, R6, R7 and Y are as defined in claim 1 with a compound of formula (6),

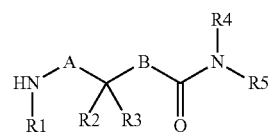

in which R1, R2, R3, R4, R5, A and B are as defined in claim 1;

in an inert solvent, in the presence of a coupling agent and optionally in the presence of an additive for preventing racemization forming a product which is isolated and optionally converted to an addition salt with an acid.

10. A process for preparing compounds of formula (I), according to claim 1, for which R' is OR8, comprising reacting a compound of formula (5):

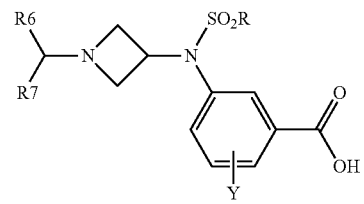

in which R, R6, R7 and Y are as defined in claim 1 with a compound of formula (7):

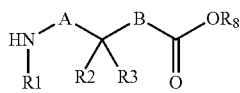

in which R1, R2, R3, R8, A and B are as defined in claim 1, are reacted in an inert solvent, in the presence of a coupling agent and optionally in the presence of an additive for preventing racemization, forming a product which is isolated and optionally converted to an addition salt with an acid.

11. A process for preparing compounds of formula (I), according to claim 1 for which R' is OR8 and R8 is H, comprising hydrolyzing the OR8 function of the compounds of claim 1 wherein R8 is selected from the group consisting of a ($C_1$-$C_6$)alkyl group, a halo($C_1$-$C_6$)alkyl group, an allyl group and a phenyl($C_1$-$C_6$)alkyl group, the phenyl group being optionally substituted with 1 or 2 O-methyl groups forming a hydrolyzed product which is isolated and optionally converted to an addition salt with a base.

12. A process for preparing compounds of formula (I), according to claim 1 for which R' is NR4R5, comprising reacting a compound of formula (I) for which R' is OR8 and R8 is H with an amino derivative: HNR4R5, in which R4 and R5 are as defined in claim 1, are reacted in an inert solvent, in the presence of a coupling agent and optionally in the presence of an additive for preventing racemization and the product is isolated and optionally converted to an addition salt with an acid.

13. A process for preparing compounds of formula (5):

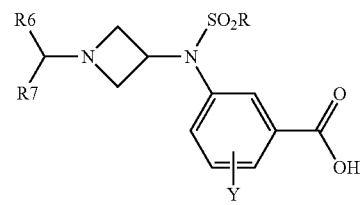

for which Y, R, R6 and R7 are as defined in claim 1, by hydrolysis of the ester function of the compounds of formula (4):

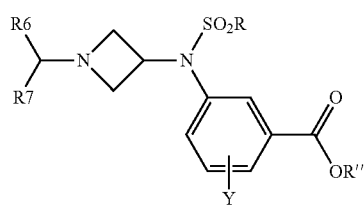

for which Y, R, R6 and R7 are as defined in claim 1 and R" is a ($C_1$-$C_6$)alkyl group, a halo($C_1$-$C_6$)alkyl group, an allyl group or a phenyl($C_1$-$C_6$)alkyl group, the phenyl group being optionally substituted with 1 or 2 O-methyl groups.

* * * * *